(12) United States Patent
Dower et al.

(10) Patent No.: US 7,459,275 B2
(45) Date of Patent: *Dec. 2, 2008

(54) SEQUENCING OF SURFACE IMMOBILIZED POLYMERS UTILIZING MICROFLUORESCENCE DETECTION

(75) Inventors: William J. Dower, Menlo Park, CA (US); Stephen P. A. Fodor, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/446,575

(22) Filed: Jun. 2, 2006

(65) Prior Publication Data

US 2007/0105131 A1 May 10, 2007

Related U.S. Application Data

(63) Continuation of application No. 11/325,809, filed on Jan. 5, 2006, now Pat. No. 7,329,496, which is a continuation of application No. 10/996,692, filed on Nov. 23, 2004, which is a continuation of application No. 10/077,070, filed on Feb. 14, 2002, now Pat. No. 7,056,666, which is a continuation of application No. 08/829,893, filed on Apr. 2, 1997, now abandoned.

(51) Int. Cl.
*C12Q 1/68* (2006.01)
(52) U.S. Cl. ..................................... 435/6; 536/24.3
(58) Field of Classification Search ............ None
See application file for complete search history.

(56) References Cited

U.S. PATENT DOCUMENTS

| | | | |
|---|---|---|---|
| 3,281,860 A | 10/1966 | Adams et al. |
| 3,642,450 A | 2/1972 | Eriksson |
| 3,690,836 A | 9/1972 | Buissiere et al. |
| 3,825,410 A | 7/1974 | Bagshawe |
| 4,016,855 A | 4/1977 | Mimata |
| 4,031,197 A | 6/1977 | Marinkovich |
| 4,039,288 A | 8/1977 | Moran |
| 4,046,750 A | 9/1977 | Rembaum |
| 4,086,254 A | 4/1978 | Wierenga |
| 4,121,222 A | 10/1978 | Diebold et al. |
| 4,145,406 A | 3/1979 | Schick et al. |
| 4,159,875 A | 7/1979 | Hauser |
| 4,204,929 A | 5/1980 | Bier |
| 4,225,410 A | 9/1980 | Pace |
| 4,258,001 A | 3/1981 | Pierce et al. |
| 4,259,223 A | 3/1981 | Rembaum |
| 4,263,504 A | 4/1981 | Thomas |
| 4,267,234 A | 5/1981 | Rembaum |
| 4,427,415 A | 1/1984 | Cleveland |
| 4,430,299 A | 2/1984 | Horne |
| 4,542,102 A | 9/1985 | Dattagupta et al. |
| 4,562,157 A | 12/1985 | Lowe et al. |
| 4,563,417 A | 1/1986 | Albarella et al. |
| 4,591,570 A | 5/1986 | Chang |
| 4,595,562 A | 6/1986 | Liston et al. |
| 4,608,231 A | 8/1986 | Witty et al. |
| 4,675,299 A | 6/1987 | Witty et al. |
| 4,676,951 A | 6/1987 | Armes et al. |
| 4,678,894 A | 7/1987 | Shafer |
| 4,711,955 A | 12/1987 | Ward et al. |
| 4,713,326 A | 12/1987 | Dattagupta et al. |
| 4,719,087 A | 1/1988 | Hanaway |
| 4,719,615 A | 1/1988 | Feyrer et al. |
| 4,720,786 A | 1/1988 | Hara |
| 4,728,591 A | 3/1988 | Clark et al. |
| 4,737,454 A | 4/1988 | Dattagupta et al. |
| 4,741,043 A | 4/1988 | Bacus |
| 4,777,597 A | 10/1988 | Shiraishi et al. |
| 4,797,355 A | 1/1989 | Stabinsky |
| 4,798,706 A | 1/1989 | Brigati |
| 4,802,101 A | 1/1989 | Hara |
| 4,811,218 A | 3/1989 | Hunkapiller et al. |
| 4,829,010 A | 5/1989 | Chang |
| 4,834,946 A | 5/1989 | Levin |
| 4,837,168 A | 6/1989 | de Jaeger et al. |
| 4,837,733 A | 6/1989 | Shiraishi et al. |
| 4,855,225 A | 8/1989 | Fung et al. |
| 4,877,965 A | 10/1989 | Dandliker et al. |
| 4,885,696 A | 12/1989 | Hara |
| 4,888,695 A | 12/1989 | Shiraishi et al. |

(Continued)

FOREIGN PATENT DOCUMENTS

CA        1248873         1/1989

(Continued)

OTHER PUBLICATIONS

U.S. Appl. No. 07/362,901, filed Jun. 7, 1989, Fodor et al.

(Continued)

*Primary Examiner*—Gary Benzion
*Assistant Examiner*—Stephanie K Mummert
(74) *Attorney, Agent, or Firm*—Sandra E. Wells

(57) ABSTRACT

Means for simultaneous parallel sequence analysis of a large number of biological polymer macromolecules. Apparatus and methods may use fluorescent labels in repetitive chemistry to determine terminal monomers on solid phase immobilized polymers. Reagents which specifically recognize terminal monomers are used to label polymers at defined positions on a solid substrate.

16 Claims, 10 Drawing Sheets

U.S. PATENT DOCUMENTS

| | | | |
|---|---|---|---|
| 4,889,427 A | 12/1989 | Van Veen et al. |
| 4,894,786 A | 1/1990 | Hara |
| 4,894,796 A | 1/1990 | Engel et al. |
| 4,931,223 A | 6/1990 | Bronstein et al. |
| 4,933,147 A | 6/1990 | Hollar et al. |
| 4,939,667 A | 7/1990 | Hara et al. |
| 4,941,092 A | 7/1990 | Hara et al. |
| 4,952,707 A | 8/1990 | Edwards et al. |
| 4,958,281 A | 9/1990 | Hara |
| 4,963,815 A | 10/1990 | Hafeman |
| 4,965,188 A | 10/1990 | Mullis et al. |
| 4,965,725 A | 10/1990 | Rutenberg |
| 4,972,325 A | 11/1990 | Hara |
| 4,981,783 A | 1/1991 | Augenlicht |
| 4,982,326 A | 1/1991 | Kaneko |
| 4,994,373 A | 2/1991 | Stavrianopoulos et al. |
| 4,996,142 A | 2/1991 | Al-Hakim et al. |
| 4,997,278 A | 3/1991 | Finlan et al. |
| 5,002,867 A | 3/1991 | Macevicz |
| 5,028,545 A | 7/1991 | Soini |
| 5,035,863 A | 7/1991 | Finlan et al. |
| 5,047,633 A | 9/1991 | Finlan et al. |
| 5,077,210 A | 12/1991 | Eigler et al. |
| 5,112,736 A | 5/1992 | Caldwell et al. |
| 5,143,854 A * | 9/1992 | Pirrung et al. ............... 436/518 |
| 5,156,810 A | 10/1992 | Ribi |
| 5,171,534 A | 12/1992 | Smith et al. |
| 5,173,260 A | 12/1992 | Zander et al. |
| 5,173,747 A | 12/1992 | Boiarski et al. |
| 5,196,305 A | 3/1993 | Findlay et al. |
| 5,202,231 A | 4/1993 | Drmanac et al. |
| 5,215,882 A | 6/1993 | Bahl et al. |
| 5,215,889 A | 6/1993 | Schultz |
| 5,219,763 A | 6/1993 | Van Hoegaerden |
| 5,229,297 A | 7/1993 | Schnipelsky et al. |
| 5,232,829 A | 8/1993 | Longiaru et al. |
| 5,252,743 A | 10/1993 | Barrett et al. |
| 5,260,190 A | 11/1993 | Shiraishi et al. |
| 5,266,498 A | 11/1993 | Tarcha et al. |
| 5,270,006 A | 12/1993 | Uchigaki et al. |
| 5,270,162 A | 12/1993 | Shiraishi et al. |
| 5,273,632 A | 12/1993 | Stockham et al. |
| 5,281,540 A | 1/1994 | Merkh et al. |
| 5,288,514 A | 2/1994 | Ellman |
| 5,291,763 A | 3/1994 | Cuisinot |
| 5,297,288 A | 3/1994 | Hemminger et al. |
| 5,300,779 A | 4/1994 | Hillman et al. |
| 5,302,509 A * | 4/1994 | Cheeseman ................... 435/6 |
| 5,306,618 A | 4/1994 | Prober et al. |
| 5,310,469 A | 5/1994 | Cunningham et al. |
| 5,318,679 A | 6/1994 | Nishioka |
| 5,320,808 A | 6/1994 | Holen et al. |
| 5,332,666 A | 7/1994 | Prober et al. |
| 5,348,855 A | 9/1994 | Dattagupta et al. |
| 5,362,866 A | 11/1994 | Arnold, Jr. |
| 5,380,489 A | 1/1995 | Sutton et al. |
| 5,382,512 A | 1/1995 | Smethers et al. |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,427,908 A | 6/1995 | Dower et al. |
| 5,436,327 A | 7/1995 | Souther et al. |
| 5,445,934 A | 8/1995 | Fodor et al. |
| 5,449,754 A | 9/1995 | Nishioka |
| 5,451,505 A | 9/1995 | Dollinger |
| 5,470,710 A | 11/1995 | Weiss et al. |
| 5,489,507 A | 2/1996 | Chehab |
| 5,489,678 A | 2/1996 | Fodor et al. |
| 5,491,224 A | 2/1996 | Bittner et al. |
| 5,491,570 A | 2/1996 | Rakuljic et al. |
| 5,492,806 A | 2/1996 | Drmanac et al. |
| 5,492,840 A | 2/1996 | Malmqvist et al. |
| 5,525,464 A | 6/1996 | Drmanac et al. |
| 5,527,681 A | 6/1996 | Holmes |
| 5,532,128 A | 7/1996 | Eggers et al. |
| 5,541,061 A | 7/1996 | Fodor et al. |
| 5,543,061 A | 8/1996 | Baskis |
| 5,545,531 A | 8/1996 | Rava et al. |
| 5,547,839 A * | 8/1996 | Dower et al. ................... 435/6 |
| 5,556,749 A | 9/1996 | Mitsuhashi et al. |
| 5,571,639 A | 11/1996 | Hubbell et al. |
| 5,573,905 A | 11/1996 | Lerner et al. |
| 5,573,950 A | 11/1996 | Graessle et al. |
| 5,578,832 A | 11/1996 | Trulson et al. |
| 5,639,603 A | 6/1997 | Dower et al. |
| 5,639,612 A | 6/1997 | Mitsuhashi et al. |
| 5,653,939 A | 8/1997 | Hollis et al. |
| 5,658,734 A | 8/1997 | Brock et al. |
| 5,665,549 A | 9/1997 | Pinkel et al. |
| 5,688,642 A | 11/1997 | Chrisey et al. |
| 5,695,940 A | 12/1997 | Drmanac et al. |
| 5,700,637 A | 12/1997 | Southern |
| 5,727,098 A | 3/1998 | Jacobson |
| 5,744,305 A | 4/1998 | Fodor et al. |
| 5,770,721 A | 6/1998 | Ershov et al. |
| 5,795,716 A | 8/1998 | Chee et al. |
| 5,800,992 A * | 9/1998 | Fodor et al. ................... 506/9 |
| 5,807,522 A | 9/1998 | Brown et al. |
| 5,830,721 A | 11/1998 | Stemmer et al. |
| 5,837,832 A | 11/1998 | Chee et al. |
| 5,843,767 A | 12/1998 | Beattie |
| 5,869,237 A | 2/1999 | Ward et al. |
| 5,889,165 A | 3/1999 | Fodor et al. |
| 5,902,723 A * | 5/1999 | Dower et al. ................... 435/6 |
| 5,922,534 A | 7/1999 | Lichtenwalter |
| 5,959,098 A | 9/1999 | Goldberg et al. |
| 5,972,619 A | 10/1999 | Drmanac et al. |
| 5,976,896 A | 11/1999 | Kumar et al. |
| 6,013,431 A * | 1/2000 | Soderlund et al. ............... 435/5 |
| 6,054,270 A | 4/2000 | Southern |
| 6,063,339 A | 5/2000 | Tisone et al. |
| 6,083,697 A | 7/2000 | Beecher et al. |
| 6,103,463 A | 8/2000 | Chetverin et al. |
| 6,140,044 A | 10/2000 | Besemer et al. |
| 6,171,797 B1 | 1/2001 | Perbost |
| 6,197,506 B1 | 3/2001 | Fodor et al. |
| 6,210,894 B1 | 4/2001 | Brennan |
| 6,221,653 B1 | 4/2001 | Caren et al. |
| 6,225,625 B1 | 5/2001 | Pirrung et al. |
| 6,235,483 B1 | 5/2001 | Wolber et al. |
| 6,255,053 B1 | 7/2001 | Lichtenwalter |
| 6,270,961 B1 | 8/2001 | Drmanac |
| 6,284,460 B1 | 9/2001 | Fodor et al. |
| 6,316,191 B1 | 11/2001 | Drmanac et al. |
| 6,329,143 B1 | 12/2001 | Stryer et al. |
| 6,346,423 B1 | 2/2002 | Schembri |
| 6,355,432 B1 | 3/2002 | Fodor et al. |
| 6,379,895 B1 | 4/2002 | Fodor et al. |
| 6,399,365 B2 | 6/2002 | Besemer et al. |
| 6,403,957 B1 | 6/2002 | Fodor et al. |
| 6,416,952 B1 | 7/2002 | Pirrung et al. |
| 6,440,667 B1 | 8/2002 | Fodor et al. |
| 6,451,536 B1 | 9/2002 | Fodor et al. |
| 6,458,583 B1 | 10/2002 | Bruhn et al. |
| 6,468,740 B1 | 10/2002 | Holmes |
| 6,491,871 B1 | 12/2002 | Fodor et al. |
| 6,506,558 B1 | 1/2003 | Fodor et al. |
| 6,566,495 B1 | 5/2003 | Fodor et al. |
| 6,582,908 B2 | 6/2003 | Fodor et al. |
| 6,600,031 B1 | 7/2003 | Fodor et al. |
| 6,607,887 B2 | 8/2003 | Chee |
| 6,630,308 B2 | 10/2003 | Stryer et al. |
| 6,646,243 B2 | 11/2003 | Pirrung et al. |

| | | | | | | |
|---|---|---|---|---|---|---|
| 6,660,234 B2 | 12/2003 | Stryer et al. | | EP | 0 631 635 A0 | 9/1993 |
| 6,747,143 B2 | 6/2004 | Stryer et al. | | EP | 0 212 314 B1 | 4/1994 |
| 6,852,490 B2 | 2/2005 | Gentalen et al. | | EP | 0 381 501 B1 | 6/1994 |
| 6,919,211 B1 | 7/2005 | Fodor et al. | | EP | 0 373 203 B1 | 8/1994 |
| 6,955,915 B2 | 10/2005 | Fodor et al. | | EP | 0 677 194 A4 | 1/1996 |
| 7,015,046 B2 | 3/2006 | Wohlstadter et al. | | EP | 0 353 592 B1 | 4/1996 |
| 7,056,666 B2 * | 6/2006 | Dower et al. ............... 435/6 | | EP | 0 677 194 A0 | 5/1996 |
| 7,064,197 B1 | 6/2006 | Rabbani et al. | | EP | 0 396 116 B1 | 2/1997 |
| 7,125,674 B2 | 10/2006 | Beattie | | EP | 0 416 038 B1 | 3/1997 |
| 2002/0155491 A1 | 10/2002 | Fodor et al. | | EP | 0 834 576 A2 | 4/1998 |
| 2002/0155492 A1 | 10/2002 | Fodor et al. | | EP | 0 619 321 | 1/1999 |
| 2002/0155588 A1 | 10/2002 | Fodor et al. | | EP | 0 619 321 B1 | 1/1999 |
| 2002/0192684 A1 | 12/2002 | Fodor et al. | | EP | 0 834 576 A3 | 6/1999 |
| 2003/0003475 A1 | 1/2003 | Fodor et al. | | EP | 0 631 635 B1 | 9/2001 |
| 2003/0017484 A1 | 1/2003 | Fodor et al. | | EP | 0 834 576 B1 | 1/2002 |
| 2003/0104411 A1 | 6/2003 | Fodor et al. | | EP | 0 373 203 B2 | 2/2007 |
| 2003/0119008 A1 | 6/2003 | Fodor et al. | | FR | 2684688 | 6/1993 |
| 2003/0119011 A1 | 6/2003 | Fodor et al. | | GB | 1561042 | 2/1980 |
| 2003/0235853 A1 | 12/2003 | Stryer et al. | | GB | 2129551 | 5/1984 |
| 2004/0029115 A9 | 2/2004 | Dower et al. | | GB | 2228998 A | 9/1990 |
| 2004/0067521 A1 | 4/2004 | Fodor et al. | | GB | 2233654 | 1/1991 |
| 2004/0248147 A1 | 12/2004 | Fodor et al. | | JP | 58-009070 | 1/1983 |
| 2005/0079529 A1 | 4/2005 | Fodor et al. | | JP | 63-223557 | 9/1988 |
| 2005/0095652 A1 | 5/2005 | Fodor et al. | | WO | WO 84/01031 A1 | 3/1984 |
| 2005/0112676 A1 | 5/2005 | Fodor et al. | | WO | WO 84/03151 A1 | 8/1984 |
| 2005/0118706 A1 | 6/2005 | Pirrung et al. | | WO | WO 85/01051 | 3/1985 |
| 2005/0148002 A1 | 7/2005 | Dower et al. | | WO | WO 86/03782 | 7/1986 |
| 2005/0148027 A1 | 7/2005 | Pirrung et al. | | WO | WO 88/01302 | 2/1988 |
| 2005/0153362 A1 | 7/2005 | Pirrung et al. | | WO | WO 89/10414 A1 | 11/1989 |
| 2005/0153363 A1 | 7/2005 | Pirrung et al. | | WO | WO 89/10977 | 11/1989 |
| 2005/0158743 A1 | 7/2005 | Fodor et al. | | WO | WO 89/11548 | 11/1989 |
| 2005/0164249 A1 | 7/2005 | Fodor et al. | | WO | WO 90/00626 | 1/1990 |
| 2005/0214828 A1 | 9/2005 | Pirrung et al. | | WO | WO 90/01564 A1 | 2/1990 |
| 2006/0172327 A1 | 8/2006 | Dower et al. | | WO | WO 90/15070 | 2/1990 |
| 2006/0210452 A1 | 9/2006 | Fodor et al. | | WO | WO 90/02173 A1 | 3/1990 |
| | | | | WO | WO 90/02204 A1 | 3/1990 |
| FOREIGN PATENT DOCUMENTS | | | | WO | WO 90/03382 | 4/1990 |
| DE | 3722958 | 1/1989 | | WO | WO 90/04652 | 5/1990 |
| EP | 0 063 810 A1 | 11/1982 | | WO | WO 90/05789 | 5/1990 |
| EP | 0 130 739 A2 | 1/1985 | | WO | WO 90/05910 A1 | 5/1990 |
| EP | 0 171 150 A2 | 2/1986 | | WO | WO 90/06044 | 6/1990 |
| EP | 0 212 314 A2 | 3/1987 | | WO | WO 90/06045 | 6/1990 |
| EP | 0 235 726 A2 | 9/1987 | | WO | WO 90/08838 A1 | 8/1990 |
| EP | 0 237 362 A1 | 9/1987 | | WO | WO 90/09455 A1 | 8/1990 |
| EP | 0 238 332 A2 | 9/1987 | | WO | WO 90/11372 A1 | 10/1990 |
| EP | 0 268 237 A2 | 5/1988 | | WO | WO 91/00868 | 1/1991 |
| EP | 0 268 237 A3 | 11/1988 | | WO | WO 91/06678 A1 | 5/1991 |
| EP | 0 304 202 A1 | 2/1989 | | WO | WO 91/10746 A1 | 7/1991 |
| EP | 0 212 314 A3 | 7/1989 | | WO | WO 91/13075 A2 | 9/1991 |
| EP | 0 328 256 | 8/1989 | | WO | WO 92/10092 A1 | 6/1992 |
| EP | 0 347 210 | 12/1989 | | WO | WO 92/10587 A1 | 6/1992 |
| EP | 0 416 038 A0 | 1/1990 | | WO | WO 92/10588 | 6/1992 |
| EP | 0 353 592 A2 | 2/1990 | | WO | WO 92/20824 A1 | 11/1992 |
| EP | 0 373 203 A0 | 6/1990 | | WO | WO 93/05183 A1 | 3/1993 |
| EP | 0 373 203 B1 | 6/1990 | | WO | WO 93/09668 | 5/1993 |
| EP | 0 377 729 A0 | 7/1990 | | WO | WO 93/09668 A1 | 5/1993 |
| EP | 0 378 968 A2 | 7/1990 | | WO | WO 93/11262 | 6/1993 |
| EP | 0 381 501 A2 | 8/1990 | | WO | WO 93/17126 | 9/1993 |
| EP | 0 377 729 A4 | 10/1990 | | WO | WO 93/18186 A1 | 9/1993 |
| EP | 0 392 546 A2 | 10/1990 | | WO | WO 93/22053 A1 | 11/1993 |
| EP | 0 396 116 A2 | 11/1990 | | WO | WO 93/22058 A1 | 11/1993 |
| EP | 0 416 817 A2 | 3/1991 | | WO | WO 93/22680 A1 | 11/1993 |
| EP | 0 353 592 A3 | 5/1991 | | WO | WO 93/25563 A1 | 12/1993 |
| EP | 0 378 968 A3 | 6/1991 | | WO | WO 94/11837 A1 | 5/1994 |
| EP | 0 381 501 A3 | 6/1991 | | WO | WO 95/00530 | 1/1995 |
| EP | 0 445 915 A1 | 9/1991 | | WO | WO 95/09248 | 4/1995 |
| EP | 0 396 116 A3 | 1/1992 | | WO | WO 95/09248 A1 | 4/1995 |
| EP | 0 416 038 A4 | 1/1992 | | WO | WO 95/11995 | 6/1995 |
| EP | 0 514 927 A1 | 11/1992 | | WO | WO 95/20681 A1 | 8/1995 |
| EP | 0 624 059 A0 | 5/1993 | | WO | WO 95/25116 A1 | 9/1995 |
| EP | 0 549 388 A1 | 6/1993 | | WO | WO 95/35505 A1 | 12/1995 |
| EP | 0 377 729 B1 | 8/1993 | | WO | WO 96/31622 A1 | 10/1996 |
| | | | | WO | WO 97/10365 A1 | 3/1997 |

| | | |
|---|---|---|
| WO | WO 97/27317 | 7/1997 |

OTHER PUBLICATIONS

U.S. Appl. No. 07/435,316, filed Nov. 13, 1989, Barrett et al.
U.S. Appl. No. 07/492,462, filed Mar. 7, 1990, Pirrung et al.
U.S. Appl. No. 07/624,114, filed Dec. 6, 1990, Fodor et al.
U.S. Appl. No. 07/796,243, filed Nov. 22, 1991, Winkler et al.
U.S. Appl. No. 07/874,849, filed Apr. 22, 1992, McGall et al.
U.S. Appl. No. 07/654,948, filed Sep. 1, 2000, Pirrung et al.
U.S. Appl. No. 09/654,948, filed Nov. 28, 2000, Fodor et al.
Abbott et al., "Manipulation of the Wettability of Surfaces on the 0.1-to 1-Micrometer Scale Through Micromachining and Molecular Self-Assembly," *Science* 257:1380-1382, American Association for the Advancement of Science, Washington D.C. (1992).
Amit et al., "Photosensitive protecting groups of amino sugars and their use in glycoside synthesis. 2-nitrobenzyloxycarbonylamino and 6-nitroveratryloxy-carbonylamino derivatives" *J. Org. Chem.* 39(2):192-196, American Chemical Society, Washington, D.C. (1974).
Bains and Smith, "A novel method for nucleic acid sequence determination," *J. Theor. Biol.* 135:303-307, Academic Press, London, England (1988).
Barinaga, M., "Will 'DNA Chip' Speed Genome Initiative?" *Science* 253:1489, American Association for the Advancement of Science, Washington D.C. (Sep. 27, 1991).
Beltz et al., "Isolation of Multigene Families and Determination of Homologies by Filter Hybridization Methods," *Meth. Enzymol.* 100:266-285, Academic Press, New York, New York (1983).
Bhatia et al., "New Approach To Producing Patterned Biomolecular Assemblies," *J. Am. Chem. Soc.* 114:4432-4433, American Chemical Society, Washington, D.C. (1992).
Blawas et al., "Step-and-Repeat Photopatterning of Protein Features Using Caged-Biotin-BSA: Characterization and Resolution," *Langmuir* 14(15):4243-4250, American Chemical Society, Washington, D.C. (1998).
Blawas, A.S., "Photopatterning of Protein Features using Caged-biotin-Bovine Serum Albumin," dissertation for Ph.D at Duke University in 1998.
Cantor et al., "Report on the Sequencing by Hybridization Workshop," *Genomics* 13:1378-1383, Academic Press, San Diego, California (1992).
Carrano et al., "A High-Resolution, Fluorescence-Based. Semiautomated Method for DNA Fingerprinting," *Genomics* 4:129-136, Academic Press, San Diego, California (1989).
Caruthers, M.H., "Gene Synthesis Machines: DNA Chemistry and Its Uses," *Science* 230:281-285, American Association for the Advancement of Science, Washington D.C. (1985).
Chatterjee et al., "Inducible Alkylation of DNA Using an Oligonucleotide-Quinone Conjugate," *J. Am. Chem. Soc.* 112:6397-6399, American Chemical Society, Washington, D.C. (1990).
Chee et al., "Accessing Genetic Information with High-Density DNA Arrays," *Science* 274:610-614, American Association for the Advancement of Science, Washington D.C. (1996).
Chehab et al. "Detection of specific DNA sequences by fluorescence amplification: A color complementation assay," *Proc. Natl. Acad. Sci. USA* 86:9178-9182, National Academy of Sciences, Washington D.C. (1989).
Chetverin, A.H. and Kramer, F.R., "Oligonucleotide Arrays: New Concepts and Possibilities" *Bio/Technology.* 12:1093-1099, Nature Publishing Co., New York, New York (Nov. 1994).
Chow et al., "A high capacity, reusable oligodeoxythymidine affinity column," *Anal Biochem.* 175:63-66, Academic Press, New York, New York (1988).
Church et al., "Genomic sequencing," *Proc. Natl. Acad. Sci. USA* 81:1991-1995, National Academy of Sciences, Washington D.C. (1984).
Church et al., "Multiplex DNA sequencing," *Science* 240:185-188, American Association for the Advancement of Science, Washington D.C. (1988).
Church, "Computer Assisted Multiplex Sequencing," Progress Report, Harvard Medical School, Boston MA. Dept. of Genetics, 9 pages (1991).

Conner et al., "Detection of sickle cell βs-globin allele by hybridization with synthetic oligonucleotides," *Proc. Natl. Acad. Sci. USA* 80:278-282 (1983).
Coulson et al., *Proc. Natl. Acad. Sci. USA* 83:7821-7825, National Academy of Sciences, Washington D.C. (Oct. 1986).
Craig et al., "Ordering of cosmid clones covering the herpes simplex virus type I (HSV-1) genome: A test case for fingerprinting by hybridisation," *Nucl. Acids Res.* 18:2653-2660, IRL Press, Ltd., London, England (1990).
Crkvenjakov and Drmanac, "An Integral Approach for Complex Genome Studies," research proposal submitted Office of Health and Environmental Research, U.S. Department of Energy, 54 pages (Oct. 1990).
Crkvenjakov et al. "Miniaturization of Sequencing by Hybridization (SBH): A Novel Method For Genome Sequencing" abstract no P37, DOE/NIH Human Genome Contractors/Grantee Workshop (Nov. 1989).
Crkvenjakov et al., "Miniaturization of Sequencing of Hybridization (SBH): A Novel Method for Genome Sequencing," Poster abstract presented at Wolf Trap Genome Sequencing Conference, Vienna, Virginia, USA (1989).
Crkvenjakov, "Sequencing of Megabase Plus DNA by Hybridization: Method Development ENT," Excerpts from DOE Grant No. DE-FB02-88ER60699, 18 pages (Oct. 1990).
Dattagupta et al., "Rapid identification of Microorganisms by Nucleic Acid Hybridization after Labeling the Test Sample," *Anal. Biochem.* 177:85-89, Academic Press, New York, New York (1989).
Dear and Staden, "A sequence assembly and editing program for efficient management of large projects," *Nucl. Acids Res.* 19:3907-3911 (1991).
Donis-Keller et al., "A Genetic Linkage Map of the Human Genome," *Cell* 51:319-337 (1987).
Dower, W.J. and Fodor, S., "The Search for Molecular Diversity (II): Recombinant and Synthetic Randomized Peptide Libraries" *Annu. Rep. Med. Chem.* 26:271-280, Academic Press, New York, New York (1991).
Drmanac et al., "Prospects for a Miniaturized, Simplified and Frugal Human Genome Project," *Sci. Yugoslav.* 16(1-2):97-107 (1990).
Drmanac, R., et al., "An algorithm for the DNA sequence generation from k-tuple word contents of the minimal number of random fragments" *J. Biomol. Struct. Dyn.* 8(5):1085-1102, Adenine Press, Guilderland, NY (1991).
Drmanac, R., et al., "Partial Sequencing by Oligo-hybridization: Concept and Applications in Genome Analysis" The First Intl. Conf. Electrophoresis, Supercomputing, and the Human Genome, Eds. Cantor and Lim, World Scientific, pp. 60-74 (Apr. 10-13, 1990).
Drmanac, R., et al., "Sequencing by Oligonucleotide Hybridization: A Promising Framework in Decoding of the Genome Program?" The First Intl. Conf. Electrophoresis, Supercomputing, and the Human Genome, Eds. Cantor and Lim, World Scientific, pp. 47-59 (Apr. 10-13, 1990).
Drmanac, R., et al., "Sequencing of Megabase Plus DNA by Hybridization: Theory of the Method" *Genomics* 4:114-128, Academic Press, San Diego, California (1989).
Drmanac, R., et al., "DNA Sequence Determination by Hybridization: A Strategy for Efficient Large-Scale Sequencing," *Science* 260:1649-1652, American Association for the Advancement of Science, Washington D.C. (1993).
Drmanac, R., et al., "SBH and the Integration of Complementary Approaches in the Mapping, Sequencing, and Understanding of Complex Genomes," The Second International Conference on Bioinformatics, Supercomputing and Complex Genome Analysis: Proceedings of the Jun. 4-7, 1992 Conference at St. Petersburg Beach, Florida pp. 121-134, (1993).
Drmanac, R., et al., "Sequencing by hybridization: towards an automated sequencing of one million M13 clones arrayed on membranes," *Electrophoresis* 13:566-573, Verlag Chemie, Weinheim, Germany (1992).
Drmanac, R., et al., Laboratory Methods—Reliable Hybridization of Oligonucleotides as Short as Six Nucleotides, *DNA Cell Biol.* 9:527-534, Mary Ann Liebert, New York, New York (1990).

Dunn et al., "Mapping viral mRNAs by sandwich hybridization," *Meth. Enzymol.* 65(1):468-478, Academic Press, New York, New York (1980).

Ekins et al, "Development of Microspot Multi-Analyte Ratiometric Immunoassay Using Dual Fluorescent-Labeled Antibodies," *Analytica Chimica Acta* 227: 73-96, Elsevier, Amsterdam, The Netherlands (1989).

Ekins et al., "High Specific Activity Chemiluminescent and Fluorescent Markers: their Potential Application to High Sensitivity and 'Multi-analyte' Immunoassays," *J. Biolumin. Chemilumin.* 4:59-78, Wiley & Sons, Chichester, England (1989).

Ekins, R.P., "Multi-Analyte immunoassay*," *J. Pharm. Biomed. Anal.* 7(2):155-168, Pergamon Press, Oxford, England (1989).

Elder, J.K., "Image Processing in Nucleic Acid Sequence Analysis," 166 pages, A thesis submitted for the degree of Doctor of Philosophy, University of Oxford (1993).

Estivill and Williamson, "A rapid method to identify cosmids containing rare restriction sites," *Nucl. Acids Res.* 15:1415-1423 (1987).

Evans et al., "Physical Mapping of Complex Genomes by Cosmid Multiplex Analysis" *Proc. Natl. Acad. Sci. USA* 86:5030-5034, National Academy of Sciences, Washington D.C. (Jul. 1989).

Feinberg and Vogelstein, "A Technique for Radiolabeling DNA Restriction Endonuclease Fragments to High Specific Activity" *Anal. Biochem.* 137:266-267, Academic Press, New York, New York (1984) Addendum.

Flanders et al., "A new interferometric alignment technique," *Appl. Phys. Lett.* 31(7):426-429, American Institute of Physics, New York, New York (1977).

Fodor et al., "Light-directed, spatially addressable parallel chemical synthesis" *Science* 251:767-773, American Association for the Advancement of Science, Washington D.C. (1991).

Fodor et al., "Multiplexed biochemical assays with biological chips," *Nature* 364:555-556, Macmillian Journals Ltd., London, England (1993).

Fodor et al., "DNA Sequencing by Hybridization," Address by Stephen Fodor before The Robert A. Welch Foundation, 37th Annual Conference on Chemical Research 40 Years of the DNA Double Helix, Houston, Texas, Oct. 25 & 26, 1993, pp. 3-9 (1993).

Forman et al., "Thermodynamics of Duplex Formation and Mismatch Discrimination of Photolithographically Synthesized Oligonucleotide Arrays," chapter 13, pp. 206-228 from Molecular Modeling of Nucleic Acids, ACS Symposium Series 682, Apr. 13-17, 1997, Leontis et al., eds., American Chemical Society, Washington, D.C.

Gait, eds., pp. 1-115 from Oligonucleotide Synthesis: A Practical Approach, IRL Press, London, England (1984).

Gazard et al., "Lithographic Technique Using Radiation-Induced Grafting of Acrylic Acid into Poly(Methyl Methacrylate) Films," *Polymer Engineering and Science* 20(16):1069-1072, Wiley & Sons, Chichester, England (1980).

Gergen et al., "Filter replicas and permanent collections of recombinant DNA plasmids," *Nucl. Acids Res.* 7(8):2115-2137, IRL Press, London, England (1979).

Geysen et al., "Strategies for epitope analysis using peptide synthesis," *J. Immunol. Method.* 102:259-274, North-Holland Pub. Co., Amsterdam, The Netherlands (1987).

Hanahan et al., "Plasmid Screening at High Colony Density," *Methods Enzymol.* 100:333-342, Academic Press, New York, New York (1983).

Haridasan et al., "Peptide Synthesis using Photolytically Cleavable 2-Nitrobenzyloxycarbonyl Protecting Group," *Proc. Indian Natn. Sci. Acad.* 53A(6):717-728, Indian National Science Academy, New Delhi, India (1987).

Hodgson and Fisk, "Hybridization probe size control: optimized 'oligolabeling'" *Nucl. Acids Res.* 15(15):6295, IRL Press, Ltd., London, England (1987).

Hultman, T., et al., "Direct solid phase sequencing of genomic and plasmid DNA using magnetic beads as solid support," *Nucl. Acids Res.* 17(13):4937-4946, IRL Press, Oxford, England (1989).

Jönsson et al., "Surface immobilization techniques in combination with ellipsometry," *Methods Enzymol.* 137:381-388, Academic Press, New York, New York (1988).

Kaiser et al., "Specific-primer-directed DNA sequencing using automated fluorescence detection," *Nucl. Acids Res.* 17:6087-6102 (1989).

Kerkof and Kelly, "A Procedure for Making Simultaneous Determinations of the Relative Levels of Gene transcripts in Tissues or Cells," *Anal. Biochem.* 188:349-355, Academic Press, New York, New York (1990).

Khrapko et al., "An oligonucleotide hybridization approach to DNA sequencing" *FEBS Lett.* 256(1):118-122, North-Holland on behalf of the Federation of European Biochemical Societies, Amsterdam, The Netherlands (Oct. 1989).

Khrapko et al., "A method for DNA sequencing by hybridization with oligonucleotide matrix," *DNA Sequence—J. DNA Sequencing and Mapping* 1:375-388 (1991).

Khrapko et al., "Hybridization of DNA with Oligonucleotides Immobilized in Gel: A Convenient Method for Detecting Single Base Substitutions," *Molecular Biology* 25:581-591 (Dec. 1991) (Russian original: vol. 25(3), pp. 718-730, May-Jun. 1991).

Kimura et al., "An Immobilized Enzyme Membrane Fabrication Method using an Ink Jet Nozzle," *Biosensors* 4:41-52, Elsevier Applied Science Publishers, Barking, Essex (1988).

Kohara et al., The Physical Map of the Whole *E. coli* Chromosome: Application of a New Strategy for Rapid Analysis and Sorting of a large Genomic Library, *Cell* 50: 495-508, MIT Press, Cambridge, Massachusetts (1987).

Koster et al., *Tetrahedron* 40(1):103-112, Pergamon Press, Oxford, England (1984).

Kreindlin et al., "A Sequenator for Analysis of Diagnostic and Sequencing Microchips," 2 pages, Int'l. Workshop on Sequencing by Hybridization, 2 pages (Oct. 29-30, 1993).

Kremsky et al., "Immobilization of DNA via oligonucleotides containing an aldehyde or carboxylic acid group at the 5' terminus," *Nucl. Acids Res.* 15(7):2891-2909, IRL Press, Oxford, England (1987).

Lamture et al., "Direct detection of nucleic acid hybridization on the surface of a charge coupled device," *Nucl. Acids Res.* 22(11):2121-2125 (1994).

Lander et al., "Genomic Mapping by Fingerprinting Random Clones: A Mathematical Analysis," *Genomics* 2:231-239, Academic Press, San Diego, California (1988).

Larin et al., "Fluoresence in situ hybridisation of multiple probes on a single microscope slide," *Nucl. Acids Res.* 22:3689-3692 (1994).

Lennon, G.G. and H. Lehrach, "Hybridization analyses of arrayed cDNA libraries," *Trends Genet.* 47(10):314-317, Elsevier Science Publishers B.V., Amsterdam, The Netherlands (1991).

Lieberman et al. "A Light Source Smaller Than the Optical Wavelength," *Science* 247:59-61, American Association for the Advancement of Science, Washington D.C. (1990).

Lipshutz et al., "Using Oligonucleotide Probe Arrays To Access Genetic Diversity," *BioTecniques.* 19(3):442-447, Eaton Publishing Co., Natick, Massachusetts (1995).

Lipshutz et al., "DNA Sequence Confidence Estimation," *Genomics* 19:417-424 (1994).

Lipshutz, "Likelihood DNA Sequencing By Hybridization," *J. Biomol. Struct. & Dynamics* 11:637-653 (1993).

Little, "Clone maps made simple," *Nature* 346:611-612, Macmillan Journals Ltd., London, England (1990).

Lockhart et al., "Expression monitoring by hybridization to high-density oligonucleotide arrays," *Nat. Biotechnol.* 14:1675-1680, Nature Publishing Co., New York, New York (1996).

Lysov et al., "A New Method for Determining the DNA nucleotide Sequence by Hybridization with Oligonucleotides," *Doklady Biochemistry* 303:436-438 (May 1989) (Russian original vol. 303(1-6):1508-1511 Nov.-Dec. 1988).

Maskos and Southern, "Parallel analysis of oligodeoxyribonucleotide (oligonucleotide) interactions I. Analysis of factors influencing oligonucleotide duplex formation," *Nucl. Acids Res.* 20:1675-1678 (1992).

Maskos et al., "A novel method for the analysis of multiple sequence variants by hybridisation to oligonucleotides," *Nucl. Acids Res.* 19(21):2267-2268, Oxford University Press, Oxford, England (1993).

Maskos, U. and E.M. Southern A Study of Oligonucleotide Reassociation Using Arrays of Oligonucleotides Synthesized on a Glass Support, *Nucl. Acids Res.* 21:4663-4669, Oxford University Press, Oxford, England (1993).

Maskos, U., A Novel Method Of Nucleic Acid Sequence Analysis, Doctoral Thesis, Univ. of Oxford, 165 pages (1991).

Matteucci et al., "Synthesis of deoxyoligonucleotides on a polymer support," *J. Am. Chem. Soc.* 103:3185-3191, American Chemical Society, Washington, D.C. 1981.

Maxam and Gilbert, "A New Method for Sequencing DNA," *Proc. Natl. Acad. Sci. USA* 74:560-564 (1977).

McCray et al., "Properties and Uses of Photoreactive Caged Compounds," *Ann. Rev. Biophys. Biophys. Chem.* 18:239-270, Annual reviews, Palo Alto, California (1989).

McGall et al., "The Efficiency of Light-Directed Synthesis of DNA Arrays on Glass Substrates," *J. Am. Chem. Soc.* 119(22):5081-5090, American Chemical Society, Washington, D.C. (1997).

McGillis, "Lithography," VLSI Technology, McGraw-Hill Book Company, Chapter 7, pp. 267-300, John Wiley & Sons, New York, New York, USA (1983).

Merrifield, R.B., "Solid Phase peptide Synthesis. 1. The Synthesis of a Tetrapeptide," *J. Am. Chem. Soc.* 85:2149-2154, American Chemical Society, Washington, D.C. (1963).

Michiels et al., "Molecular Approaches to Genome Analysis: A Strategy for the Construction of Ordered Overlapping Clone Libraries" *CABIOS* 3(3):203-210 (1987).

Mirzabekov, "Sequencing of DNA by Hybridization with oligonucleotide matrix (SHOM)," DOE grant application, 8 pages (1992).

Mirzabekov, A.D., "DNA sequencing by hybridization—a megasequencing method and a diagnostic tool?," *TIBTECH* 12:27-32, Elsevier Science Publishers B.V., Amsterdam, The Netherlands (1994).

Nederlof et al., "Three-Color Fluorescence In Situ Hybridization for the Simultaneous Detection of Multiple Nucleic Acid Sequences," *Cytometry* 10:20-27, Wiley-Liss, New York, New York (1989).

Olson et al., "Random-clone strategy for genomic restriction mapping in yeast" *Proc. Natl. Acad. Sci. USA* 83:7826-7830, National Academy of Sciences, Washington D.C. (Oct. 1986).

Patchornik et al., "Photosensitive Protecting Groups" *J. Am. Chem. Soc.* 92(21):6333-6335, American Chemical Society, Washington, D.C. (Oct. 21, 1970).

Pease et al., "Light-generated oligonucleotide arrays for rapid DNA sequence analysis," *Proc. Natl. Acad. Sci. USA* 91:5022-5026, National Academy of Sciences, Washington D.C. (1994).

Pevzner et al., "Improved Chips for Sequencing by Hybridization," *J. Biomol. Struct. & Dynamics* 9:399-410 (1991).

Pevzner, P.A., "I-Tuple DNA sequencing: Computer analysis" *J. Biomol. Struct. Dyn.* 7(1):63-73, Adenine Press, Guilderland, New York, New York (1989).

Pillai, V.N., "Photoremovable Protecting Groups in Organic Synthesis," *Synthesis*, pp. 1-26 (1980).

Pirrung et al., "Comparison of Methods for Photochemical Phosphoramidite-Based DNA Synthesis," *J. Org. Chem.* 60:6270-6276, American Chemical Society, Washington, D.C. (1995).

Pirrung et al., "Proofing of Photolithographic DNA Synthesis with 3'.5'—Dimethoxybenzoinyloxycarbonyl-Protected Deoxynucleoside Phosphoramidites," *J. Org. Chem.* 63(2):241-246, American Chemical Society, Washington, D.C. (1998).

Polsky-Cynkin et al., "Use of DNA Immobilized on Plastic and Agarose Supports to Detect DNA by Sandwich Hybridization," *Clin. Chem.* 31(9):1438-1443, American Association For Clinical Chemistry, Washington, D.C. (1985).

Poustka et al., "Molecular approaches to mammalian genetics" *Cold Spring Harbor Symp. Quant. Biol.* 51(Pt. 1):131-139, Cold Spring Harbor Laboratory Press, Cold Spring Harbor, New York (1986).

Prober et al., "A System for Rapid DNA Sequencing with Fluorescent Chain-Terminating Dideoxynucleotides," *Science* 238:336-341 (1987).

Quesada et al., "High-Sensitivity DNA Detection with a Laser-Exited Confocal Fluorescence Gel Scanner," *Biotechniques* 10:616, Eaton Publishing Co., Natick, Massachusetts (1991).

Rabbee et al., "A genotype calling algorithm for affymetrix SNP arrays," *Bioinformatics* 22:7-12 (2006).

Raoult et al., "The line blot: an immunoassay for monoclonal and other antibodies," *J. Immunological Meth.* 125:57-65 (1989).

Rentrop et al., "Aminoalkylsilane-treated glass slides as support for in situ hybridization of keratin cDNAs to frozen tissue sections under varying fixation and pretreatment conditions," *Histochem. J.* 18(5):271-276, Chapman and Hall, London, England (1986).

Renz et al., "A colorimetric method for DNA hybridization," *Nucl. Acids Res.* 12(8):3435-3445, IRL Press Ltd., London, England (1984).

Saiki et al., "Analysis of enzymatically amplified β-globin and HLA-DQ.alpha. DNA with Allele-specific oligonucleotide probes," Nature 324:163-166, Macmillan Journals Ltd., London, England (1986).

Sanger et al., "DNA Sequencing with Chain-terminating Inhibitors," Proc. Natl. Acad. Sci. USA 74:5463-5467 (1977).

Sheldon et al., "Matrix DNA Hybridization," *Clin. Chem.* 39(4):718-719, American Association For Clinical Chemistry, Washington, D.C. (1993).

Southern et al., "Analyzing and Comparing Nucleic Acid Sequences by Hybridization to Arrays of Oligonucleotides: Evaluation Using Experimental Models" Genomics 13:1008-1017, Academic Press, San Diego, California (1992).

Southern et al., "Arrays of complementary oligonucleotides for analysing the hybridisation behaviour of nucleic acids," *Nucl. Acids Res.* 22:1368-1373 (1994).

Southern, E.M., "Detection of Specific Sequences Among DNA Fragments Separated by Gel Electrophoresis," J. Mol. Biol. 98:503-517, Academic Press, New York, New York (1975).

Stodolsky, "Sequencing by Hybridization (SBH) R&D at the Center for Genetic Engineering in Belgrade, Yugoslavia: The Radomir Crkvenjakov Laboratory in 1989," 6 pages, (publication location and date unknown).

Stodolsky, M., "Sequencing By Hybridization (SBH) The Rasomir Crkvenjakov Laboratory in 1989," 4 pages, (Jun. 1989).

Strezoska, Z., et al., "DNA sequencing by hybridization: 100 bases read by a non-gel-based methods," Proc. Natl. Acad. Sci. USA 88:10089-10093, National Academy of Sciences, Washington, D.C. (1991).

Stryer, L., "DNA Probes and Genes Can be Synthesized by Automated Solid-Phase Methods," from Biochemistry, Third Edition, published by W.H. Freeman & Co., pp. 123-124 (1988).

Stuber et al., "Synthesis and photolytic cleavage of bovine insulin B22-30 on a nitrobenzoylglycyl-poly (ethylene glycol) support," *Int. J. Pept. Protein Res.* 22(3):277-283, Munksgaard, Copenhagen, Denmark (1984).

Sundberg et al., "Spatially-Addressable Immobilization of Macromolecules on Solid Supports," *J. Am. Chem. Soc.* 117(49):12050-12057, American Chemical Society, Washington, D.C. (1995).

Thein and Wallace, "The use of synthetic oligonucleotides as specific hybridization probes in the diagnosis of genetic disorders," in Human Genetic Disease: A Practical Approach, Davies, E.K. (ed.), IRL Press, Oxford, UK, pp. 33-50 (1986).

Urdea et al., "A comparison of non-radioisotopic hybridization assay methods using fluorescent, chemiluminescent and enzyme labeled synthetic oligodeoxyribonucleotide probes," Nucl. Acids Res. 16(11):4937-4956, IRL Press, Ltd., London, England (1988).

Wallace et al., "Hybridization of synthetic oligodeoxyribonucleotides to ΦX 174 DNA: the effect of single base pair mismatch," Nucl. Acids Res. 11(6):3543-3557, IRL Press, Ltd., London, England (1979).

Weetall et al., "Covalent coupling methods for inorganic support materials," *Methods Enzymol.* 44: 134-148, Academic Press, New York, New York (1976).

Wolf et al., "Rapid hybridization kinetics of DNA attached to submicron latex particles," Nucl. Acids Res. 15(7):2911-2926, IRL Press, Ltd., London, England (1987).

Zehavi et al., "Light-Sensitive Glycosides 1. 6-Nitroveratryl β-D-Glucopyranoside and 2-Nitrobenzyl β-D-Glucopyyranoside," *J. Org. Chem.* 37(14):2281-2285, American Chemical Society, Washington, D.C. (1972).

Declaration of Dr. Michael C. Pirrung, submitted by *Incyte and Synteni in Affymetrix, Inc. v. Synteni, Inc., and Incyte Pharmaceuticals, Inc.* litigations.
Declaration of Fodor, submitted by *Incyte and Synteni in Affymetrix, Inc. v. Synteni, Inc. and Incyte Pharmaceuticals, Inc.* litigations.
Declaration of Leighton Read, submitted by *Incyte and Synteni in Affymetrix, Inc. v. Synteni, Inc., and Incyte Pharmaceuticals, Inc.* litigations.
Declaration of Stryer, submitted by *Incyte and Synteni in Affymetrix, Inc. v. Synteni, Inc., and Incyte Pharmaceuticals, Inc.* litigations.
"Order granting motion for partial summary judgment of claims 1-3 of U.S. Patent No. 5,800,992 for indefiniteness of 'substantially complementary'," 12 pages, submitted by *Incyte and Synteni in Affymetrix, Inc. v. Synteni, Inc., and Incyte Pharmaceuticals, Inc.* litigations (Sep. 20, 2001).
Crkvenjakov, Talk presented at DOE/NIH Human Genome Sequencing Conference in Santa Fe, NM.
Format 3 SBH Super Chip.
Lysov et al., "A New Method for Determining the DNA Nucleotide Sequence by Hybridization with Oligonucleotides," Abstract of Human Genome 1: An International Conference on the Status abnd Future of Research on the Human Genome (Oct. 1989).
Mirzabekov, "Sequencing of DNA by Hybridization with oligonucleotides matrix (SHOM)," Engelhardt Institute of molecular Biology Grant Application (Mar. 1992) ("Mirabekov Grant Application, 1992").
"Facts and Submissions," in opposition to EP 1 086 742, 40 pages (dated Jul. 26, 2006).
"Interlocutory Decision in Opposition Proceedings," in opposition to EP 1 086 742, 2 pages (dated Jul. 26, 2006).
"Maintenance of the patent with the documents specified in the final decision," in opposition to EP 1 086 742, 1 page (Dated Nov. 4, 2006).
Declaration of Grant Morgan, in Japanese Patent Application No. 8-324451, 15 pages (dated Sep. 16, 2002).
Claims as granted of EP 834575, 2 pages, (Nov. 28, 2001).
Interlocutory decision in Opposition proceedings, in the Opposition to EP 0834575, 33 pages (dated Jan. 24, 2005).
Analysis of ECLA classification of D1 and D2, 3 pages (submitted Aug. 8, 2005).
"Summary of Facts and Submissions," including preliminary opinion, in the Opposition to EP 0834575, 22 pages (dated Jul. 14, 2004).
Communication concerning Oral Proceeding Minutes, in the Opposition to EP 0834575, 9 pages (dated Dec. 30, 2004).
Interlocutory decision in Opposition proceedings, in the Opposition to EP 0834575, 19 pages (dated Jan. 24, 2005).
"Summary of Facts and Submissions," in the Opposition to EP 0834575, 32 pages (dated Jan. 24, 2005).
"Notice of Appeal," filed by Affymetrix in the Opposition to EP 0834575, 1 page (dated Mar. 23, 2005).
Golub et al, "Molecular Classificatrion of Cancer: Class Discovery and Class Prediction by Gene Expression Monitoring," Science 286:531-537 (1999).
Southern et al. "Parallel synthesis and analysis of large numbers of related chemical compounds: applications to oligonucleotides," Journal of Biotechnology 35:217-227 (1994).
Declaration of Professor Anthony Edward George Cass, in the matter of EP application No. 99202455.4, 25 pages (undated).
Declaration of Dr. James Gerard Wetmur, in the matter of EP 0 834 575, 18 pages (undated Oct. 28, 2003).
Janowski et al., "Aminopropylsilane Treatment for the Surface of Porous Glasses Suitable for Enzyme Immobilisation," J. Chem. Tech. Biotechnol. 51:263-272 (1991).
Kazazlan, "Chapter 14. Use of PCR in the Diagnosis of Monogenic Disease," in PCR Technology, Principles and Applications for DNA Amplification, Erlich, Ed., Stockton Press, New York, New York, pp. 153-169 (1989).
Erlich and Bugawan, "Chapter 16. HLA Class II Gene Polymorphism: DNA Typing, Evolution, and relationship to Disease Susceptibility," in PCR Technology, Principles and Applications for DNA Amplification, Erlich, Ed., Stockton Press, New York, New York, pp. 193-204 (1989).
Downs et al., "New DNA Technology and the DNA Biosensor," Analytical Letters 20(12):1897-1927 (1987).

Submission by Opponent 2 Metrigen, Inc.(Successor-In-Interest to Protogene Laboratories, Inc.) in opposition to European Patent No. 0 619 321, 57 pages (dated Sep. 27, 2003).
Statement of Dr. Paul H. Silverman in the opposition to EP 0619321, 7 pages (dated Jul. 25, 2003).
Coassin, Meeting with Affymax Researcher at Human Genome III Poster Presentation, in the opposition to EP 0619321, 2 pages (submitted Jul. 29, 2003).
Silverman, Affymax and Human Genome III, Oct. 21-23, San Diego, 2 pages, in the opposition to EP 0619321 (submitted Jul. 29, 2003).
Declaration of Dennis W. Solas, in U.S. Patent and Trademark Office Interference Proceeding No. 104,359, 9 pages (dated May 28, 1999).
*OGT v. Affymetrix,* Affymetrix' Opening Submissions, HC 1999 02517, HC 1999 04645 (Mar. 22, 2001) 81 pages (submitted Jul. 29, 2003).
Chronology of the Patentee's Efforts to Develop Polynucleotide Arrays, in the opposition to EP 0619321, 5 pages (submitted Jul 29, 2003).
Prosecution history of U.S. Appl. No. 07/362,901, 55 pages, in the opposition to EP 0619321 (submitted Jul. 29, 2003).
In the matter of *Oxford Gene Technologies v. Affymetrix, Inc.,* Court transcript of Nov. 8, 2000, 21 pages, in the opposition to EP 0619321, 2 pages (submitted Jul. 29, 2003).
Chronology of the Patentee's Efforts to Reduce Region Size, in the opposition to EP 0619321, 6 pages (submitted Jul. 29, 2003).
Jacobs et al., "Combinatorial chemistry—applications of light-directed chemical synthesis," TIBTECH 12:19-26 (1994).
Gallop et al., "Applications of Combinatorial Technologies to Drug Discovery. 1. Background and Peptide Combinatorial Libraries," J. Med. Chem. 37:1233-1251 (1994).
Lipshutz et al., "Advanced DNA sequencing technologies," Current Opinion in Structural Biology 4:376-380 (1994).
Wrotnowski, "Biochip Technology Offers Powerful Tool for Research and Diagnostics," 1page, Genetic Engineering News (1994).
McGall et al., "Light-directed synthesis of high-density oligonucleotide arrays using semiconductor photoresists," Proc. Natl. Acad. Sci. USA 93:13555-13560 (1996).
Beecher et al., "Chemically Amplified Photolithography for the Fabrication of High Density Oligonucleotide Arrays," Polym. Mater. Sci, Eng. 76: 597-598 (1997).
Anderson et al., "Polynucleotide Arrays for Genetic Sequence Analysis," Topics in Current Chemistry 194:117-129 (1997).
Lipshutz et al., "High density synthetic oligonucleotide arrays," Nature Genet., suppl. 21:20-24 (1999).
Barone et al., "Photolithographic Synthesis of High Density Oligonucleotide Probe Atrrays," Nucleosides, Nucleotides & Nucleic Acids 20(4-7):525-531 (2001).
Amendment filed with the United States Patent Office during prosecution of U.S. Appl. No. 08/466,632, dated Sep. 23, 1996, 8 pages (submitted Jul. 29, 2003).
Declaration of Dr. Marc M. Greenberg, in the opposition to EP 0619321, 11 pages (dated Jul. 28, 2003).
Curriculum vitae of Marc M. Greenberg, 25 pages (publication date unknown).
Venkatesan et al., "Improved Utility of Photolabile Solid Phase Synthesis Supports for the Synthesis of Oligonucleotides Containing 3'-Hydroxyl termini," J. Org. Chem. 61:525-529 (1996).
Pirrung et al., "3'-Nitrophenylpropyloxycarbonyl (NPPOC) Protecting Groups for High-Fidelity Automated 5'3' Photochemical DNA Synthesis," Organic Letters 3(8): 1105-1108 (2001).
Beier et al., "Synthesis of Photolabile 5'-O-Phosphoramidites for the Photolithographic Production of Microarrays of inversely Oriented Oligonucleotides," Helvetica Chimica Acta 84:2089-2095 (2001).
Wolter et al., "Polymer support oligonucleotide synthesis XXI): Synthesis of a Henhectacosa Deoxynucleotide by use of a dimeric phosphoramidite synthon," Nucleosides & Nucleotides 5(10):65-77 (1986).
Sondek et al., "A General Strategy for Random Insertion and Substitution Mutagenesis: Substoichiometric Coupling of Trinucleotide Phosphoramidites," Proc. Natl. Acad. Sci. USA 89(8):3581-3585 (2003).

Virnekas et al., "Trinucleotide phosphoramidites: ideal reagents for the synthesis of mixed oligonucleotides for random mutagenesis," Nucl. Acids Res. 22:5600-5607 (1994).

Zehavi et al., "Light-Sensitive Glycosides. II. 2-Nitrobenzyl 6-Deoxy-α-L-mannopyranoside and 2-Nitrobenzyl 6-Deoxy-β-L-galactopyranoside," J. Org. Chem. 37(4):2285-2288 (1972).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA," J. Am. Chem. Soc. 109:7845-7854 (1987).

Wincott et al., "Synthesis, deprotection, analysis and purification of RNA and ribozymes," Nucl. Acids Res. 23(14):2677-2684 (1995).

Scaringe et al., "Novel RNA Synthesis Method Using 5'-O-Silyl-2'-O-orthoester Protecting Groups," J. Am. Chem. Soc. 120:11820-11821 (1998).

Stipp, "Gene Chip Breakthrough; Microprocessors have reshaped our economy, spawned vast fortunes, and changed the way we live. Gene chips could be even bigger," Fortune, p. 56 -6 page transcript (Mar. 31, 1997).

Online European Patent Register—Results, EP 0373203 record printout from Jul. 28, 2003, in the opposition to EP 0619321, 3 pages (submitted Jul. 29, 2003).

Declaration of Edwin Mellor Southern, in the opposition to EP 0373203, with exhibits, 22 pages (Jan. 16, 1998).

First Confidential Witness Statement of Alan-Philippe Blanchard, in the opposition to EP 0619321, 4 pages (dated Jan. 19, 2001).

Expert Report of David Bowen Wallace, P.E., Ph.D., in the opposition to EP 0619321, 59 pages (dated Jan. 18, 2001).

Response of Affymetrix Inc. (Opponent VII) to the Patentee's Reply to Opposition to European Patent No. 0 373 203 B, in the opposition to EP 0619321, 50 pages (submitted Jul. 29, 2003).

Asset Purchase Agreement by and between Protogene Laboratories, Inc. and Metrigen, Inc., 24 pages, in the opposition to EP 0619321 (submitted Jul. 29, 2003).

Reply of Affymetrix, Inc. to Oppositions by Incyte Pharamaceuticals, Inc., Protogene Laboratories, Inc., Multilyte Ltd. and Oxford Gene Technology Limited against European Patent No. 0 619 321, 82 pages (submitted Oct. 17, 2000).

Interlocutory decision in the Opposition Proceedings, in the matteh of EP 0373203, 25 pages (dated Feb. 26, 2002).

Summons to Attend Oral Proceedings Pursuant to Rule 71(I) EPC with annexes, 8 pages, in the matter of EP 0 619 321 (dated Jan. 24, 2003).

Agilent Technologies, "SurePrint technology," 14 pages (2003).

Results of experiments performed by Opponent 4, in the matter of EP 0 834 575, 3 pages (submitted Oct. 1, 2004).

Newman et al., "High resolution patterning system with a single bore objective lens," J. Vac. Sci. Technol. B. 5(1):88-90 (1987).

"fingerprinting," in Dictionary of Science and Technology, Walker, Ed., Published by Larousse, p. 421 (1995).

Augenlicht, "Gene Expression in Human Colonic Biopsies," in Basic an Clinical Perspectives of Colorectal Polyps an Cancer, Ed. Steele, G. et al., Alan R. Liss, Inc. NY, pp. 195-202 (1988).

Declaration of Professor John Sutherland, in the matter of EP 0 834 575, 13 pages (dated Nov. 17, 2004).

Declaration of Stephen Philip Alan Fodor, in the matter of EP 0 834 575, 15 pages (dated Nov. 17, 2004).

"distinguish," and "identify," in Oxford Advanced Learner's Dictionary of Current English, Cowie, Ed., Oxford University Press pp. 350, 615 and 616 (1989).

Declaration by Julian Gordon for Opposing party Abbott Laboratories and Combimatrix Corp. in the matter of EP 0 834 575 B, 14 pages (dated May 24, 2005).

Minutes of the public oral proceedings in EP 0373203 dated Oct. 12, 2005.

Opposition to EP 0764214 by Clondiag Chip Technologies GmbH, 33 pages (filed May 31, 2006).

"Minutes of the oral proceedings before the Opposition Division," from oral proceedings in the opposition against EP 695 941 B1, 28 pages (dated Apr. 15, 2006).

Opposition to EP 0972564 by Applera Corporation, 19 pages (filed Feb. 26, 2004).

Response of Affymetrix to the opposition of EP 0972564 by Applera Corporation, 23 pages (dated Jan. 12, 2005).

"Facts and Submissions," in the opposition to EP 0972564, 7 pages (dated Jul. 19, 2005).

Affymetrix's further observations in the opposition to EP 0972564, 4 pages (dated Jun. 12, 2006).

Third party observations in the opposition to EP 0972564, 17 pages (dated Jun. 12, 2006).

"Decision revoking the European Patent," in the opposition to EP 0972564, 20 pages (dated Jul. 31, 2006).

"Minutes of the oral proceedings before the Opposition Division," from oral proceedings in the opposition to EP 0972564, 4 pages (dated Jul. 31, 2006).

Grounds of Appeal as filed in the opposition to EP 0972564, 20 pages (dated Dec. 7, 2006).

Declaration of Professor Anthony Cass, in the Opposition to EP 0972564, 17 pages (dated Jan. 5, 2005).

Declaration of Professor John David Sutherland, in the Opposition to EP 0972564, 11 pages (dated Jan. 4, 2005).

Declaration of Professor John David Sutherland, in the Opposition to EP 0972564, 3 pages (dated Jun. 7, 2006).

Declaration of Professor Jon Cooper, in the matter of EP application No. 99202441.4, 19 pages (dated Nov. 14, 2002).

Declaration of Professor Anthony Cass, in the matter of EP application No. 99202441.4, 19 pages (dated Nov. 13, 2002).

"Summons to attend oral proceedings pursuant to Rule 71(I) EPC," in the Opposition to EP 0695941, 6 pages (dated Oct. 6, 2005).

"Minutes of the oral proceedings before the Opposition Division," in the Opposition to EP 0695941, 16 pages (dated Apr. 5, 2006).

Annex of the auxiliary 5 claim amendments in the Opposition to EP 0695941, 20 pages (filed Oct. 17, 2006).

Declaration under 37 C.F.R. 1.132, Ann M. Pease, in the prosecution of U.S. Appl. No. 07/624,114, 8 pages (dated Aug. 12, 1992).

Silverman, Notes Concerning the HUGO Sequencing By Hybridization Workshop, Moscow (Nov. 18-21, 1991), 7 pages.

Pirrung, NIH grant application, 21 pages (publication date unknown).

Declaration of Michael C. Pirrung, in *Affymetrix, Inc.* v. *Synteni, Inc. and Incyte Pharmaceuticals, Inc.*, Case No. C98-4508 FMS (MEJ), 21 pages (dated Mar. 19, 1999).

Opposition By Affymetrix, Inc. Against European Patent No. 0 373 203 of Isis Innovation Limited, Notice and Statement, 67 pages, in the opposition to EP 0619321 (submitted Oct. 6, 1999).

Declaration of Dr. Thomas Gingeras, Ph.D., in the opposition to EP 0619321, 10 pages (dated Jan. 14, 1999).

Declaration of Professor Calvin F. Quate, Ph.D., in the opposition to EP 0619321, 14 pages (dated Jan. 9, 1999).

Declaration of Glenn H. McGall, Ph.D. for Affymetrix in the opposition to EP 0619321, 10 pages (dated Jan. 13, 1999).

Response of Affymetrix, Inc. to the Patentee's Reply to Opposition to European Patent No. 0 373 203 B, 53 pages (filed Feb. 3, 1997).

Declaration of Professor Lubert Stryer, M.D., in the opposition to EP 0373203, 9 pages (dated Jan. 28, 1997).

Statutory Declaration of Dr. William Bains in the opposition to EP 0373203, 4 pages (dated Jan. 30, 1997).

Statutory Declaration of Dr. Nicholas Vaughan Ashley in the opposition to EP 0373203, 3 pages (undated).

Joint Claim Construction Statement in *Affymetrix, Inc.* v. *Synteni, Inc. And Incyte Pharmaceuticals, Inc.*, Case No. C98-4507, 39 pages (dated Aug. 27, 1999).

Declaration of Charles Cantor in Opposition to Plaintiff's Motion for a Preliminary Injuction, for Synteni, Inc. and Incyte Pharmaceuticals, Inc. in Case No. C98-4508 FMS (MEJ), 26 pages (dated Mar. 19, 1999).

Patentee's response to the Official Letter dated Mar. 14, 1997 from the prosecution history of EP 0619321, 6 pages (dated Feb. 19, 1998).

Decision of May 26, 1993, in European Patent Application No. 86305459.9, 5 pages (dated May 26, 1993).

Decision of Feb. 28, 1996, in European Patent Application No. 84200792.4, 9 pages (dated Feb. 28, 1996).

Decision of Technical Board of Appeal, in European Patent Application No. 82100124.5, 10 pages (dated Jan. 24, 1989).
Decision of Technical Board of Appeal, in European Patent Application No. 85304490.7, 16 pages (dated Oct. 3, 1990).
Decision of Technical Board of Appeal, in European Patent Application No. 87308436.2, 11 pages (dated Mar. 18, 1993).
Decision of Technical Board of Appeal, in European Patent Application No. 85301297.9, 14 pages (dated Mar. 9, 1994).
Statutory Declaration of Dr. Edwin Southern, in the opposition to EP 0619321, with exhibits, 18 pages (dated Oct. 6, 1999).
Declaration of Dr. Paul Silverman, in *Affymetrix, Inc.* v. *Synteni, Inc. and Incyte Pharmaceuticals, Inc.*, Case No. C98-4507 WHA, 3 pages (dated Nov. 23, 1999).
Declaration of Professor John Sutherland, in the opposition to EP 0619321, 15 pages (dated Oct. 13, 2000).
Schulhof et al., "The final deprotection step in oligonucleotide synthesis is reduced to a mild and rapid ammonia treatment by using labile base-protecting groups," Nucl. Acids Res. 15(2):397-415 (1987).
Hayakawa et al., "Allylic protecting groups in solid-phase DNA synthesis," Nucl. Acids Res. 20:75-76 (1988).
Hayakawa et al., "The Allylic Protection Method in Solid Phase Oligonucleotide Synthesis. An Efficient Preparation of Solid-Anchored DNA Oligomers," J. Am. Chem Soc. 112:1691-1696 (1990).
Köster et al., "N-acyl protecting groups for deoxynucleosides. A quantitative and comparative study," Tetrahedron 37:363-369 (1981).
Sproat et al., "A new linkage for solid phase synthesis of oligodeoxyribonucleotides," Nucl. Acids Res. 13(8):2979-2987 (1988).
Pochet et al., "Synthesis of DNA fragments linked to a solid support," Tetrahedron 43(15):3481-3490 (1987).
Katzhendler et al., "The effect of spacer, linkage and solid support on the synthesis of oligonucleotides," Tetrahedron 45(9):2777-2792 (1989).
Declaration of Stephen P.A. Fodor, in the opposition to EP 0619321, 5 pages (dated Oct. 12, 2000).
Declaration of William Bains in the opposition to EP 0619321, includes exhibits, 13 pages (dated Oct. 13, 2000).
Declaration of J. Leighton Read, M.D., in the opposition to EP 0619321, 4 pages (dated Oct. 30, 2000).
Declaration of Dr. James G. Wetmur, in the opposition to EP 0619321, 9 pages (dated Mar. 5, 2002).
Declaration of Professor Lubert Stryer, M.D., in the opposition to EP 0619321, 15 pages (dated Mar. 6, 2002).
Ekins et al., "Multianalyte microspot immunoassay. The microanalytical 'compact disk' of the future" Ann. Biol. Clin. 50:337-353 (1992).
Ekins et al., "Developing multianalyte assays," TIBTECH 12:89-94 (1994).
Ekins et al., "Microspot®, Array-based, Multianalyte Binding Assays: The Ultimate Microanalytical Technology?" in Microspot Immunoassays and DNA Analysis Techniques: Implications and Practical Aspect, Chapter 24, pp. 640-646 (1992).
Declaration of Stephen Philip Alan Fodor, in the opposition to EP 0619321, 7 pages (dated Jul. 28, 2003).
Declaration of Professor Anthony Edward George Cass, in the opposition to EP 0619321, 15 pages (dated Jul. 17, 2003).
Annex AEGC-1 to the Declaration of Professor Anthony Edward George Cass, in the opposition to EP 0619321, 11 pages (Jul. 17, 2003).
Second Declaration of Professor Anthony Edward George Cass, in the opposition to EP 0619321, 8 pages (dated Jul. 17, 2003).
Annex AEGC-1 to Second Declaration of Professor Anthony Edward George Cass, in the opposition to EP 0619321, 26 pages (Jul. 17, 2003).
Annex AEGC-2 to the Second Declaration of Professor Anthony Edward George Cass, in the opposition to EP 0619321, 7 pages (Jul. 17, 2003).
Annex AEGC-3 to the Second Declaration of Professor Anthony Edward George Cass, in the opposition to EP 0619321, 3 pages (Jul. 17, 2003).
Annex AEGC-4 to the Second Declaration of Professor Anthony Edward George Cass, in the opposition to EP 0619321, 6 pages (Jul. 17, 2003).
Anonymous "Dovebid Webcast Auction," Printout of an advertisement for sale by auction on behalf of Protogene, 5 pages (publication date unknown).
Southern et al. "Parallel synthesis and analysis of large numbers of related chemical compounds: applications to oligonucleotides," Journal of Biotechnology 35:217-227 (1994).
Southern et al., "DNA chips: analyzing sequence by hybridization to oligonucleotides on a large scale," TIG 12(3): 110-115 (1996).
Statement of Dr. Paul H. Silverman in the opposition to EP 0619321, 7 pages (dated Jul. 25, 2003).
Coassin, Meeting with Affymax Researcher at Human Genome III Poster Presentation, in the opposition to EP 0619321, 2 pages (submitted Jul. 29, 2003).
Silverman, Affymax and Human Genome III, Oct. 21-23, San Diego, 2 pages, in the opposition to EP 0619321 (submitted Jul. 29, 2003).
Declaration of Dennis W. Solas, in U.S. Patent and Trademark Office Interference Proceeding No. 104,359, 9 pages (dated May 28, 1999).
*OGT* v. *Affymetrix*, Affymetrix' Opening Submissions, HC 1999 02517, HC 1999 04645 (Mar. 22, 2001) 81 pages (submitted Jul. 29, 2003).
Chronology of the Patentee's Efforts to Develop Polynucleotide Arrays, in the opposition to EP 0619321, 5 pages (submitted Jul. 29, 2003).
Prosecution history of U.S. Appl. No. 07/362,901, 55 pages, in the opposition to EP 0619321 (submitted Jul. 29, 2003).
In the matter of *Oxford Gene Technologies* v. *Affymetrix, Inc.*, Court transcript of Nov. 8, 2000, 21 pages, in the opposition to EP 0619321, 2 pages (submitted Jul. 29, 2003).
Chronology of the Patentee's Efforts to Reduce Region Size, in the opposition to EP 0619321, 6 pages (submitted Jul. 29, 2003).
Jacobs et al., "Combinatorial chemistry—applications of light-directed chemical synthesis," TIBTECH 12:19-26 (1994).
Gallop et al., "Applications of Combinatorial Technologies to Drug Discovery. 1. Backround and Peptide Combinatorial libraries," J. Med. Chem. 37:1233-1251 (1994).
Lipshutz et al., "Advanced DNA sequencing technologies," Current Opinion in Structural Biology 4:376-380 (1994).
Wrotnowski, "Biochip Technology Offers Powerful Tool for Research and Diagnostics," 1 page, Genetic Engineering News (1994).
McGall et al., "Light-directed synthesis of high-density oligonucleotide arrays using semiconductor photoresists," Proc. Natl. Acad. Sci. USA 93:13555-13560 (1996).
Beecher et al., "Chemically Amplified Photolithography for the Fabrication of High Density Oligonucleotide Arrays," Polym. Mater. Sci, Eng. 76: 597-598 (1997).
Anderson et al., "Polynucleotide Arrays for Genetic Sequence Analysis," Topics in Current Chemistry 194:117-129 (1997).
Lipshutz et al., "High density synthetic oligonucleotide arrays," Nature Genet., suppl. 21:20-24 (1999).
Barone et al., "Photolithographic Synthesis of High Density Oligonucleotide Probe Atrrays," Nuclcosides, Nucleotides & Nucleic Acids 20(4-7):525-531 (2001).
Amendment filed with the United States Patent Office during prosecution of U.S. Appl. No. 08/466,632, dated Sep. 23, 1996, 8 pages (submitted Jul. 29, 2003).
Declaration of Dr. Marc M. Greenberg, in the opposition to EP 0619321, 11 pages (dated Jul. 28, 2003).
Curriculum vitae of Marc M. Greenberg, 25 pages (publication date unknown).
Venkatesan et al., "Improved Utility of Photolabile Solid Phase Synthesis Supports for the Synthesis of Oligonucleotides Containing 3'-Hydroxyl termini," J. Org. Chem. 61:525-529 (1996).
Pirrung et al., "3'-Nitrophenylpropyloxycarbonyl (NPPOC) Protecting Groups for High-Fidelity Automated 5'3' Photochemical DNA Synthesis," Organic Letters 3(8): 1105-1108 (2001).
Beier et al., "Synthesis of Photolabile 5'-O-Phosphoramidites for the Photolithographic Production of Microarrays of inversely Oriented Oligonucleotides," Helvetica Chimica Acta 84:2089-2095 (2001).

Wolter et al., "Polymer support oligonucleotide synthesis XXI): Synthesis of a Henhectacosa Deoxynucleotide by use of a dimeric phosphoramidite synthon," Nucleosides & Nucleotides 5(10):65-77 (1986).

Sondek et al., "A General Strategy for Random Insertion and Substitution Mutagenesis: Substoichiometric Coupling of Trinucleotide Phosphoramidites," Proc. Natl. Acad. Sci. USA 89(8):3581-3585 (2003).

Vimekas et al., "Trinucleotide phosphoramidites: ideal reagents for the synthesis of mixed oligonucleotides for random mutagenesis," Nucl. Acids Res. 22:5600-5607 (1994).

Zehavi et al., "Light-Sensitive Glycosides. II. 2-Nitrobenzyl 6-Deoxy-α-L-mannopyranoside and 2-Nitrobenzyl 6-Deoxy-β-L-galactopyranoside," J. Org. Chem. 37(4):2285-2288 (1972).

Usman et al., "Automated Chemical Synthesis of Long Oligoribonucleotides Using 2'-O-Silyated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA," J. Am. Chem. Soc. 109:7845-7854 (1987).

Wincott et al., "Synthesis, deprotection, analysis and purification of RNA and ribozymes," Nucl. Acids Res. 23(14):2677-2684 (1995).

Scaringe et al., "Novel RNA Synthesis Method Using 5'-O-Silyl-2'-O-orthoester Protecting Groups," J. Am. Chem. Soc. 120:11820-11821 (1998).

Stipp, "Gene Chip Breakthrough; Microprocessors have reshaped our economy, spawned vast fortunes, and changed the way we live. Gene chips could be even bigger," Fortune, p. 56- 6 page transcript (Mar. 31, 1997).

Online European Patent Register—Results, EP 0373203 record printout from Jul. 28, 2003, in the opposition to EP 0619321, 3 pages (submitted Jul. 29, 2003).

Declaration of Edwin Mellor Southern, in the opposition to EP 0373203, with exhibits, 22 pages (Jan. 16, 1998).

First Confidential Witness Statement of Alan-Philippe Blanchard, in the opposition to EP 0619321, 4 pages (dated Jan. 19, 2001).

Expert Report of David Bowen Wallace, P.E., Ph.D., in the opposition to EP 0619321, 59 pages (dated Jan. 18, 2001).

Response of Affymetrix Inc. (Opponent VII) to the Patentee's Reply to Opposition to European Patent No. 0 373 203 B, in the opposition to EP 0619321, 50 pages (submitted Jul. 29, 2003).

Asset Purchase Agreement by and between Protogene Laboratories, Inc. and Metrigen, Inc., 24 pages, in the opposition to EP 0619321 (submitted Jul. 29, 2003).

Curriculum Vitae of Professor Roger Ekins, FRS., in the opposition to EP 0619321, 2 pages (submitted Jul. 31, 2003).

Stoll et al. "Protein Microarray Technology," Frontiers in Bioscience 7:c13-32 (2002).

"universal succession," and "universal successor," pp. 1445-1446, Black's Law Dictionary, 7th edition, Garner, Ed., Wesdt Group St. Paul, Minnesota, USA (1999), in the opposition to EP 0619321, 3 pages (submitted Apr. 2, 2004).

Asset Purchase Agreement by and between Protogene Laboratories, Inc. and Metrigen, Inc., 40 pages, in the opposition to EP 0619321 (submitted Apr. 2, 2004).

Declaration of Robert J. Molinari, in the opposition to EP 0619321, 8 pages (dated Jun. 16, 2004).

Asset Purchase Agreement by and between Protogene Laboratories, Inc. and Metrigen, Inc., 67 pages, in the opposition to EP 0619321 (submitted Jan. 10, 2005).

Declaration of Thomas Brennan, in the opposition to EP 0619321, 7 pages (dated Jan. 7, 2005).

Declaration of Albert P. Halluin, in the opposition to EP 0619321, 2 pages (dated Jan. 7, 2005).

Declaration of Nathan Hamilton, in the opposition to EP 0619321, 3 pages (dated Jan. 5, 2005).

Declaration of Don. F. Livornese, in the opposition to EP 0619321, 2 pages (dated Jan. 7, 2005).

Declaration of Mark A. Metcalf, in the opposition to EP 0619321, 1 page (dated Jan. 4, 2005).

Declaration of Thomas Brennan, in the opposition to EP 0619321, 7 pages (dated Jan. 5, 2005).

Broughton, Letter enclosing copy of a Decision of the Opposition Division in relation to European Patent No. 834 575, 34 pages, in the opposition to EP 0619321 (submitted Sep. 6, 2005).

McClure, "The Hidden Value of Intangibles," <http://www.investopedia.com/printable.asp?a=/articles/03/010603.asp>, 2 pages (Jan. 6, 2003).

Van Vleet, "Intangible Asset Valuation Issues Under SFAS 142," 8 pages, from <http://www.williametteinsights.com/02/intangibleasset.html> (Jan. 19, 2006).

Declaration of Jeffrey B. Oster, in the opposition to EP 0619321, 3 pages (dated Jan. 19, 2006).

Slides which show in diagrammatic and outline form the chemistry and process of array preparation in accordance with the invention, in the opposition to EP 0619321, 6 pages (submitted Jan. 23, 2006).

Cama et al., "Total Synthesis of Thienamycin Analogues. 1. Synthesis of the Thienamycin Nucleus and dl-Descysteaminylthienamycin,"J. Am. Chem. Soc. 100(25):8006-8007 (1978).

Second Declaration of Professor John Sutherland, in the opposition to EP 0619321, 1 page (dated Jan. 19, 2006).

Second declaration of Robert J. Molinari, in the opposition to EP 0619321, 1 page (dated Jan. 19, 2006).

Penner, "Affymetrix—universal Successor/Successor Liability Issues," 5 pages, Memo from Baker & McKenzie LLP, in the opposition to EP 0619321 (submitted Jan. 23, 2006).

Entity Details, Protogene Laboratories, Inc., 2 pages, <<http://sos-res.state.de.us/tin/controller>>, (printed Mar. 10, 2006).

Declaration by Julian Gordon, with curriculum vitae, in the opposition to EP 0834575, 13 pages (dated May 24, 2005).

Lee, "Re: Protogene Laboratories, Inc.," Letter from Greenberg Taurig, 2 pages, dated Mar. 22, 2006, in the opposition to EP 0619321 (submitted May 4, 2006).

Statement of Thomas Brennan, Ph.D., in the opposition to EP 0619321, 1 page (dated Mar. 22, 2006).

Molanari, letter to Vossius and Partners, 1 page, dated Mar. 22, 2006, in the opposition to EP 0619321 (submitted May 4, 2006).

Certificate of Dissolution of Protogene Laboratories, Inc., 1 page (dated Aug. 18, 2003).

Herring, Letter to Axel Stellbrink, in the opposition to EP 0619321, 4 pages (dated Sep. 13, 2006).

Fann, Minutes of a Special Meeting of The Board of Directors of Protogene Laboratories, Inc., in the opposition to EP 0619321, 1 page (dated Aug. 25, 2006).

Authorization, form 1003 02.00, in the opposition to EP 0619321, 1 page (dated Sep. 12, 2006).

Brennan, Letter to A. Stellbrink, in the opposition to EP 0619321, 1 page (dated Sep. 10, 2006).

Statutory Declaration of Dr. Nicholas Vaughan Ashley in the opposition to EP 0373203, 8 pages (dated May 26, 1995).

Statutory Declaration of Dr. William Bains in the opposition to EP 0373203, includes exhibits, 19 pages (dated May 24, 1995).

Britten-Kelly and Willis, "Michael Additions to Alkyl Substituted Divinyl Ketones," Synthesis 1980:27 (1980).

Grounds of Opposition to EP 0619 321 B1, 15 pages, in the opposition to EP 0619321, 3 pages (submitted Nov. 26, 1999).

Lockhart et al., "Expression monitoring by hybridization to high-density oligonucleotide arrays," Nature BioTechnology 14:1575-1580 (1996).

Biochemistry Poster Session, 50 pages (Oct. 4-7, 1994).

Opposition to EP 0728520 by PamGene B.V., 27 pages (filed Feb. 18, 2002).

Patentee's response to the opposition, in the opposition to EP 0728520, 17 pages (filed Sep. 30, 2002).

Further comments as to lack of novelty, inventive step and sufficiency, in the opposition to EP 0728520, 11 pages (dated Nov. 14, 2003).

"Decision revoking the European Patent," in the opposition to EP 0728520, 13 pages (dated Jan. 29, 2004).

Patentee's grounds for appeal in the opposition to EP 0728520, 10 pages (dated Jun. 8, 2004).

Opponent's response to Patentee's grounds for appeal, in the opposition to EP 0728520, 6 pages (dated Dec. 15, 2004).

Bray et al., "Simultaneous Multiple Synthesis of Peptide Amides by the Multipin Method. Applications of Vapor-Phase Ammonolysis," J. Org. Chem. 59:2197-2203 (1994).
Bray et al., "Gas phase cleavage of peptides from a solid support with ammonia vapour. Application in simultaneous multiple peptide synthesis," Tetrahedron Letts. 32(43): 6163-6166, abstract only (1991).
Hulmes and Pan, "Selective cleavage of polypeptides with trifluoroacetic acid: applications for microsequencing," Anal. Biochem. 197(2):368-376, abstract only (1991).
Miyatake et al., "Specific chemical cleavage of asparaginyl and glycyl-glycine bonds in peptides and proteins by anhydrous hydrazine vapor," J. Biochem. 115(2):208-212, abstract only (1994).
Zingde et al., "Peptide mapping of proteins in gel bands after partial cleavage with acidic cyanogens bromide vapors," Anal. Biochem. 155(1):10-13, abstract only (1986).
Matsueda, "Deprotection of Nin-formyl tryptophan using 1,2-ethanedithiol in liquid hydrogen fluoride," Int. J. Peptide Protein Res. 20:26-34 (1982).
Claim requests for opposition proceedings for EP 0373203 Oxford Gene Technology, 3 pages (dated Nov. 13, 2001).
CV of van Bueringen, in the opposition to EP 0 728 520 (submitted Nov. 17, 2003).
CV of Ruijtenbeek, in the opposition to EP 0 728 520 (submitted Nov. 17, 2003).
Goldberg et al., "Screen printing: a technology for the batch fabrication of integrated chemical-sensor arrays," Sensors and Actuators B 21:171-183 (1994).
"Summons to attend oral proceedings pursuant to Rule 71(1) EPC," in the opposition to EP 0853679, 10 pages (dated Feb. 14, 2006).
"Minutes of the oral proceedings before the Opposition Division," in the opposition to EP 0853679, 17 pages (dated Sep. 12, 2006).
Augenlicht et al., "Expression of Cloned Sequences in Biopsies of Human Colonic Tissue and in Colonic Carcinoma Cells Induced to Differentiate in Vitro," Cancer Res. 47:6017-6021 (1987).
Dattagupta et al., "Rapid Identification of Microorganisms by Nucleic Acid Hybridization after Labeling the Test Sample, Analytical Biochemistry," Anal. Biochem. 177: 85-89 (1989).
McGarrigle/Saliba/Jiminez regarding the public availability of D3 (Lipshutz et al), e-mail correspondence of Feb. 5-6, 2002, 2 pages.
Date Stamp relating to D3 (Lipshutz et al) from the University of California at Berkeley (cited by patentee).
Shultz/Bickel e-mail regarding release date of Biotechniques vol. 19(3) correspondence of Feb. 2-3, 2005, 2 pages.
Ogretman et al., "Internal cRNA Standards for Quantitative Northern Analysis," BioTechniques 14(6):935-940 (1993).
Kawasaki et al., "Genetic Analysis Using Polymerase Chain Reaction-Amplified DNA and Immobilized Oligonucleotide Probes: Reverse Dot-Blot Typing," Methods in Enzymology 218:369-381 (1993).
Declaration of Dianne Olson, 1 page (dated Jun. 15, 2006).
Date Stamp relating to D3 (Lipshutz et al) from the Loyola University Health Sciences Library.
Date Stamp relating to D3 (Lipshutz et al) from the University of Michigan Medical Library.
Quigley, Fax communication regarding journal issue dates, 1 page, Steenbock Memorial Library, University of Wisconsin-Madison (May 11, 2006).
Curriculum Vitae of Thomas Brendan Ryder, 7 pages (publication date unknown).
Curriculum Vitae of Philip L. McGarrigle Jr., 2 pages (publication date unknown).
Curriculum Vitae of Professor Anthony Edward George Cass, 11 pages (publication date unknown).
Opposition to EP 0834576 by Dr. Peter Schneider, 7 pages (dated Oct. 11, 2002).
Opposition to EP 0834576 by Roche Diagnostics GmbH, 14 pages (filed Oct. 16, 2002).
Opposition to EP 0834576 by Applera Corporation, 20 pages (dated Oct. 14, 2002).
Opposition to EP 0834576 by PamGene B.V., 39 pages (dated Oct. 16, 2002).
Opposition to EP 0834576 by Combimatrix Corporation, 26 pages (dated Oct. 16, 2002).

Opposition to EP 0834576 by Abbott Laboratories, 26 pages (dated Oct. 16, 2002).
Response of the Patentee to the oppositions to EP 0834576, 70 pages (dated Feb. 23, 2004).
"Summary of Facts and Submissions," and "Preliminary opinion (Rule 71a(1) EPC) and reasons therefore," in the oppositions to EP 0834576, 19 pages (dated Jul. 20, 2004).
Abbott Laboratories response to the Summons to Attend Oral Proceedings in the oppositions to EP 0834576, 8 pages (dated Dec. 22, 2004).
Applera's written submissions, in the oppositions to EP 0834576, 15 pages (Dec. 20, 2004).
Patentee's further observations, in the oppositions to EP 0834576, 3 pages (dated Dec. 22, 2004).
Minutes of the oral proceeding, in the oppositions to EP 0834576, 10 pages (dated Feb. 22, 2005).
Patentee's arguments made on appeal, in the oppositions to EP 0834576, 9 pages (dated Sep. 27, 2005).
Abbott Laboratories response to Patentee's Grounds of Appeal, in the oppositions to EP 0834576, 13 pages (dated Feb. 22, 2006).
Combimatrix Corporation's response to Patentee's Grounds of Appeal, in the oppositions to EP 0834576, 12 pages (dated Feb. 22, 2006).
Dr. Schneider's response to Patentee's Grounds of Appeal, in the oppositions to EP 0834576, 11 pages (dated Feb. 22, 2006).
Smith et al., "The synthesis of oligonucleotides containing an aliphatic amino group at the 5' terminus: synthesis of fluorescent DNA primers for use in DNA sequence analysis," Nucleic Acids Research 13(7):2399-2412 (1985).
Skolnick et al., "Simultaneous Analysis of Multiple Polymorphic Loci Using Amplified Sequence Polymorphisms (ASPs)" Genomics 2: 273-279.
Renz, "Polynucleotide-histone H1 complexes as probes for blot hybridization," EMBO 2(6):817-822 (1983).
Order Granting Incyte's Motion for Partial Summary Judgement of invalidity of Claims 4 and 5 of the '992 Patent for lack of Written Description of "Mixture," Denying Affymetrix' Cross-motion with Respect Thereto, and Denying Incyte's Motion for Partial Summary Judgment of invalidity of Claims 4 and 5 of the '992 Patent for indefiniteness, from *Affymetrix, Inc.* vs. *Synteni, Inc. and Incyte Pharmaceuticals, Inc.*, Case No. C-99-21164 JF, 12 pages (filed Oct. 3, 2001).
Order Granting Motion for Partial Summary Judgment of invalidity of Claims 1-3 of U.S. Patent No. 5,800,992 for Indefiniteness of "Substantially Complementary," from *Affymetrix, Inc.* vs. *Synteni, Inc. and Incyte Pharmaceuticals, Inc.*, Case Nos. C-99-21164 JF and C-99-21165 JF, 6 pages (filed Sep. 20, 2001).
Payne, Fax communication to H. Kendall regarding available date of Electrophoresis Supercomputing and the Human Genome: 1st International Conference, 1990, 1 page (dated Jan. 28, 2004).
Declaration of Professor John Sutherland, in the matter of EP 0 834 575, 13 pages (dated Nov. 17, 2004).
Declaration of Professor Anthony Edward George Cass, in the matter of EP application No. 99202455.4, 25 pages (undated).
"array," in the Concise Oxford Dictionary of Current English, Allen et al., Eds., Clarendon Press, Oxford, p. 59, (1990).
Erlich and Bugawan, "Chapter 16. HLA Class II Gene Polymorphism: DNA Typing, Evolution, and relationship to Disease Susceptibility," in PCR Technology, Principles and Applications for DNA Amplification, Erlich, Ed., Stockton Press, New York, New York, pp. 193-204 (1989).
Kazazlan, "Chapter 14. Use of PCR in the Diagnosis of Monogenic Disease," in PCR Technology, Principles and Applications for DNA Amplification, Erlich, Ed., Stockton Press, New York, New York, pp. 153-169 (1989).
Interlocutory decision in Opposition proceedings, from the Opposition to EP 0834575, 39 pages (dated Jan. 24, 2005).
"Judgment Pursuant to Remand from United States District Court" in Interference No. 104,358, 7 pages (mailed Mar. 17, 2003).
Declaration of Ward in U.S. Appl. No. 08/514,875, 28 pages (dated Oct. 26, 1998).
Declaration of Kricka in U.S. Appl. No. 08/514,875, 9 pages (dated Oct. 26, 1998).

Sambrook et al., "Analysis of RNA," in Molecular Cloning, A Laboratory Manual, Second Edition, Smabrook et al., Eds., Cold Spring Harbor Laboratory Press, Cold Spring Harbor, New York, USA, pp. 7.37-7.39 and 7.84 (1989).

Alwine et al., "Method for detection of specific RNAs in agarose gels by transfer to diazobezyloxymethyl-paper and hybridization with DNA probes," Proc. Natl. Acad. Sci. USA 74:5350-5354 (1977).

Alwine et al., "Detection of Specific RNAs or Specific Fragments of DNA by Fractionation in Gels and Transfer to Diazobenzyloxymethyl Paper," Meth. Enzymol. 68: 220-242 (1979).

"Declaration of Dennis W. Solas," in Patent Interference 104,358, 10 pages, (dated May 28, 1999).

Schulhof et al., "The final deprotection step in oligonucleotide synthesis is reduced to a mild and rapid ammonia treatment by using labile base-protecting groups," Nucl. Acids Res. 15:397-416 (1987).

"Complaint for patent infringement," in *Affymetrix, Inc. v. Synteni, Inc. and Incyte Pharmaceuticals, Inc.*, Civil Action No. 98-520, 7 pages, (dated Sep. 1, 1998).

"Brief in Support of Plaintiff Affymetrix' Motion for Preliminary Injunction," in *Affymetrix, Inc. v. Synteni, Inc. and Incyte Pharmaceuticals, Inc.*, Civil Action No. 98-520, 44 pages (dated Apr. 15, 1999).

Deposition of Sir Walter Bodmer in Patent Interference 104,358, 192 pages (dated Jul. 30, 1999).

"Deposition of Larry Kricka," in Patent Interference No. 104,358, 154 pages (dated May 20, 1999).

"Deposition of William C. Lacourse," in Patent Interference No. 104,359, 22 pages (dated Jun. 18, 1999).

"Deposition of Gail Stygall, Ph.D.," in Patent Interference No. 104,359, 31 pages (dated Jun. 17, 1999).

"Deposition of Dennis W. Solas, Ph.D.," in Patent Interference No. 104,359, 130 pages (dated Jun. 16, 1999).

"Deposition of Martin J. Goldberg, Ph.D.," in Patent Interference No. 104,359, 51 pages (dated Jun. 16, 1999).

"Declaration of Teresa M. Corbin," in Patent Interference 104,358, 8 pages (dated Jun. 15, 1999).

"Oligonucleotide" pp. 349-350 in McGraw-Hill Encyclopedia of Science & Technology, 6th Edition, McGraw-Hill Book Company, New York, New York (1987).

"Declaration of Professor Lubert Stryer, M.D.," in European Patent No. 0 373 203 of Isis Limited and Opposition thereto by Affymetrix, 9 pages (dated Jan. 28, 1997).

Parmalee and Kelber, Memo to Judge Torczon re Conference Calls in Interferfence Nos. 104,358 and 104,359, dated Jun. 16, 1999.

"Brown Submission under 37 C.F.R. § 1.666(b)," 25 pages (dated Dec. 19, 2002).

"Judgement Pursuant to Remand from Unites State District Court," 4 pages (dated Mar. 17, 2005).

Declaration of Charles L. Gholz, in U.S. Interference No. 104,359, 5 pages (dated Nov. 22, 1995).

Declaration of Kricka, in U.S. Interference No. 104,359, 13 pages (dated Dec. 3, 1998).

Declaration of Kelber, in U.S. Interference No. 104,359, 2 pages (dated Dec. 3, 1998).

Declaration of William C. LaCourse, in U.S. Interference No. 104,359, 14 pages (dated May 25, 1999).

Declaration of Dr. Gail Stygall, in U.S. Interference No. 104,359, 21 pages (dated May 24, 1999).

Declaration of Sir Walter Bodmer, in U.S. Interference No. 104,359, 10 pages (dated May 27, 1999).

Declaration of Dennis W. Solas, in U.S. Interference No. 104,359, 9 pages (dated May 28, 1999).

Declaration of Martin Goldberg, in U.S. Interference No. 104,359, 4 pages (dated May 26, 1999).

Declaration of Teresa M. Corbin, in U.S. Interference No. 104,359, 3 pages (dated Jun. 15, 1999).

Deposition of Larry Kricka, in U.S. Interference No. 104,359, 52 pages (dated May 20, 1999).

Deposition of William C. LaCourse, Ph.D., in U.S. Interference No. 104,359, 22 pages (dated Jun. 24, 1999).

"Drmanac list of intended motions," in Patent Interference No. 104,552, 4 pages (dated Mar. 20, 2001).

"Judgment pursuant to 37 C.F.R. § 1.662," in the Patent Interference No. 104,658, 2 pages (dated Dec. 14, 2001).

"Judgment pursuant to C.F.R. § 1.662(a)," in the Patent Interference No. 105,089, 3 pages (undated).

Matsuzawa et al., "Containment and growth of neuroblastoma cells on chemically patterned substrates," Journal of Neuroscience Methods 50:253-260 (1993).

Chrisey et al., "Selective Attachment of Synthetic DNA to Self-assembled-monolayer Functionalized Surfaces," Mat. Res. Soc. Symp. Proc. 330:179-184 (Symposium held Nov. 29-Dec. 3, 1993).

Guo et al., "Direct fluorescence analysis of genetic polymorphisms by hybridization with oligonucleotide arrays on glass supports," Nucl. Acids Res.22(24):5456-5465 (1994).

Eggers et al., "A Microchip for Quantitative Detection of Molecules Utilizing Luminescent and Radioisotope Reporter Groups," BioTechniques 17(3):516-524 (1994).

Amendment, from File History of U.S. Patent No. 5,922,534, Paper No. 4, 9 pages (dated Feb. 11, 1997).

Office Action, from File History of U.S. Patent No. 5,922,534, Paper No. 5, 6 pages (dated May 13, 1997).

Amendment 37 C.F.R. 1.116, from File History of U.S. Patent No. 5,922,534, Paper No. 6, 7 pages (dated Jul. 14, 1997).

Response to Office Action, from File History of U.S. Patent No. 5,922,534, Paper No. 11, 4 pages (dated Oct. 27, 1997).

Amendment Under 37 CFR 1.116, from File History of U.S. Patent No. 5,922,534, Paper No. 14, 5 pages (dated Mar. 13, 1998).

Resume, William C. LaCourse, 8 pages (undated).

Curriculum Vitae of James G. Wetmur, 7 pages (dated Jun. 22, 2003).

Letter from Lauren Stevens to Deborah Neville, Esq. of Hewlett-Packard Company (with the Table of Contents of vols. I and II attached, but without vols. I and II), 5 pages (dated Jul. 19, 1994).

Letter from Lauren Stevens to Deborah Neville, Esq. of Hewlett-Packard Company (with the Table of Contents for the Patent Publications attached, but without the referenced binder attached), 3 pages (dated Jul. 20, 1994).

Letter from Lauren Stevens to Deborah Neville of Hewlett-Packard Company regarding Affymetrix Technology License Agreement, 2 pages (dated Jul. 21, 1994).

Facsimile letter from Lauren Stevens to Deborah Neville of Hewlett-Packard Company, 1 page (dated Jul. 26, 1994).

Memo from Lauren Stevens to Affymax "Hewlett-Packard File" regarding "due diligence" (without attachment), 1 page (dated Aug. 4, 1994).

Wetmur et al., "Light-Directed, Spatially Addressable Parallel Chemical Synthesis," Chemtracts—Biochem. Mol. Biol. 2:207-10 (1991).

Stryer, L., "Restriction Fragments can be Separated by Gel Electrophoresis and Visualized," from Biochemistry, Third Edition, published by W.H. Freeman & Co., pp. 119 (1988).

List of Affymetrix internal file numbers, 8 pages (undated).

Affymetrix Patent Portfolio—Overview, 10 pages (undated).

Declaration of James G. Wetmur, in U.S. Interference No. 105,089, 16 pages (dated Jun. 25, 2003).

Declaration of William C. LaCourse, in U.S. Interference No. 105,089, 13 pages (dated Jun. 26, 2003).

Declaration of Vernon A Norviel, in U.S. Interference No. 105,089, 6 pages (dated Jun. 27, 2003).

Declaration of Lauren Stevens, in U.S. Interference No. 105,089, 7 pages (dated Jun. 26, 2003).

Office action, from U.S. Appl. No. 08/412,498, 8 pages, (dated Oct. 7, 1996).

Office action, from U.S. Appl. No. 08/412,498, 4 pages (dated Sep. 3, 1997).

Office action, from U.S. Appl. No. 08/412,498, 5 pages (dated Jan. 21, 1998).

Office action, from U.S. Appl. No. 09/337,710, 5 pages (dated Oct. 3, 2000).

Declaration of Power of Attorney for Patent Application, from U.S. Appl. No. 08/412,498, 1 page (dated Mar. 28, 1995).

Notice of Appeal, from File History of U.S. Patent No. 5,922,534, Paper No. 7, 1 page (dated Aug. 4, 1997).

Associate Power of Attorney, from U.S. Appl. No. 09/337,710, 1 page (dated Jun. 21, 1999).

Appointment of Associate Attorney/Agent 37 CFR 1.34(b), from U.S. Appl. No. 08/412,498, 2 pages (dated Aug. 4, 1997).
Letter from Renee Lamantia to Norviel, 1 page (dated Jul. 22, 1994).
Facsimile letter from Peter Dehlinger to Norviel regarding Affymetrix technology, 2 pages (dated Aug. 23, 1994).
Letter dated Oct. 26, 1994, from Norviel to Neville.
Letter from Wendy Choi to Norviel regarding review of the Affymetrix patent portfolio by Hewlett-Packard, 1 page (dated Aug. 7, 1997).
Letter from Roberta L. Robins to Norviel regarding review of the Affymetrix patent portfolio by Hewlett-Packard, 1 page (dated Aug. 19, 1997).
Summary of References Provided to Hewlett-Packard, 4 page (undated).
Facsimile from Affymetrix to Ed Wong and Deborah Neville attaching Affmetrix Patent Portfolio—Overview, 12 pages (dated Nov. 11, 1994).
Table of references cited by Gordon Stewart, 27 pages (undated).
Agilent Technologies to Expand its Life Science Market Presence with Introduction of New DNA Micro-Array Program, Press Releases, 2 pages (Dec. 14, 1999).
Affymetrix Patent Specification 09/614,068, 199 pages, filed Jul. 11, 2000.
Webster's II New College Dictionary, Houghton Mifflin Company, Boston, Mass. USA, p. 787 (1995).
Davis et al., "Making Synthetic mDNA Probes: General Description," in Basic Methods in Molecular Biology, Elsevier, New York, New York USA, p. 68. (1986).
Gait, Oligonucleotide Synthesis, A Practical Approach, IRL Press, Oxford, England, 235 pages (1984).
"Evaporation," in Encyclopedia of Chemistry (4th ed.), Van Nostrand Reinhold Company, New York, New York, USA, p. 366 (1984).
"Chemistry for Automated DNA/RNA Synthesis," Section 6 in Models 392 and 394 DNA/RNA Syntehsizer manual, pp. 6-1-6-36, Applied Biosystems (1991).
Office Action, Paper 5, U.S. Appl. No. 08/412,498, 6 pages (dated May 13, 1997).
Declaration of Henri M. Sasmor, in US. Interference No. 105,089, 15pages (dated Jun. 27, 2003).
Davis et al., in Basic Methods in Molecular Biology, Elsevier Science Publishing Co., Inc., New York, New York, USA, pp. 62-65 and 75-78 (1986).
CV of Henri M. Sasmor, 2 pages (undated).
Maniatis et al., in Molecular Cloning; A Laboratory Manual, Cold Spring Harbor Press, pp. 313-315 and 326-328 (1982).
Kessler, "Nonradioactive Labeling Methods for Nucleic Acids," Chapter 2 in Nonisotopic DNA Probe Techniques, edited by Larry Kricka, Academic Press, Inc., Sandiego, California, USA, pp. 29-92 (1991).
Dyson, "Immobilization of Nucleic Acids and Hybridization Analysis," Chapter 5 in Essential Molecular Biology vol. 11: A Practical Approach, edited by T.A. Brown, IRL Press, Oxford, England, pp. 111-156 (1991).
Preliminary Amendment and Request for Interference Under 37 CFR 607, Paper 2 to U.S. Appl. No. 09/614,068 14 pages, (dated Sep. 6, 2000).
Supplemental Amendment, Paper 14, to U.S. Appl. No. 09/614,068, 10 pages (dated Apr. 12, 2002).
Declaration of Scott M. K. Lee, in US Interference No. 105,089, 5 pages (dated Aug. 20, 2003).
Declaration of Salvatore J. Arrigo, in US Interference No. 105,089, 5 pages (dated Aug. 20, 2003).
Declaration of Richard W. Evans, in US Interference No. 105,089, 4 pages (dated Aug. 20, 2003).
Kriener, "Rapid genetic sequence analysis using a DNA probe array system," American Laboratory, pp. 39-43 (Mar. 1996).
Abdian, "The bees' knees in bar code," ID Systems 8(8):21-26 (1988).
Absalon et al., "Bleomycin mediated degradation of DNA-RNA hybrids does not involve C-1' chemistry," Nucl. Acids Res. 20:4179-4185 (1992).

Adams et al., "Pentafluorobenzylation of O4-Ethylthymidine and Analogues by Phase-Transfer Catalysis for Determination by Gas Chromatography with Electron Capture Detection," Anal. Chem. 58:345-348 (1986).
Agard et al., "Quantitative Analysis of Electrophoretograms: A Mathematical Approach to Super-Resolution," Anal. Biochem. 111:257-268 (1981).
Arndt-Jovin et al., "Immunofluorescence Localization of Z-DNA in Chromosomes: Quantitation by Scanning Microphotometry and Computer-assisted Image Analysis," J. Cell. Biol. 101:1422-1433 (1985).
Bailey, "Health Care Bar Codes: Descriptors or Identifiers?" Bar Code News, pp. 42-44 (Mar./Apr. 1985).
Bailey, "Upgrading Blood Banks: Checking Out The Library," Bar Code News, pp. 20-24 (Mar./Apr. 1983).
Advertisement, "Data Entry Station," Bar Code News., p. 55 (Sep./Oct. 1983).
Barrows et al., "Measurement of fluorescence using digital integration of video images," J. Histochem. Cytochem. 32:741-746 (1984).
Anonymous, "Bars in the Lab: Two New Technologies Join Forces," Bar Code News, pp. 6-12 (Mar./Apr. 1983).
Bauman et al, "A new method for fluorescence micropcopial localization of specific DNA sequences by in situ hybridization of fluorochrome-labelled RNA.," Exp. Cell Res. 128:485-490 (1980).
Beattie et al., "Review: Gene Synthesis Technology: Recent Developments and Future Prospects," Biotechnology and Applied Biochemistry 10:510-521 (1988).
Binnig and Rohrer, "The Scanning Tunneling Microscope: A new kind of microscope reveals the structures of surfaces atom by atom. The instrument's versatility may extend to investigators in the fields of physics, chemistry and biology," Sci. Am. 253:50-56 (1985).
Blond-Elguindi et al, "Affinity panning of the library of peptides displayed on bacteriophages reveals the binding specificity of BiP," Cell 75:717-728 (1993).
Blouke et al., "800×800 charge-coupled device image sensor," Optical Engineering 22:607-614 (1983).
Böhmer et al., "Flow-Cytometric Determination of Fluorescence Ratios between Differently Stained Particles Is Dependent on Excitation Intensity," J. Histochem. Cytochem. 33:974-976 (1985).
Botstein et al., "Construction of a Genetic Linkage Map in Man Using Restriction Fragment Length Polymorphisms," Am. J. Hum. Genet. 32:314-331 (1980).
Bright and Taylor, "Imaging at Low Light Level in Fluorescence Microscopy," in Applications of fluorescence in the biomedical sciences, Eds Taylor et al., New York, New York, AR Liss, pp. 257-288 (1986).
Britten, "Complementary Strand Association Between Nucleic Acids and Nucleic Acid Gels," Science 142:963-965 (1963).
Chen et al., "A Homogeneous, Ligase-Mediated, DNA Diagnostic Test," Genome Res. 549-556 (1998).
Cho et al., "An Unnatural Biopolymer," Science 2611:303-305 (1993).
Cimino et al., "Psoralens as photoactive probes of nucleic acid structure and function: organic chemistry, photochemistry, and biochemistry," Ann. Rev. Biochem. 54:1151-1193 (1985).
Connor, "Digital imaging of free calcium changes and of spatial gradients in growing processes in single, mammalian central nervous system cells," Proc. Natl. Acad. Sci. USA 83:6179-6183 (1986).
Cramer and Köster, "Synthese von Oligonucleotiden an einem polymeren Träger," Angew Chem. 80:488-489 (1968).
Damha et al., "An improved procedure for derivatization of controlled-pore glass beads for solid-phase oligonucleotide synthesis," Nucl. Acid Res. 18:3813-3821 (1990).
Drmanac et al., "Towards Genomic DNA Sequencing Chip Based on Oligonucleotide Hybridization," Abstracts of the Cold Spring Harbor Laboratory Genome Mapping and Sequencing Conference, p. 53 (May 1990).
Duester et al., "Molecular cloning and characterization of a cDNA for the β subunit of human alcohol dehydrogenase," Proc. Natl. Acad. Sci. USA 81:4055-4059 (1984).
Emlen et al., "A new Elisa for the detection of double-stranded DNA antibodies," J. Immunol. Methods 132:91-101 (1990).

Feinberg et al., "A Technique for Radiolabeling DNA Restriction Endonuclease Fragments to High Specific Activity," Anal. Biochem. 132:266-267 (Addendum). 1984.

Fluke, "Prescription For Hospital Fixed Assets Management," Bar Code News pp. 6-8 (Jul./Aug. 1984).

Gallop et al., "Applications of Combinatorial Technologies to Drug Discovery. 1. Background and Peptide Combinatorial Libraries," J. Med. Chem. 37:1233-1251 (1994).

Gilham, "Immobilized Polynucleotides and Nucleic Acids," Adv. Exp. Med. Biol. 42:173-185 (1974).

Glazer et al., "A stable double-stranded DNA-ethidium homodimer complex: Application to picogram fluorescence detection of DNA in agarose gels," Proc. Natl. Acad. Sci. USA 87:3851-3855 (1990).

Gordon et al., "Applications of Combinatorial Technologies to Drug Discovery. 2. Combinatorial Organic Synthesis, Library Screening Strategies, and Future Directions," J. Med. Chem. 37:1385-1401 (1994).

Gress et al., "Hybridization fingerprinting of high-density cDNA-library arrays with cDNA pools derived from whole tissues," Mammalian Genome 3:609-619 (1992).

Gundersen et al., "Magnetic bead antigen capture enzyme-linked immunoassay in microtitre trays for rapid detection of schistosomal circulating anodic antigen," J. Immunol. Methods 148:1-8 (1992).

Haralambidis et al., "Preparation of base-modified nucleosides suitable for non-radioactive label attachment and their incorporation into synthetic oligodeoxyribonucleotides," Nucl. Acids Res. 15:4857-4876 (1987).

Harmon, "Health Industry Bar Code (HIBC) Task Force Publishes Final Recommendations," Bar Code News p. 11 (Nov./Dec. 1983).

Harmon, "Health Industry Moves Quickly to Adopt Uniform Bar Coding," Bar Code News pp. 20-22 (Sep./Oct. 1983).

Harmon, "New Standards: Bar Code Markings For Healthcare," Bar Code News pp. 10-14 (Jul./Aug. 1984).

Heidmann and Köster, "Polymer Support Oligonucleotide Synthesis, 11: Use of a Novel Hydrophilic Bead Polymer as Carrier," Makromolekulare Chemie 181:2495-2506 (1980).

Hiraoka et al., "The NDA3 Gene of Fission Yeast Encodes β-Tubulin: A Code-Sensitive nda3 Mutation Reversibly Blocks Spindle Formation and Chromosome Movement in Mitosis," Cell 39:349-358 (1984).

Hiraoka et al., "The Use of Charge-Coupled Device for Quantitative Optical Microscopy of Biological Structures," Science 238:36-41 (1987).

Inouye and Hondo,"Microplate Hybridization of Amplified Viral DNA Segment," J. Clin. Microbiol. 28:1469-1472 (1990).

Jablonski and DeLuca, "Immobilization of bacterial luciferase and FMN reductase on glass rods," Proc. Natl. Acad. Sci. USA 73:3848-3851 (1976).

Jacobs and Fodor, "Combinatorial chemistry—applications of light-directed chemical synthesis," TIBTECH 12:19-26 (1994).

Jeffreys et al., "Amplification of human minisatellites by the polymerase chain reaction: towards DNA fingerprinting of single cells," Nucl. Acids Res. 16:10953-10971 (1988).

Kanehisa, "Use of statistical criteria for screening potential homologies in nucleic acid sequences," Nucl. Acids Res. 12:203-213 (1984).

Karlin et al., "Efficient algorithms for molecular sequence analysis," Proc. Natl. Acad. Sci. USA 85:841-845 (1988).

Khorana et al., "A New Approach to the Synthesis of Polynucleotides," Chemistry and Industry p. 1523 (1956).

Köster and Geussenhainer, "A Novel Carrier for Solid Phase Synthesis of Oligomers," Angew. Chem. Internat. Edit. 11(8):713-714 (1972).

Köster, "Polymer Support Oligonucleotide Synthesis VII-5: Use of Inorganic Carriers," Tetrahedron Letters 16:1527-1530, (1972).

Köster, Synthesis of a Structural Gene Coding for the Peptide Hormone Angiotensin II, Part 3: Synthesis of the Fragments d(T-T-T-T-A-A), d(A-T-A-T-C-A-TC-C-C) and d(T-T-A-A-A-A-G-G-G-A-T). Liebigs Ann. Chem. pp. 894-925 (1978).

Kwoh et al., "Transcription-based amplification system and detection of amplified human immunodeficiency virus type 1 with a bead-based sandwich hybridization format," Proc. Natl. Acad. Sci. USA 86:1173-1177 (1989).

Landegren et al., "A Ligase-Mediated Gene Detection Technique," Science 241:1077-1080 (1988).

Lee et al., "Interaction of psoralen-derivatized oligodeoxyribonucleoside methylphosphonates with synthetic DNA containing a promoter for T7 RNA polymerase," Nucl. Acids Res. 16:10681-10697 (1988).

Lipman and Pearson, "Rapid and Sensitive Protein Similarity Searches," Science 227:1435-1441 (1985).

Lund et al., "Assessment of methods for covalent binding of nucleic acids to magnetic beads, Dynabeads™, and the characteristics of bound nucleic acids in hybridization reactions," Nucl. Acid Res. 16(22):10861-10880 (1988).

Lundwall et al., "Isolation and Sequence Analysis of a cDNA Clone Encoding the Fifth Complement Component," J. Biol. Chem. 260:2108-2112 (1985).

Maiolini et al., "Study of an Enzyme Immunoassay Kit for Carcinoembryonic Antigen," Clin. Chem. 26:1718-1722 (1980).

Mathies et al., "High-sensitivity Single-molecule Fluorescence Detection," SPIE 1205:52-59 (1990).

Mathies et al., "Optimization of High-Sensitivity,Fluorescence Detection," Anal. Chem. 62:1786-1791 (1990).

Matteo, Jr., "How To Cure Medical Supply Chaos," Bar Code News pp. 16-18 (Jul./Aug. 1984).

Merrifield, "Solid Phase Synthesis," Science 232:341-347 (1986).

Michael et al., "Randomly Ordered Addressable High-Density Optical Sensor Arrays," Anal. Chem. 70:1242-1248 (1998).

Nelson, "The Universal Product Code," Helmers Publishing, p. 55-85 (1997).

Nguyen et al., "Detection of Single Molecules of Phycoerythrin in Hydrodynamically Focused Flows by Laser-Induced Fluorescence," Anal. Chem. 59:2158-2161 (1987).

Parsons, "Yearly Review: Psoralen Photochemistry," Photochem. Photobiol. 32:813-821 (1980).

Pevzner et al., "Optimal Chips for Megabase DNA Sequencing," Mol. Biol. 25: 459-467 (1991).

Phimister, "Going global," Nature Genet. 21:1 (1999).

Ploem, "New Instrumentation for Sensitive Image Analysis of Fluorescence in Cells and Tissues," in Applications of fluorescence in the biomedical sciences, Eds. Taylor et al., New York, New York, AR Liss, pp. 289-300 (1986).

Pon et al., "Derivatization of Controlled-Pore Glass Beads for Solid-Phase Oligonculeotide Synthesis," Biotechniques 6:768-765 (1988).

Rocks and Riley, "Automatic analysers in clinical biochemistry," Clin. Phys. Physiol. Meas. 7:1-29 (1986).

Rosenthal, " Bush Encounters the Supermarket, Amazed," NY Times pp. A1 and A19 (Feb. 5, 1992).

Rost, "Scanning, video intensification and image processing," and in Quantitative fluorescence microscopy, Cambridge: Cambridge University Press, Chapter 15, pp. 162-178 (1991).

Rozsnyai et al., "Photolithographic Immobilization of Biopolymers on Solid Supports," Angew. Chem. internat. Edit. 31(6):759-761 (1992).

Rye et al., "High-sensitivity two-color detection of double-stranded DNA with a confocal fluorescence gel scanner using ethidium homodimer and thiazole orange," Nucl. Acids Res. 19:327-333 (1990).

Saiki et al., "Primer-Directed Enzymatic Amplification of DNA with a Thermostable DNA Polymerase," Science 239:487-491 (1988).

Scillian et al., "Early Detection of Antibodies Against rDNA-Produced HIV Proteins with a Flow Cytometric Assay," J. Blood 73:2041-2048 (1998).

Shack et al., "Design for a Fast Fluorescent Laser Scanning Microscope," Anal. Quant. Cytol. Histol. 9:509-520 (1987).

Shitara et al., "Advantage of Cocktail-Use of Two Anti-tumor Monoclonal Antibodies, KM-93 and KM-231, in Serum Diagnosis of Cancer," Anticancer Res. 9:999-1004 (1989).

Skolnick and Wallace, "Simultaneous Analysis of Multiple Polymorphic Loci Using Amplified Sequence Polymorphisms (ASPs)," Genomics 2:273-279 (1988).

Smith et al., "The synthesis of oligonucleotides containing an aliphatic amino group at the 5' terminus: synthesis of fluorescent DNA primers for use in DNA sequence analysis," Nucl. Acids Res. 13:2399-2412 (1985).

Smith, "Bar Code: The Data Entry Alternative," Bar Code News pp. 1-2 (Mar. 1982).
Smith et al., "High Throughput DNA Sequencing Using an Automated Electrophoresis Analysis System and a Novel Sequence Assembly Program," Biotechniques 14:1014-1018 (1993).
Smith and Hood, "Mapping and Sequencing the Human Genome: How to Proceed," Bio/Technology 5:674-679 (1987).
Song et al., "Review Article: Photochemistry and Photobiology of Psoralens," Photochem. Photobiol. 29:1177-1197 (1979).
Stanley R., "Help Needed at Central Supply, STAT: Bar Codes Ease Growing Pains," Bar Code News pp. 2-4 (Mar./Apr. 1983).
Anonymous, "Sterile Bar Codes: Guiding Production for a Medical Manufacturer," Bar Code News pp. 14-18 (Mar./Apr. 1983).
Streefkerk et al., "Antigen-Coupled Beads Adherent to Slides: A Simplified Method for Immunological Studies," J. Immunol. Methods 8:251-256 (1975).
Streefkerk et al., "Principle of a Reaction for Simultaneous Detection of Various Antibodies Using Coloured Antigen-Coupled Agarose Beads," in Protides of the Biological Fluids, Peeters Ed., Pergamon Press, Oxford pp. 811-814 (1976).
Tobe et al., "Single-well genotyping of diallelic sequence variations by a two-color ELISA-based oligonucleotide ligation assay," Nucl. Acids Res. 3728-3732 (1996).
Toda et al., "Sequential alterations in the nuclear chromatin region during mitosis of the fission yeast Schizosaccharomyces pombe: video fluorescence microscopy of synchronously growing wild-type and cold-sensitive cdc mutants by using a DNA-binding fluorescent probe," J. Cell Sci. 52:271-287 (1981).
Umesono et al., "Visualization of Chromosomes in Mitotically Arrested Cells of the Fission Yeast Schizosaccharomyces pombe," Current Genetics 7:123-128 (1983).
Vignali, "Multiplexed particle-based flow cytometric assays.," J. Immunol. Meth. 243:243-255 (2000).
Wahlberg et al., "Rapid detection and sequencing of specific in vitro amplified DNA sequences using solid phase methods," Molecular and Cellular Probes 4:285-297 (1990).
Wallace et al., "The use of synthetic oligonucleotides as hybridization probes—II. hybridization of oligonucleotides of mixed sequence to rabbit B-globin DNA," Nucl. Acids Res. 9:879-894 (1981).
Wang and Grayston, "Immunologic Relationship Between Genital Tric, Lympho-Granuloma Venereum, and Related Organisms in a New Microtiter Indirect Immunofluorescence Test," Am. J. Ophthalmology 70:367-374 (1970).
White et al., "An Evaluation of Confocal Versus Conventional Imaging of Biological Structures by Fluorescence Light Microscopy," J. Cell Biol. 105:41-48 (1987).
Ohtsuka et al.,"A new method for 3'-labelling of polyribonucleotides by phosphorylation with RNA ligase and its application to the 3'-modification for joining reactions," Nucl. Acids Res. 6:443-454 (1979).
Uchida, "Synthesis of oligoribonucleotide (2). The synthesis and uses of trimer units having blocking groups at 3'- and 5' ends," Nuc. Acids Res. Symp. 10:187-188 (1981).
Beier and Hoheisel, "Production by quantitative photolithographic synthesis of individually quality checked DNA microarrays," Nucl. Acids Res. 28(4):e11: 6 pages (2000).
Gao et al., "High density peptide microarrays. In situ synthesis and applications," Molecular Diversity, 8:177-187 (2004).
Thompson, "An Introduction to Lithography," Chapter 1, in Introduction to Microlithography Theory, Materials, and Processing, Thompson et al., Eds. American Chemical Society, Washington, D.C., pp. 1-13 and table of contents (1983).
Thompson, "An Introduction to Lithography," Chapter 1, in Introduction to Microlithography Theory, Materials, and Processing, Thompson et al., Eds. American Chemical Society, Washington, D.C., pp. 1-17 and table of contents (1994).
"Decision," 12 pages, from US patent interference No. 104,358 (mailed Sep. 10, 1999).
"Decision," 13 pages, from US patent interference No. 104,359 (mailed Sep. 10, 1999).
Adams M. Automated DNA Sequencing and Analysis, Academic Press, 1994.
Abstracts of papers presented at 1988 meeting on Genome Mapping and Sequencing. Cold Spring Harbor Laboratory, Apr. 27-May 1, 1988 (IAFP 640211-329).
Abstracts of paper presented at the 1994 meeting on Genome Mapping & Sequencing. Cold Spring Harbor Laboratory (IAFP 12968-12969).
Cold Spring Harbor Laboratory. Abstracts of papers presented at the 1990 meeting of Genome Mapping and Sequencing, May 2-6, 1990 (IAFP 598193-326).
Department of Energy, Sequencing of DNA by Hybridization with Oligonucleotides Matrix (SHOM) 1992 (DOE 832-839).
Diagram of Format 3 Combinatorial Chip (IAFP 643752).
DOE/NIH Human Genome Contractors/Grantee Workshop (Santa Fe, NM) Abstracts Nov. 3-4, 1989 (IAFP 597958-598013).
DOE/NIH Human Genome Contractors/Grantee Workshop (Santa Fe, NM) Speaker Abstracts Nov. 3-4, 1989 (IAFP 597926-957).
Drmanac et al., Towards Genome DNA Sequencing Chip Based on Oligonucleotide Hybridization: Modelling and Computer Methods In Molecular Biology and Genetics. Abstracts of the Int'l Conference, Novosibirsk, U.S.S.R. 1990: (IAFP 598068-70).
Drmanac R, Crkvenjakov R. Prospects for Miniaturized, Simplified and Frugal Human Genome Project: The 'Sequencing Chip' Concept. Belgrade, Yugoslavia Oct. 1989 (IAFP 598743-52).
Drmanac R, Crkvenjakov R. Prospects for Miniaturized, Simplified and Frugal Human Genome Project. Genetic Engineering Center, Belgrade, Yugoslavia Mar. 31, 1989 (DOE 520-546).
Drmanac R. Miniaturization of Sequencing by Hybridization. The Sequencing Chip Concept Poster Presentation 1989 (IAFP 598099-117).
Drmanac, R. Sequencing by Hybridization (SBH) on Super Chips. Presentation at BioChip Array Technologies: Fabrication and Applications, May 10, 1995 (IAFP 643753-643771).
Harmon et al. Reading Between the Lines. North American Technology, Inc. 1984:193-205.
Human Genome I: An International Conference on the status and future of research on the Human Genome, Official Program and Abstracts (pp. 46-49), Oct. 2-4, 1989 (UTRF 293-294).
Human Genome II: An International Conference on the status and future of research on the Human Genome, Official Program and Abstracts, Oct. 22-24, 1990 (AVI_134115-75; IAFP598371-430).
International Workshop on Sequencing Hybridization, Program and Abstracts, Oct. 29-30, 1993 (IAFP 598513-598612).
Kreindlin et al. A Sequenator for analysis of diagnostic and sequencing microchips. Engelhardt Institute of Molecular Biology, Russian Academy of Sciences, Moscow (IAFP 598552-53).
Report on the Sequencing by Hybridization Workshop, Moscow, SBH: An idea whose time has probably come, Nov. 19-20, 1991 (DOE 97-108).
U.S. Congress, Office of Technology Assessment. Mapping Our Genes—Genome Projects: How Big? How Fast? Apr. 1988:1-218.
Wolf Trap Genome Sequencing Conference: Program and Abstracts, Oct. 24-26, 1989 (IAFP 597859-597882).
Broude et al., "Positional Sequencing by Hybridization," p. 297, Abstracts of papers presented at the 1994 meeting on Genome Mapping & Sequencing, Cold Spring Harbor Laboratory (1994).
Drmanac et al., "Genome Sequencing Machine," p. 60, Abstracts of papers presented at the 1994 meeting on Genome Mapping & Sequencing, Cold Spring Harbor Laboratory (1994).
Drmanac et al., "Sequence-Ready Maps Constructed from Shotgun Clone Libraries Hybridized with 200 7-mers," p. 61, Abstracts of papers presented at the 1994 meeting on Genome Mapping & Sequencing, Cold Spring Harbor Laboratory (1994).
Drmanac et al., "Toward Categorizing 100,000 Infant Brain cDNA Clones by Oligonucleotide Hybridization," p. 62, Abstracts of papers presented at the 1994 meeting on Genome Mapping & Sequencing, Cold Spring Harbor Laboratory (1994).
Crkvenjakov et al., "Discovery of Sequence Similarities in Large Clone Collections by SBH: Analysis of 22,000 cDNAs and a Model Subclone Library of Cosmid-Sized DNA," p. 48, Abstracts of papers presented at the 1994 meeting on Genome Mapping & Sequencing, Cold Spring Harbor Laboratory (1994).

Ivanov et al., "Oligonucleotide microchip on gel support as an instrument for DNA analysis," p. 296, Abstracts of papers presented at the 1994 meeting on Genome Mapping & Sequencing, Cold Springs Harbor Laboratory (1994).

Sindelar et al., "Parallel Synthesis of Large Numbers of Custom Oligomers in a Multichannel Format," p. 298, Abstracts of papers presented at the 1994 meeting on Genome Mapping & Sequencing, Cold Spring Harbor Laboratory (1994).

Drmanac et al., "Towards Genome DNA Sequencing Chip Based on Oligonucleotide Hybridzation," pp. 242-243, Abstracts of papers presented at the 1992 meeting on Genome Mapping and Sequencing, Cold Spring Harbor Laboratory (1992).

Drmanac et al., "An Alternative Large DNA Sequencing Method: The theoretical and Informational Feasibility of Sequencing by Hybridization," p. 44, Abstracts of papers presented at the 1992 meeting on Genome Mapping & Sequencing, Cold Spring Harbor Laboratory (1992).

Drmanac et al., "Sequencing by Hybridization (SBH): A Production Line to Sequence One Million M13 Clones Arrayed on Membranes," p. 110, Abstracts of papers presented at the 1992 meeting on Genome Mapping & Sequencing, Cold Spring Harbor Laboratory (1992).

Mapping Our Genes, Genome Projects: How Big, How Fast? Congress of the United States Office of Technology Assessment, The Johns Hopkins University Press (1988).

Aller R, Elevitch F. Symposium on Computers in the Clinical Laboratory. Clinics in Laboratory Medicine 1983;3:1-254.

Ekins R, Chu F. Microarrays: their origins and applications. Tibtech 1999;17:217-218.

Gesteland R. Notes on Russia (DOE 6-12).

Hopes this issue jams every computer in the country. MAD Magazine Apr. 1978.

Human Genome III: The International Conference on the status and future of research on the Human Genome, Official Program and Abstracts, Oct. 21-23, 1991 (AVI_131963-132005).

Khrapko et al. Improved Chips for Sequencing by Hybridization. 1991 (DOE 24-35).

Report on Foreign Travel of Richard A. Sachleben, 1991 (DOE 16-23).

Khorlin, et al., "An oligonucleotide matrix hybridization approach to DNA sequencing," Nucl. Acid Res. Symp. Ser. 24:191 (1991).

Lab Notebook pp. 98-106 from Kay Lictenwalter's lab notebook No. 1416. (From interference 105,089, but not in the pdf provided).

Brenner et al. "In vitro cloning of complex mixtures of DNA on microbeads: Physical separation of differentially expressed cDNAs" Proc. Natl. Acad. Sci. USA 97:1665-1670, National Academy of Sciences, Washington D.C. (2000).

Evans et al., "Microfabrication for Automation of Molecular processes in Human Genome Analysis," Clin. Chem. 41(11):1681, American Association For Clinical Chemistry, Washington, D.C. (1995).

Frank et al., "Simultaneous synthesis and biological applications of DNA fragments: An efficient and complete methodology," Methods Enzymol. 134:221-251, Academic Press, New York, New York (1987).

Frank et al., "A new general approach for the simultaneous chemical synthesis of large numbers of oligonucleotides: segmental solid supports," Nucl. Acids Res. 11(13):4365-4377 (1983).

O'Donnell-Maloney and Little, "Microfabrication and array technologies for DNA sequencing and diagnostics," Genetic Analysis: Biomolecular Engineering 13:151-157 (1996).

Keller et al., "A Sensitive Nonisotopic Hybridization Assay for HIV-1 DNA," Anal. Biochem. 177:27-32 (1989).

Jalanko et al., "Screening for Defined Cystic Fibrosis Mutations by Solid-Phase Minisequencing," Clin. Chem. 38:39-43 (1992).

Wilhelm et al., "Analysis of Mutant tRNA Gene Transcripts in Vivo in *Saccharomyces cerevisae* by Abortive Primer Extension," Anal. Biochem. 196:156-160 (1991).

Curriculum Vitae of Professor Anthony Edward George Cass, 11 pages, submitted in the opposition to EP 0607501, (Feb. 14, 2007).

Miyada and Wallace, "Oligonucleotide Hybridization Techniques," Methods Enzymol. 154:94-107 (1987).

"Opposition to EP 0 607 151 in the Name of City of Hope by Affymetrix, Inc.," 25 pages (Aug. 13, 2003).

"Observations in Reply to the Opposition," 16 pages, in the Opposition to EP 0607151 (Apr. 30, 2004).

"Summons to attend oral proceedings pursuant to Rule 71(1) EPC," 10 pages, in the Opposition to EP 0607151 (Oct. 5, 2006).

"Auxiliary Request No. 1," 4 pages, in the Opposition to EP 0607151 (Feb. 16, 2007).

"Auxiliary Request No. 2," 4 pages, in the Opposition to EP 0607151 (Feb. 16, 2007).

"Auxiliary Request No. 3," 4 pages, in the Opposition to EP 0607151 (Feb. 16, 2007).

"Minutes of the oral proceedings before the Opposition Division," 13 pages, in the Opposition to EP 0607151 (May 16, 2007).

"Information," Form 2341 07.02, 1 page, in the Opposition to EP 0607151 (May 16, 2007).

"Inkjet printer,", http://en.wikipedia.org/wiki/Inkjet_printer, last visited May 29, 2007 (Wikipedia).

Bohlen et al., "Electron-Beam Proximity Printing-A New High Speed Lithography Method for Submicron Structures," IBM J. Res. Develop. (1982) 26:568.

Sacra Blue Online, http://www.sacpcug.org/archives/20year/timeline-a.html, last visited May 29, 2007.

Olympus Microscopy Resource Center, http://www.olympusmicro.com/micd/galleries/chips.intel486dxa.html, last visited May 29, 2007.

Innis et al., "DNA Sequencing with Thermus aquaticus DNA Polymerase and Direct Sequencing of Polymerase Chain Reaction-Amplified DNA," Proc. Natl. Acad. Sci. USA, (1988) 85:9436.

Miller, J.P., "Intel Introduces Powerful 80486 Chip, But High Price May Limit Initial Sales", The Wall Street Journal Online, Apr. 11, 1989.

Gelsinger et al., "Microprocessors Circa 2000", IEEE Spectrum, Oct. 1989, 43.

Behlke and Devor, "Chemical Synthesis of Oligonucleotides," http://www.idtdna.com/support/technical/TechnicalBulletinPDF/Chemical_Synthesis_of_Oligonucleotides.pdf, last visited May 29, 2007.

* cited by examiner

SEQUENCE LISTING

<160> NUMBER OF SEQ ID NOS: 1

<210> SEQ ID NO 1
<211> LENGTH: 17
<212> TYPE: DNA
<213> ORGANISM: Artificial sequence
<220> FEATURE:
<223> OTHER INFORMATION: M13 primer

<400> SEQUENCE: 1
gttttcccag tcacgac                                                17

SEQUENCING OF SURFACE IMMOBILIZED POLYMERS UTILIZING MICROFLUORESCENCE DETECTION

CROSS-REFERENCES TO RELATED APPLICATIONS

This Application is a continuation of U.S. application Ser. No. 11/325,809, filed Jan. 5, 2006, which is a continuation of U.S. application Ser. No. 10/996,692, filed Nov. 23, 2004, which is a continuation of U.S. application Ser. No. 10/077, 070, filed Feb. 14, 2002, which is a continuation of U.S. application Ser. No. 08/829,893, filed Apr. 2, 1997, now abandoned, which is a continuation of U.S. application Ser. No. 08/679,478, filed Jul. 12, 1996, now U.S. Pat. No. 5,902,723, which is a continuation of U.S. application Ser. No. 07/626, 730, filed Dec. 6, 1990, now U.S. Pat. No. 5,547,839, the entire disclosures of which are incorporated herein by reference.

BACKGROUND OF THE INVENTION

The present invention relates to the determination of the sequences of polymers immobilized to a substrate. In particular, one embodiment of the invention provides a method and apparatus for sequencing many nucleic acid sequences immobilized at distinct locations on a matrix surface. The principles and apparatus of the present invention may be used, for example, also in the determination of sequences of peptides, polypeptides, oligonucleotides, nucleic acids, oligosaccharides, phospholipids and other biological polymers. It is especially useful for determining the sequences of nucleic acids and proteins.

The structure and function of biological molecules are closely interrelated. The structure of a biological polymer, typically a macromolecule, is generally determined by its monomer sequence. For this reason, biochemists historically have been interested in the sequence characterization of biological macromolecule polymers. With the advent of molecular biology, the relationship between a protein sequence and its corresponding encoding gene sequence is well understood. Thus, characterization of the sequence of a nucleic acid encoding a protein has become very important.

Partly for this reason, the development of technologies providing the capability for sequencing enormous amounts of DNA has received great interest. Technologies for this capability are necessary for, for example, the successful completion of the human genome sequencing project. Structural characterization of biopolymers is very important for further progress in many areas of molecular and cell biology.

While sequencing of macromolecules has become extremely important, many aspects of these technologies have not advanced significantly over the past decade. For example, in the protein sequencing technologies being applied today the Edman degradation methods are still being used. See, e.g., Knight (1989) "Microsequencers for Proteins and Oligosaccharides," *Bio/Technol.* 7:1075 1076. Although advanced instrumentation for protein sequencing has been developed, see, e.g., Frank et al. (1989) "Automation of DNA Sequencing Reactions and Related Techniques: A Work Station for Micromanipulation of Liquids," *Bio/Technol.* 6:1211-1213, this technology utilizes a homogeneous and isolated protein sample for determination of removed residues from that homogeneous sample.

Likewise, in nucleic acid sequencing technology, three major methods for sequencing have been developed, of which two are commonly used today. See, e.g., Sambrook et al. (1989) *Molecular Cloning: A Laboratory Manual* (2d Ed.) Vols. 13, Cold Spring Harbor Press, New York, which is hereby incorporated herein by reference. The first method was developed by Maxam and Gilbert. See, e.g., Maxam and Gilbert (1980) "Sequencing End-Labeled DNA with Base-Specific Chemical Cleavages," *Methods in Enzymol.* 65:499-560, which is hereby incorporated herein by reference. The polymer is chemically cleaved with a series of base-specific cleavage reagents thereby generating a series of fragments of various lengths. The various fragments, each resulting from a cleavage at a specific base, are run in parallel on a slab gel which resolves nucleic acids which differ in length by single nucleotides. A specific label allows detection of cleavages at all nucleotides relative to the position of the label.

This separation requires high resolution electrophoresis or some other system for separating nucleic acids of very similar size. Thus, the target nucleic acid to be sequenced must usually be initially purified to near homogeneity.

Sanger and Coulson devised two alternative methods for nucleic acid sequencing. The first method, known as the plus and minus method, is described in Sanger and Coulson (1975) *J. Mol. Biol.* 94:441-448, and has been replaced by the second method. Subsequently, Sanger and Coulson developed another improved sequencing method known as the dideoxy chain termination method. See, e.g., Sanger et al. (1977) "DNA Sequencing with Chain-Termination Inhibitors," *Proc. Natl. Acad. Sci. USA* 74:5463-5467, which is hereby incorporated herein by reference. This method is based on the inability of 2',3' dideoxy nucleotides to be elongated by a polymerase because of the absence of a 3' hydroxyl group on the sugar ring, thus resulting in chain termination. Each of the separate chain terminating nucleotides are incorporated by a DNA polymerase, and the resulting terminated fragment is known to end with the corresponding dideoxy nucleotide. However, both of the Sanger and Coulson sequencing techniques usually require isolation and purification of the nucleic acid to be sequenced and separation of nucleic acid molecules differing in length by single nucleotides.

Both the polypeptide sequencing technology and the oligonucleotide sequencing technologies described above suffer from the requirement to isolate and work with distinct homogeneous molecules in each determination.

In the polypeptide technology, the terminal amino acid is sequentially removed and analyzed. However, the analysis is dependent upon only one single amino acid being removed, thus requiring the polypeptide to be homogeneous.

In the case of nucleic acid sequencing, the present techniques typically utilize very high resolution polyacrylamide gel electrophoresis. This high resolution separation uses both highly toxic acrylamide for the separation of the resulting molecules and usually very high voltages in running the electrophoresis. Both the purification and isolation techniques are highly tedious, time consuming and expensive processes.

Thus, a need exists for the capability of simultaneously sequencing many biological polymers without individual isolation and purification. Moreover, dispensing with the need to individually perform the high resolution separation of related molecules leads to greater safety, speed, and reliability. The present invention solves these and many other problems.

BRIEF SUMMARY OF THE INVENTION

The present invention provides the means to sequence hundreds, thousands or even millions of biological macromolecules simultaneously and without individually isolating each macromolecule to be sequenced. It also dispenses with the requirement, in the case of nucleic acids, of separating the products of the sequencing reactions on dangerous polyacrylamide gels. Adaptable to automation, the cost and effort required in sequence analysis will be dramatically reduced.

This invention is most applicable, but not limited, to linear macromolecules. It also provides specific reagents for sequencing both oligonucleotides and polypeptides. It provides an apparatus for automating the processes described herein.

The present invention provides methods for determining the positions of polymers which terminate with a given monomer, where said polymers are attached to a surface having a plurality of positionally distinct polymers attached thereto, said method comprising the steps of:
  labeling a terminal monomer in a monomer type specific manner; and
  scanning said surface, thereby determining the positions of said label.

In one embodiment, the polymers are polynucleotides, and usually the labeling of the terminal marker comprises incorporation of a labeled terminal monomer selected from the group of nucleotides consisting of adenine, cytidine, guanidine and thymidine.

An alternative embodiment provides methods for concurrently determining which subset of a plurality of positionally distinct polymers attached to a solid substrate at separable locations terminates with a given terminal subunit, said method comprising the steps of:
  mixing said solid substrate with a solution comprising a reagent, which selectively marks positionally distinct polymers which terminate with said given terminal subunit; and
  determining with a detector which separable locations are marked, thereby determining which subset of said positionally distinct polymers terminated with said given terminal subunit.

In one version, the solution comprises a reagent which marks the positionally distinct polymer with a fluorescent label moiety. In another version the terminal subunit is selected from the group consisting of adenosine, cytosine, guanosine, and thymine.

Methods are also provided for determining which subset of a plurality of primer polynucleotides have a predetermined oligonucleotide, wherein the polynucleotides are complementary to distinctly positioned template strands which are attached to a solid substrate, said method comprising the steps of:
  selectively marking said subset of primer polynucleotides having the predetermined oligonucleotide; and
  detecting which polynucleotides are marked.

In one embodiment, the oligonucleotide subunit is a single nucleotide; in another the marking comprises elongating said primer with a labeled nucleotide which is complementary to a template; and in a further embodiment the marking step uses a polymerase and a blocked and labeled adenine.

The invention embraces methods for concurrently obtaining sequence information on a plurality of polynucleotides by use of a single label detector, said method comprising the steps of:
  attaching a plurality of positionally distinct polynucleotides to a solid substrate at separable locations;
  labeling said plurality of polynucleotides with a terminal nucleotide specific reagent, said label being detectable using said label detector; and
  determining whether said specific labeling reagent has labeled each separable location.

Often, the labeling is performed with reagents which can distinguishably label alternative possible nucleotide monomers. One embodiment uses four replica substrates each of which is labeled with a specific labeling reagent for adenine, cytosine, guanine, or thymine. Usually, the labeling and determining steps are performed in succession using reagents specific for each of adenine, cytosine, guanine, and thymine monomers.

An alternative embodiment provides methods for concurrently obtaining sequence information on a plurality of polynucleotides, said method comprising the steps of:
  attaching distinct polynucleotides to a plurality of distinct solid substrates;
  labeling said plurality of solid substrates with a terminal nucleotide specific labeling reagent; and
  determining whether said specific labeling reagent has labeled each distinct substrate.

The method can be performed using a continuous flow of distinct solid substrates through a reaction solution.

A method is provided for simultaneously sequencing a plurality of polymers made up of monomer units, said plurality of polymers attached to a substrate at definable positions, said method comprising the steps of:
  mixing said substrate with a reagent which specifically recognizes a terminal monomer, thereby providing identification among various terminal monomer units;
  scanning said substrate to distinguish signals at definable positions on said substrate; and
  correlating said signals at defined positions on said substrate to provide sequential series of sequence determinations.

Often, the plurality of polymers are synthesized by a plurality of separate cell colonies, and the polymers may be attached to said substrate by a carbonyl linkage. In one embodiment, the polymers are polynucleotides, and often the substrate comprises silicon. The scanning will often identify a fluorescent label. In one embodiment, the reagent exhibits specificity of removal of terminal monomers, in another, the reagent exhibits specificity of labeling of terminal monomers.

The invention also embraces methods for sequencing a plurality of distinctly positioned polynucleotides attached to a solid substrate comprising the steps of:
  hybridizing complementary primers to said plurality of polynucleotides;
  elongating a complementary primer hybridized to a polynucleotide by adding a single nucleotide; and
  identifying which of said complementary primers have incorporated said nucleotide. In some versions, the elongating step is performed simultaneously on said plurality of polynucleotides linked to said substrate.

Typically, the substrate is a two dimensional surface and the identifying results from a positional determination of the complementary primers incorporating the single defined nucleotide. A silicon substrate is useful in this method.

Methods, are provided where the linking is by photocrosslinking polynucleotide to said complementary primer, where said primer is attached to said substrate. The elongating will be often catalyzed by a DNA dependent polymerase. In various embodiments, a nucleotide will have a removable blocking moiety to prevent further elongation, e.g., NVOC.

A nucleotide with both a blocking moiety and labeling moiety will be often used.

A further understanding of the nature and advantages of the invention herein may be realized by reference to the remaining portions of the specification and the attached drawings.

BRIEF DESCRIPTION OF THE DRAWINGS

FIG. 8A illustrates schematically, at a molecular level, the sequence of events which occur during a particular sequencing cycle. FIG. 8B illustrates, in a logic flow chart, how the scheme is performed.

FIG. 10A illustrates schematically, at a molecular level, the sequence of events which occur during a particular sequencing cycle. FIG. 10B illustrates in a logic flow chart how the scheme is performed.

DETAILED DESCRIPTION OF THE INVENTION

Figure 1:
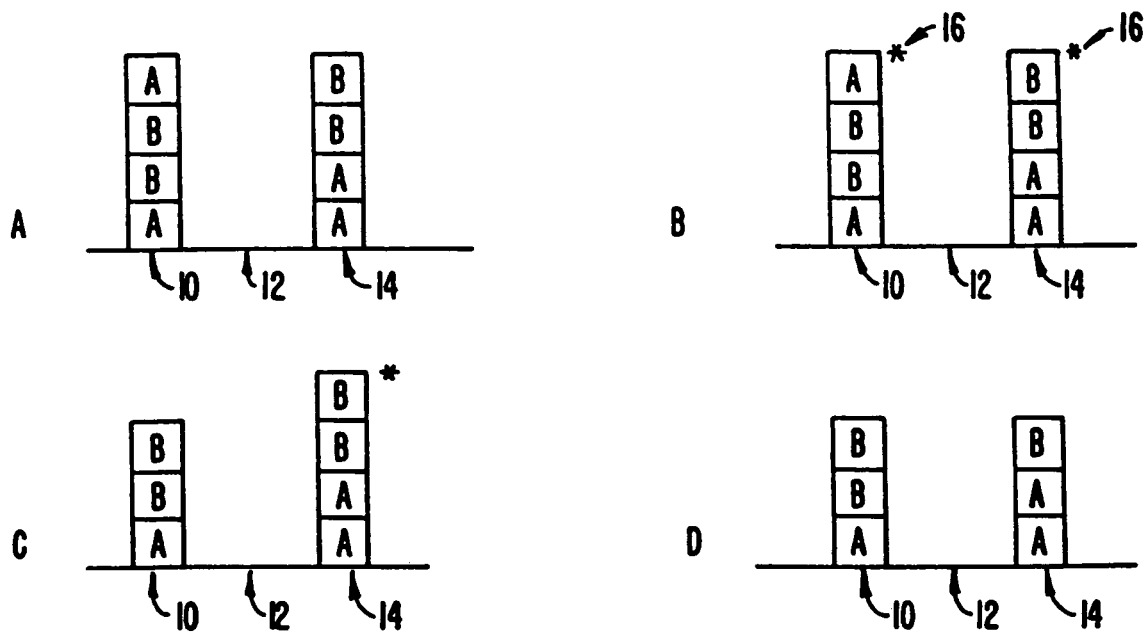
FIG. 1 illustrates a simplified and schematized embodiment of a degradative scheme for polymer sequencing.

I. Sequencing Procedure for a Generic Polymer
  A. Overview
    1. Substrate and matrix
    2. Scanning system
    3. Synthetic/degradative cycles
    4. Label
    5. Utility
  B. Substrate/Matrix
    1. Non-distortable
    2. Attachment of polymer
  C. Scanning system
    1. Mapping to distinct position
    2. Detection system
    3. Digital or analog signal
  D. Synthetic or degradative cycle
    1. Synthetic cycles
      a. synthetic scheme
      b. blocking groups
    2. Degradative cycles
    3. Conceptual principles
  E. Label
    1. Attachment
    2. Mode of detection
  F. Utility
II. Specific Embodiments
  A. Synthetic method
  B. Chain degradation method
III. Apparatus I. Sequencing Procedure for a Generic Polymer The present invention provides methods and apparatus for the preparation and use of a substrate having a plurality of polymers with various sequences where each small defined contiguous area defines a small cluster of homogeneous polymer sequences. The invention is described herein primarily with regard to the sequencing of nucleic acids but may be readily adapted to the sequencing of other polymers, typically linear biological macromolecules. Such polymers include, for example, both linear and cyclical polymers or nucleic acids, polysaccharides, phospholipids, and peptides having various different amino acids, heteropolymers in which the polymers are mixed, polyurethanes, polyesters, polycarbonates, polyureas, polyamides, polyethyleneimines, polyarylene sulfides, polysiloxanes, polyimides, polyacetates or mixed polymers of various sorts. In a preferred embodiment, the present invention is described in the use of sequencing nucleic acids.

Various aspects of U.S. Ser. No. 07/362,901 (VLSIPS parent); U.S. Ser. No. 07/492,462, now U.S. Pat. No. 5,143,854 (VLSIPS CIP); U.S. Ser. No. 07/435,316 (caged biotin parent); U.S. Ser. No. 07/612,671 (caged biotin CIP); and simultaneously filed cases U.S. Ser. No. 07/624,114 (sequencing by hybridization) and U.S. Ser. No. 07/624,120, a divisional of which has issued as U.S. Pat. No. 5,744,305 (automated VLSIPS), each of which is incorporated herein by reference, are applicable to the substrates and matrix materials described herein, to the apparatus used for scanning the matrix arrays, to means for automating the scanning process, and to the linkage of polymers to a substrate.

By use of masking technology and photosensitive synthetic subunits, the VLSIPS apparatus allows for the stepwise synthesis of polymers according to a positionally defined matrix pattern. Each oligonucleotide probe will be synthesized at known and defined positional locations on the substrate. This forms a matrix pattern of known relationship between position and specificity of interaction. The VLSIPS technology allows the production of a very large number of different oligonucleotide probes to be simultaneously and automatically synthesized including numbers in excess of about $10^2$, $10^3$, $10^4$, $10^5$, $10^6$, or even more, and at densities of at least about $10^2$, $10^3/cm^2$, $10^4/cm^2$, $10^5/cm^2$ and up to $10^6/cm^2$ or more. This application discloses methods for synthesizing polymers on a silicon or other suitably derivatized substrate, methods and chemistry for synthesizing specific types of biological polymers on those substrates, apparatus for scanning and detecting whether interaction has occurred at specific locations on the substrate, and various other technologies related to the use of a high density very large scale immobilized polymer substrate. At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides. Region size is sufficiently small to correspond to densities of at least about 5 regions/$cm^2$, 20 regions/$cm^2$, 50 regions/$cm^2$, 100 regions/$cm^2$, and greater, including 300 regions/$cm^2$, 1000 regions/$cm^2$, 3K regions/$cm^2$, 10K regions/$cm^2$, 30K regions/$cm^2$, 100K regions/$cm^2$, 300K regions/$cm^2$ or more, even in excess of one million regions/$cm^2$.

A. Overview

The present invention is based, in part, on the ability to perform a step wise series of reactions which either extend or degrade a polymer by defined units.

FIG. 1 schematizes a simplified linear two monomer polymer made up of A type and B type subunits. A degradative scheme is illustrated. Panel A depicts a matrix with two different polymers located at positions 10 and 14, but with no polymer linked at position 12. A reaction is employed to label all of these polymers at the terminus opposite the attachment of the monomer. Panel B illustrates a label (designated by an asterisk) incorporated at position 16 on the terminal monomers. A scan step is performed to locate positions 10 and 14 where polymers have been linked, but no polymer is located at position 12. The entire matrix is exposed to a reagent which is specific for removing single terminal A monomers, which are also labeled. The reagent is selected to remove only a single monomer; it will not remove further A monomers. Removal of the labeled A monomer leaves a substrate as illustrated in panel C. A scan step is performed and compared with the previous scan, indicating that the polymer located at position 12 has lost its label, i.e., that polymer at 12 terminated with an A monomer. The entire matrix is then exposed to a second reagent which is specific for removing terminal B monomers which are also labeled. Note that only a single B on each monomer is removed and that successive B monomers are not affected. Removal of the labeled B monomer leaves a substrate as illustrated in panel D. Another scan step is performed, indicating that the polymer located at position 14 has lost its label, i.e., it terminated with a B monomer. The sequence of treatments and scans is repeated to determine the successive monomers. It will be recognized that if the labeled A and B are distinguishable, i.e., the label on polymers at sites 10 and 14 may be distinguished, a single removal step can be performed to convert the substrate as illustrated in panel B directly to that illustrated in panel D.

An alternative embodiment employs synthetic reactions where a synthetic product is made at the direction of the attached polymer. The method is useful in the synthesis of a complementary nucleic acid strand by elongation of a primer as directed by the attached polymer.

Figure 2:
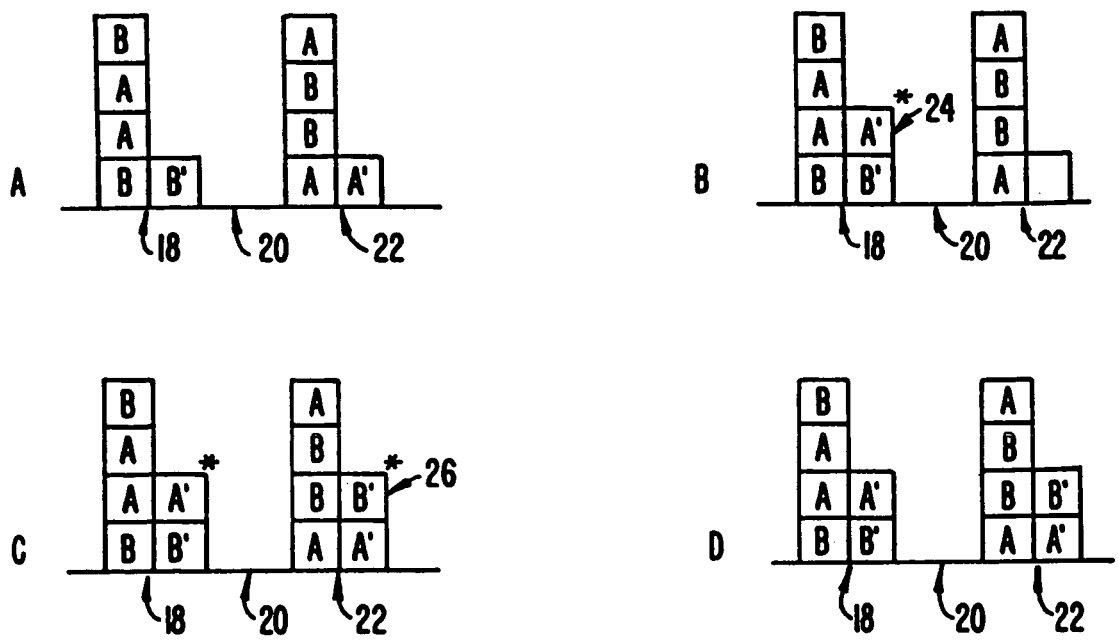
FIG. 2 illustrates a simplified and schematized embodiment of a synthetic scheme for polymer sequencing.

FIG. 2 illustrates a similar simplified polymer scheme, where the A and B monomer provide a complementary correspondence to A' and B' respectively. Thus, an A monomer directs synthetic addition of an A' monomer and a B monomer directs synthetic addition of a B' monomer. Panel A depicts monomers attached at locations 18 and 22, but not at location 20. Each polymer already has one corresponding complementary monomer A'. The matrix, with polymers, is subjected to an elongation reaction which incorporates, e.g., single labeled A' monomers 24 but not B' monomers, as depicted in panel B. The label is indicated by the asterisk. Note that only one A monomer is added. A scan step is performed to determine whether polymers located at positions 18 or 22 have incorporated the labeled A' monomers. The polymer at position 18 has, while the polymer at position 22 has not. Another elongation reaction which incorporates labeled B' monomers 26 is performed resulting in a matrix as depicted in panel C. Again note that only one, and not successive B' monomers, is added. Another scan is performed to determine whether a polymer located at sites 18 or 22 has incorporated a labeled B' monomer, and the result indicates that the polymer located at site 22 has incorporated the labeled B' monomer. A next step removes all of the labels to provide a substrate as depicted in panel D. As before, if the polymer which incorporated a labeled A' monomer is distinguishable from a polymer which incorporated a labeled B' monomer, the separate elongation reactions may be combined producing a panel C type matrix directly from a panel A type matrix and the scan procedure can distinguish which terminal monomer was incorporated.

It will be appreciated that the process may be applied to more complicated polymers having more different types of monomers. Also, the number of scan steps can be minimized if the various possible labeled monomers can be differentiated by the detector system.

Typically, the units will be single monomers, though under certain circumstances the units may comprise dimers, trimers, or longer segments of defined length. In fact, under certain circumstances, the method may be operable in removing or adding different sized units so long as the units are distinguishable. However, it is very important that the reagents used do not remove or add successive monomers. This is achieved in the degradative method by use of highly specific reagents. In the synthetic mode, this is often achieved with removable blocking groups which prevent further elongation.

Figure 3:
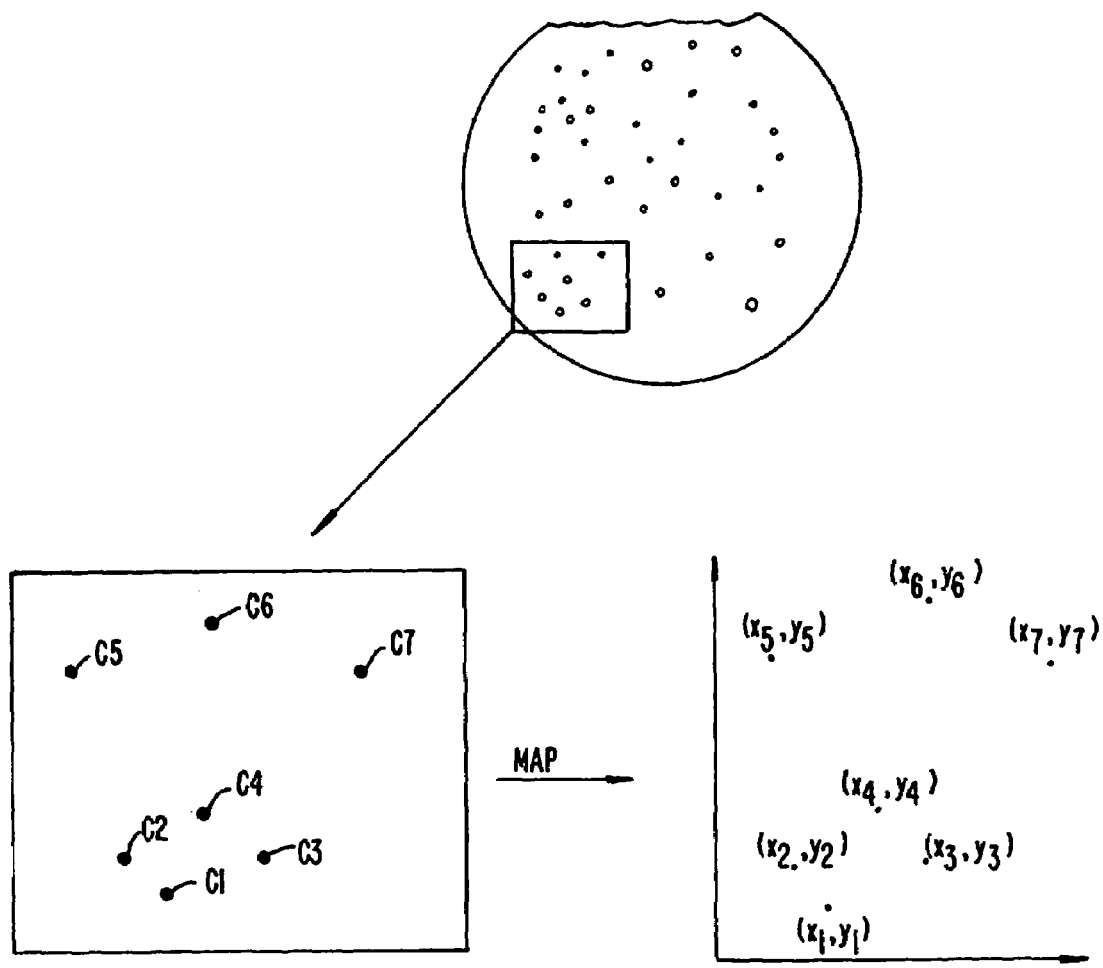
FIG. 3 illustrates a coordinate mapping system of a petri plate containing colonies. Each position of a colony can be assigned a distinct coordinate position.

One important aspect of the invention is the concept of using a substrate having homogeneous clusters of polymers attached at distinct matrix positions. The term "cluster" refers to a localized group of substantially homogeneous polymers which are positionally defined as corresponding to a single sequence. For example, a coordinate system will allow the reproducible identification and correlation of data corresponding to distinct homogeneous clusters of polymers locally attached to a matrix surface. FIG. 3 illustrates a mapping system providing such a correspondence, where transfer of polymers produced by a colony of organisms to a matrix preserves spatial information thereby allowing positional identification. The positional identification allows correlation of data from successive scan steps.

In one embodiment, bacterial colonies producing polymers are spatially separated on the media surface of a petri plate as depicted in panel A. Alternatively, phage plaques on a bacterial lawn can exhibit a similar distribution. A portion of panel A is enlarged and shown in panel B. Individual colonies are labeled C1-C7. The position of each colony can be mapped to positions on a coordinate system, as depicted in panel C. The positions of each colony can then be defined, as in a table shown in panel D, which allows reproducible correlation of scan cycle results.

Although the preferred embodiments are described with respect to a flat matrix, the invention may also be applied using the means for correlating detection results from multiple samples after passage through batch or continuous flow reactions. For example, spatially separated polymers may be held in separate wells on a microtiter plate. The polymers will be attached to a substrate to retain the polymers as the sequencing reagents are applied and removed.

The entire substrate surface, with homogeneous clusters of polymers attached at defined positions, may be subjected to batch reactions so the entire surface is exposed to a uniform and defined sequence of reactions. As a result, each cluster of target polymers for sequencing will be subjected to similar reactive chemistry. By monitoring the results of these reactions on each cluster localized to a defined coordinate position, the sequence of the polymer which is attached at that site will be determined.

Figure 4:
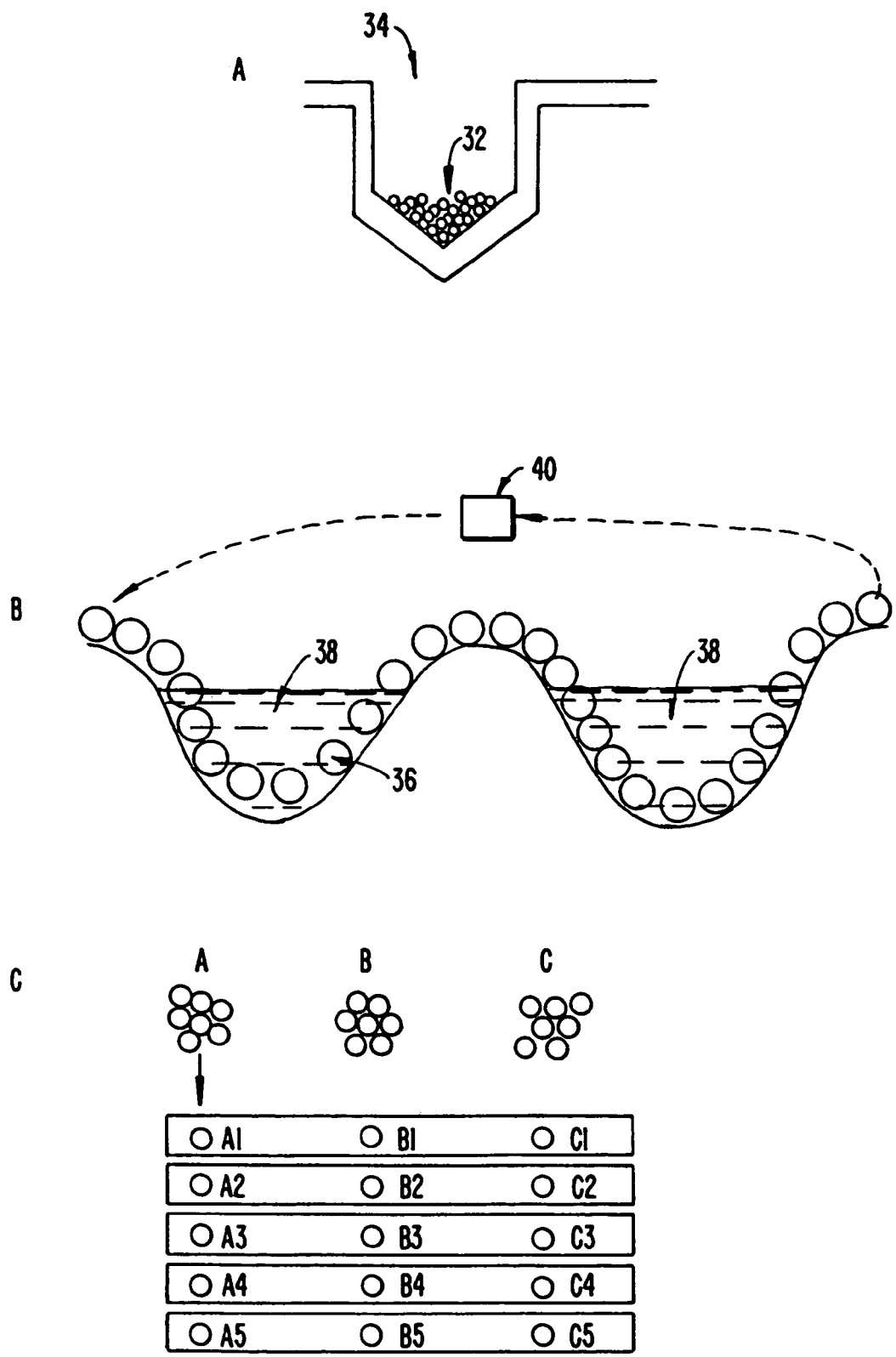
FIG. 4 illustrates various modified embodiments of the substrates.

FIG. 4, panel A illustrates solid phase attached polymers linked to particles 32 which are individually sequestered in separate wells 34 on a microtiter plate. The scanning system will separately scan each well. FIG. 4 panel B illustrates marbles 36 to which polymers are attached. The marbles are automatically fed in a continuous stream through the reaction reagents 38 and past a detector 40. The marbles may be carefully held in tubes or troughs which prevent the order of the beads from being disturbed. In a combination of the two embodiments, each polymer is attached to a plurality of small marbles, and marbles having each polymer are separated, but retained in a known order. Each marble is, in batch with a number of analogous marbles having other polymers linked individually to them, passed through a series of reagents in the sequencing system. For example, A2, B2, and C2 are subjected to sequencing reactions in batch, with label incorporated only for the second monomer. A3, B3, and C3 are likewise treated to determine the third monomer. Likewise for $A_n$, $B_n$, and $C_n$. However, within each batch, the detection will usually occur in the order A, B, and C, thereby providing for correlation of successive detection steps for the A polymer beads, for the B polymer beads, and for the C polymer beads.

Figure 5:
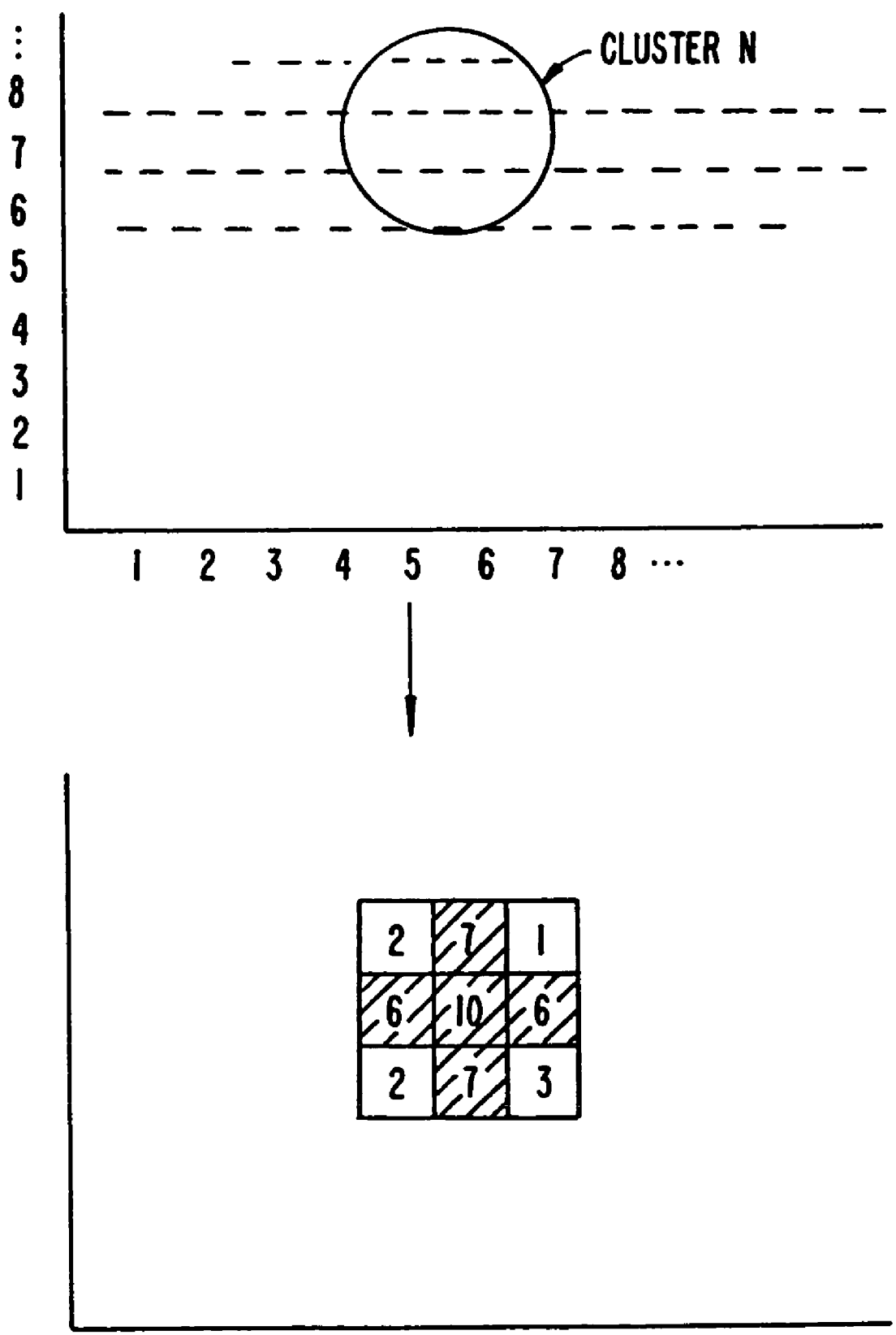
FIG. 5 illustrates an idealized scanning result corresponding to a particular colony position.

FIG. 5 illustrates a signal which might result from a particular defined position. Panel A illustrates the position of a given colony relative to the positions corresponding to the positional map. The scan system will typically determine the amount of signal, or type of signal, at each position of the matrix. The scan system will adjust the relationship of the detector and the substrate to scan the matrix in a controllable fashion. An optical system with mirrors or other elements may allow the relative positions of the substrate and detection to be fixed. The scanner can be programmed to scan the entire substrate surface in a reproducible manner, or to scan only those positions where polymer clusters have been localized. A digital data map, panel B, can be generated from the scan step.

Thus, instead of subjecting each individual and separated polymer to the series of reactions as a homogeneous sample, a whole matrix array of different polymers targeted for sequencing may be exposed to a series of chemical manipulations in a batch format. A large array of hundreds, thousands, or even millions of spatially separated homogeneous regions may be simultaneously treated by defined sequencing chemistry.

The use of a coordinate system which can reproducibly assay a defined position after each reaction cycle can be advantageously applied according to this invention. For example, a colony plaque lift of polymers can be transferred onto a nitrocellulose filter or other substrate. A scanning detector system will be able to reproducibly monitor the results of chemical reactions performed on the target polymers located at the defined locations of particular clones. An accurate positioning can be further ensured by incorporating various alignment marks on the substrate.

The use of a high resolution system for monitoring the results of successive sequencing steps provides the possibility for correlating the scan results of each successive sequencing reaction at each defined position.

The invention is dependent, in part, upon the stepwise synthesis or degradation of the localized polymers as schematized in FIGS. 1 and 2. The synthetic scheme is particularly useful on nucleic acids which can be synthesized from a complementary strand. Otherwise, a stepwise degradation scheme may be the preferred method. Although single monomer cycles of synthesis or degradation will usually be applicable, in certain cases the technology will be workable using larger segments, e.g., dimers or trimers, in the cyclic reactions.

The present invention also provides methods for production or selection of monomer-specific degradative reagents based upon catalytic antibody constructs. Antibody binding sites exhibiting specificity for binding particular terminal monomers can be linked to cleavage reagents or active sites of cleavage enzymes. Thus, reagents which are specific for particular terminal nucleotides may function to remove them in a specific fashion.

The invention also makes use of a means for detecting or labeling the polymers. Particular sequencing chemistry can be selected for specificity in reacting with terminal monomer units. Alternatively, indirect labeling methods may be applied which can distinguish between different terminal monomers. Another alternative scheme allows for terminal labeling which is not monomer-specific, but with the determination of the monomer based upon specificity of post-label reagents or upon monomer-distinguishable labels. Suitable such reagents will be antibodies or other reagents having specificity for distinguishing between different labeled terminal monomer residues and cleaving only those labeled monomer residues.

Thus, although neither the reaction nor the label need necessarily be specific, at least one of the pair must be specific. A comparison of label signal before and after a reaction allows determination of the change in label signal after monomer specific reactions are performed, and thereby provides the means to deduce the identity of the monomer at a given position.

B. Substrate/Matrix

The substrate or matrix has relatively few constraints on its composition. Preferably, the matrix will be inert to the sequencing reactions to which the polymers attached thereto will be subjected. Typically, a silicon or glass substrate will be used, but other suitable matrix materials include ceramics, or plastics, e.g., polycarbonate, polystyrene, delrin, and cellulose, and any other matrix which satisfies these functional constraints.

In one embodiment, the matrix should be sufficiently non-deformable that the scanning system can reproducibly scan the matrix and reliably correlate defined positions with earlier and later scan operations. However, by including alignment markings on the substrate, the need for absolute rigidity of the substrate may be reduced.

In an alternative embodiment, the matrix may merely be large enough that the attached polymer may be separated from a liquid phase containing the sequencing reagents. In this embodiment, a single detection unit is used to analyze the label in a multiplicity of different samples after each of the reaction steps. Thus, different samples may be separably treated in distinct wells of a microtiter dish.

Separate homogeneous polymers can be introduced to solid phase beads in each microtiter well. Sequencing reagents may be individually introduced separately into each well, or transferred from well to well with the polymers remaining in the correct well due to their solid phase attachments.

In an alternative approach, the solid phase matrix may be marbles or other particularly shaped articles. Spherical shapes, solid or hollow, are preferred because they can be easily transported through troughs or tubing which retains their relative orders. By feeding a succession of beads through appropriate reaction baths and past a detector in a known and retained order, a succession of label detection results from a bead may be correlated and converted into a polymer sequence.

The attachment of the target homogeneous clusters of target polymers to the substrate can be achieved by appropriate linkage chemistry. As indicated before, the linkage should be stable and insensitive to the sequencing reagents used. The specific linkages will depend, of course, upon the particular combination of substrate and polymer being used.

Typically, the most useful chemical moieties which will be used are amines. Typical substrate derivatized groups include aminopropyl triethoxysilane, hydroxypropylacylate, or hydroxy reagents, see, e.g., U.S. Ser. No. 07/624,120 (automated VLSIPS). Typical polymer derivatized groups include nitroveratryl and nitroveratryl oxycarbonyl. Linkage types are also illustrated and detailed in U.S. Ser. No. 07/624,120 (automated VLSIPS) and U.S. Ser. No. 07/624,114 (sequencing by hybridization).

Figure 6:
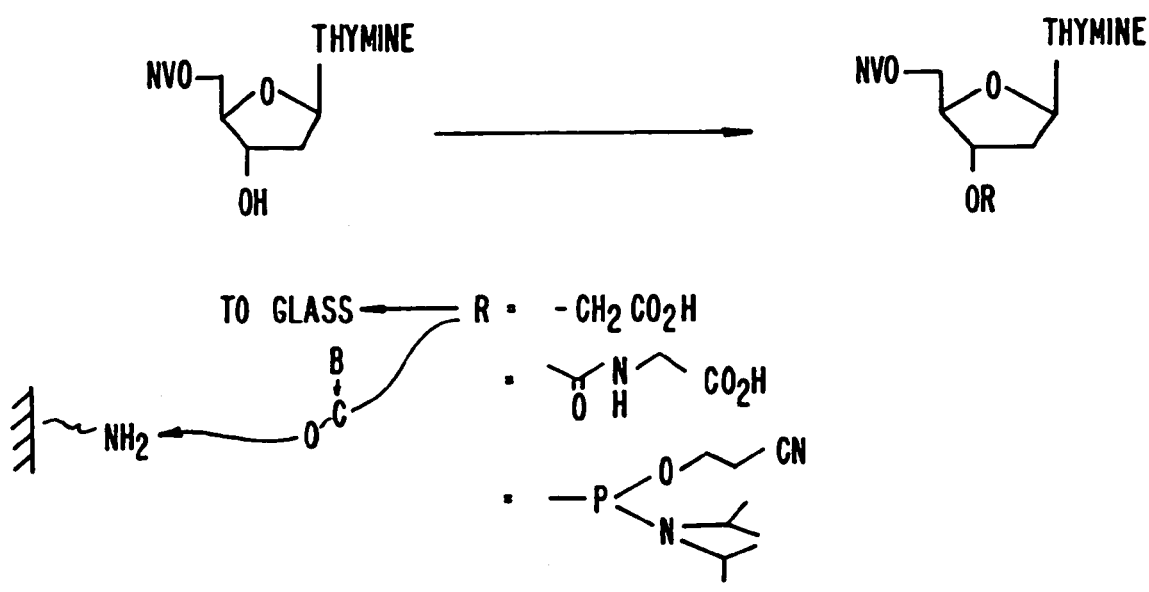
FIG. 6 illustrates particular linkers useful for attaching a nucleic acid to a silicon substrate. Note that thymine may be, substituted by adenine, cytidine, guanine, or uracil.

FIG. 6 illustrates one preferred linkage chemistry for nucleic acids. An NVO-derivatized nucleotide is made as described in U.S. Ser. No. 07/624,120 (automated VLSIPS). The specific conditions for synthesis of thymidine are described therein and are adaptable to other nucleotides and nucleosides. The nucleoside analog is further derivatized with an appropriate R group at the 3' hydroxyl. Preferred R groups are indicated in FIG. 6. The linkage produces a photosensitive blocked nucleoside suitable for phosphoramidite synthesis of further polynucleotides which can serve as a complementary strand for hybridization of other polymers. The hybrids of the complementary strands may be covalently crosslinked using acridine dyes or other intercalative reagents, e.g., psoralen. See, e.g., Kornberg (1980) DNA Replication Freeman, San Francisco; Wiesehahn, et al. (1978) *Proc. Natl. Acad. Sci. USA* 75:2703-2707, and Sheldon (1986) U.S. Pat. No. 4,582,789 which are each incorporated herein by reference.

The linkage should be substantially inert to the cyclic sequencing reactions and scan cycles. Usually, the linkage will be at a defined and homogeneous polymer position, preferably at the end opposite where the sequencing chemistry takes place. Although the type of linkage is dependent upon the polymer being sequenced, various types of polymers have preferred linkages. For polypeptides, amino terminal or carboxyl terminal linkages will be preferred. Specific amino terminal linkages include amino butyric acid, amino caproic acids, and similar carboxylic acids. Specific carboxyl terminal linkages include butyric acid, caproic acid, and other carboxylic acids, hydrocarbon, and ethers. See now abandoned U.S. Ser. No. 07,435,316, filed Nov. 13, 1989 (VLSIPS parent), and U.S. Ser. No. 07/492,462, filed Mar. 7, 1990, now U.S. Pat. No. 5,143,854 (VLSIPS CIP), which are incorporated herein by reference. For nucleic acids, the linkages will typically be either 5' or 3' linkages. Suitable 3' linkages include those illustrated in FIG. 6, and others described in U.S. Ser. No. 07/624,114 (sequencing by hybridization).

Alternatively, for complementary polymers, particularly nucleic acids, linkage may be via crosslinkage of the complementary polymers where the complementary strand is directly attached to the matrix. Acridine dyes, e.g., psoralen, or a similar crosslinking agent between the strands can be used. See, e.g., Dattagupta, et al., "Coupling of Nucleic Acids to Solid Support By Photochemical Methods," Ser. No. 4,713,326; and Ser. No. 4,542,102; and Chatteijee, M. et al. (1990) *J. Am. Chem. Soc.* 112:6397; which describe useful crosslinking reagents, and are hereby incorporated herein by reference.

For polynucleotides, the preferred attachment to the matrix is through a synthetic oligomer by the 5' end of each target sequence. This oligomer is designed to anneal to the desired target templates used in a synthetic system or to the polynucleotide used in the degradation approach. In one embodiment, a vector sequence which is complementary to the immobilized oligonucleotide is incorporated adjacent the cloning inserts, thereby providing a common complementary sequence for each insert. In particular, a cloning vector will be selected with a defined sequence adjacent the insert. See, e.g., Sambrook et al., (1989) *Molecular Cloning: A Laboratory Manual, Vols.* 1-3, Cold Spring Harbor Press, which is hereby incorporated herein by reference. This defined sequence is used, in some embodiments, as a common linker for all of the vector inserts. The inserts, adjacent to this linker, will be transferable by hybridization to the matrix linked complementary sequences. The hybrids are crosslinked by addition of a suitable crosslinker under appropriate conditions, for example, photocrosslinking by psoralen with uv light. See, e.g., Song et al. (1979) *Photochem. Photobiol.* 29:1177-1197; Cimino et al. (1985) *Ann. Rev. Biochem.* 54:1151-1193; and Parsons (1980) *Photochem. Photobiol.* 32:813-821; each of which is incorporated herein by reference. Using these approaches, the oligonucleotide linker serves as both the attachment linker and the polymerization primer.

FIG. 6 illustrates a preferred 3' terminal linkage designed for a phosphoramidite linkage of a synthetic primer and the reactions forming them. The chemical reactions for actually performing the linkage will be similar to those used for oligonucleotide synthesis instruments using phosphoramidite or similar chemistry. Applied Biosystems, Foster City, Calif. supplies oligonucleotide synthesizers.

C. Scanning System

The scanning system should be able to reproducibly scan the substrate. Where appropriate, e.g., for a two dimensional substrate where the polymers are localized to positions thereon, the scanning system should positionally define the clusters attached thereon to a reproducible coordinate system. It is important that the positional identification of clusters be repeatable in successive scan steps. Functionally, the system should be able to define physical positions to a coordinate system as described above and illustrated in FIGS. 3 and 4.

In alternative embodiments, the system can operate on a cruder level by separately detecting separate wells on a microtiter plate, or by scanning marbles which pass by the detector in an embodiment as described above and illustrated in FIG. 4.

The scanning system would be similar to those used in electrooptical scanning devices. See, e.g., the fluorescent detection device described in U.S. Ser. No. 07/492,462, now U.S. Pat. No. 5,143,854 (VLSIPS CIP), and U.S. Ser. No. 07/624,120 (automated VLSIPS). The system could exhibit many of the features of photographic scanners, digitizers or even compact disk reading devices. For example, a model no. PM500-A1x-y translation table manufactured by Newport Corporation can be attached to a detector unit. The x-y translation table is connected to and controlled by an appropriately programmed digital computer such as an IBM PC/AT or AT compatible computer. The detection system can be a model no. R943-02 photomultiplier tube manufactured by Hamamatsu, attached to a preamplifier, e.g., a model no. SR440 manufactured by Stanford Research Systems, and to a photon counter, e.g., an SR430 manufactured by Stanford Research System, or a multichannel detection device. Although a digital signal may usually be preferred, there may be circumstances where analog signals would be advantageous.

The stability and reproducibility of the positional localization in scanning will determine, to a large extent, the resolution for separating closely positioned polymer clusters in a 2 dimensional substrate embodiment. Since the successive monitoring at a given position depends upon the ability to map the results of a reaction cycle to its effect on a positionally mapped cluster of polymers, high resolution scanning is preferred. As the resolution increases, the upper limit to the number of possible polymers which may be sequenced on a single matrix will also increase. Crude scanning systems may resolve only on the order of 1000 µm, refined scanning systems may resolve on the order of 100 µm, more refined systems may resolve on the order of about 10 µm with optical magnification systems a resolution on the order of 1.0 µm is available, and more preferably a resolution on the order of better than 0.01 µm is desired. The limitations on the resolution may be diffraction limited and advantages may arise from using shorter wavelength radiation for the photo-optical deprotection fluorescent scanning steps. However, with increased resolution, the time required to fully scan a matrix will be increased and a compromise between speed and resolution will necessarily be selected. Parallel detection devices which will provide high resolution with shorter scan times will be applicable where multiple detectors will be moved in parallel.

With other embodiments, resolution often is not so important and sensitivity might be emphasized. However, the reliability of a signal may be pre-selected by counting photons and continuing to count for a longer period at positions where intensity of signal is lower. Although this will decrease scan speed, it can increase reliability of the signal determination. Various signal detection and processing algorithms may be incorporated into the detection system, such as described in U.S. Ser. No. 07/624,120 (activated VLSIPS). In one embodiment, the distribution of signal intensities of pixels across the region of signal are evaluated to determine whether the distribution of intensities corresponds to a time positive signal.

The detection system for the signal or label will depend upon the label used, which may be defined by the chemistry available. For optical signals, a combination of an optical fiber or charged couple device (CCD) may be used in the detection step. In those circumstances where the matrix is itself transparent to the radiation used, it is possible to have an incident light beam pass through the substrate with the detector located opposite the substrate from the polymers. For electromagnetic labels, various forms of spectroscopy systems can be used. Various physical orientations for the detection system are available and discussion of important design parameters is provided, e.g., in Jovin, *Adv. in Biochem. Bioplyms*, which is hereby incorporated herein by reference.

Various labels which are easily detected include radioactive labels, heavy metals, optically detectable labels, spectroscopic labels and the like. Various photoluminescent labels include those described in U.S. Ser. No. 624,114 (sequencing by hybridization). Protection and deprotection are described, e.g., in McCray, et al. (1989) *Ann. Rev. Biophysical Chemistry* 18:239-270, and U.S. Ser. No. 07/624,120 (automated VLSIPS), each of which is hereby incorporated herein by reference.

With a processing system, the speed of scanning may be dramatically increased with a system which only scans positions where known clusters of polymer are attached. This allows the scanning mechanism to skip over areas which have been determined to lack any polymer clusters and avoids loss of time in scanning useless regions of the matrix. Moreover, various problems with spurious or overlapping signals may be adjusted for by appropriate analysis.

Figure 7:
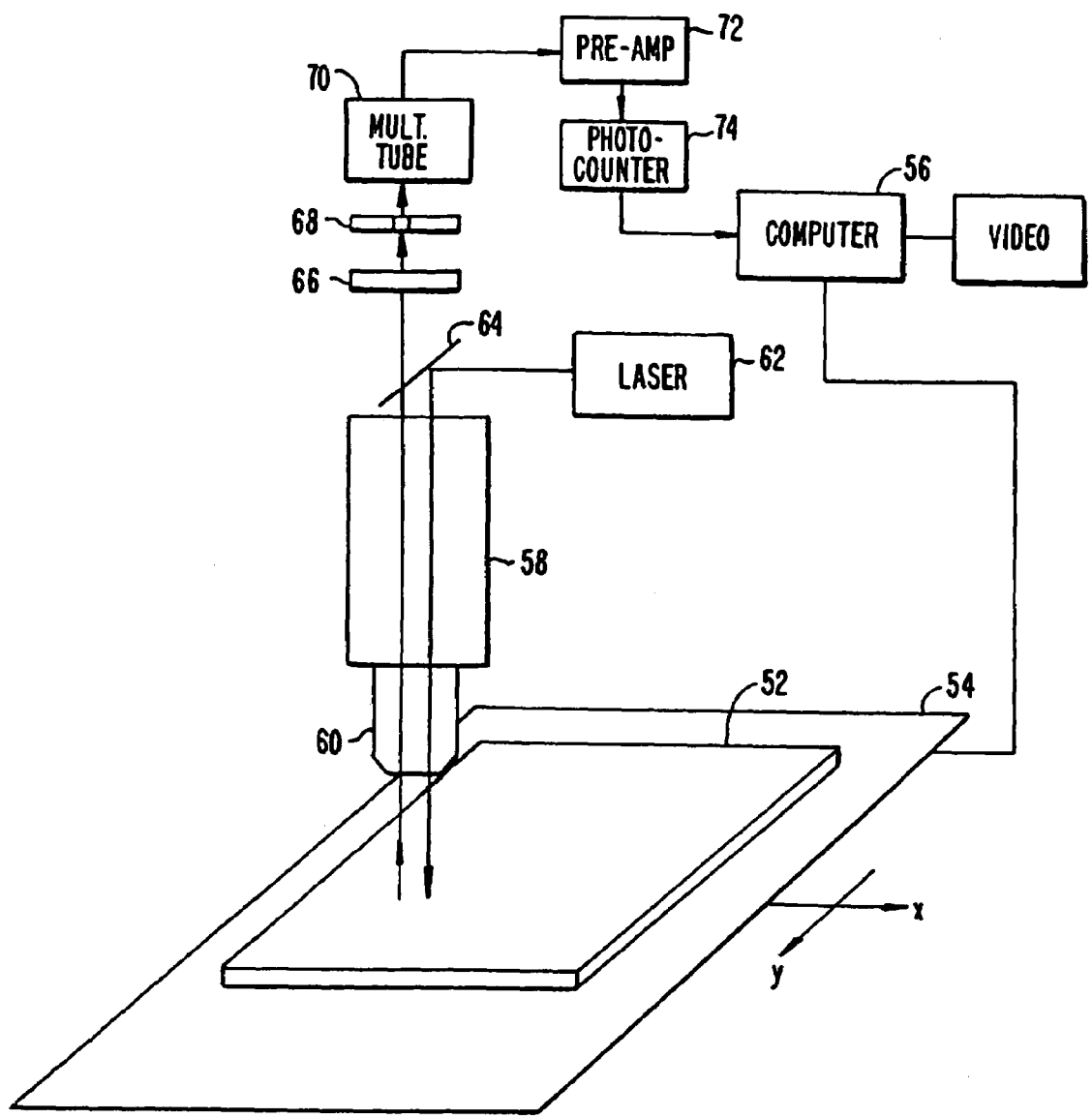
FIG. 7 illustrates an embodiment of the scanning system and reaction chamber.

A scanning apparatus which may be used for the presently described uses is schematically illustrated in FIG. 7. A substrate 52 is placed on an x-y translation table 54. In a preferred embodiment the x-y translation table is a model no. PM500-A1 manufactured by Newport Corporation. The x-y translation table is connected to and controlled by an appropriately programmed digital computer 56 which may be, for example, an appropriately programmed IBM PC/AT or AT compatible computer. Of course, other computer systems, special purpose hardware, or the like could readily be substituted for the AT computer used herein for illustration. Computer software for the translation and data collection functions described herein can be provided based on commercially available software including, for example, "Lab Windows" licensed by National Instruments, which is incorporated herein by reference for all purposes.

The substrate and x-y translation table are placed under a microscope 58 which includes one or more objectives 60. Light (about 488 nm) from a laser 62, which in some embodiments is a model no. 2020-05 argon ion laser manufactured by Spectraphysics, is directed at the substrate by a dichroic mirror 64 which passes greater than about 520 mn wavelength light but reflects 488 nm light. Dichroic mirror 64 may be, for example, a model no. FT510 manufactured by Carl Zeiss. Light reflected from the mirror then enters the microscope 58 which may be, for example, a model no. Axioscop 20 manufactured by Carl Zeiss. Fluorescein-marked materials on the substrate will fluoresce >488 nm light, and the fluoresced light will be collected by the microscope and passed through the mirror. The fluorescent light from the substrate is then directed through a wavelength filter 66 and, thereafter through an aperture plate 68. Wavelength filter 66 may be, for example, a model no. OG530 manufactured by Melles Griot and aperture plate 68 may be, for example, a model no. 477352/477380 manufactured by Carl Zeiss.

The fluoresced light then enters a photomultiplier tube 70 which in one embodiment is a model no. R943-02 manufactured by Hamamatsu, the signal is amplified in preamplifier 72 and photons are counted by photon counter 74. The number of photons is recorded as a function of the location in the computer 56. Pre-Amp 72 may be, for example, a model no. SR440 manufactured by Stanford Research Systems and photon counter 74 may be a model no. SR430 manufactured by Stanford Research Systems. The substrate is then moved to a subsequent location and the process is repeated. In preferred embodiments the data are acquired every 1 to 100 μm with a data collection diameter of about 0.8 to 10 μm preferred. In embodiments with sufficiently high fluorescence, a CCD detector with broadfield illumination is utilized.

By counting the number of photons generated in a given area in response to the laser, it is possible to determine where fluorescent marked molecules are located on the substrate. Consequently, for a substrate which has a matrix of polypeptides, for example, synthesized on the surface thereof, it is possible to determine which of the polypeptides has incorporated a fluorescently marked monomer.

According to preferred embodiments, the intensity and duration of the light applied to the substrate is controlled by varying the laser power and scan stage rate for improved signal-to-noise ratio by maximizing fluorescence emission and minimizing background noise. Signal analysis may improve the resolution and reliability of the system. The time of photon counting may be varied at various positions to provide high signal to background or noise.

D. Synthetic or Degradative Cycle

The present invention provides a substrate with positionally separated polymers for sequencing. The separation may be by solid phase carriers separated in separate wells, by separately manipulable carriers such as beads or marbles, or by physical separation of regions on a two-dimensional substrate surface. Each cluster region is a target for the sequencing reactions. Although the reactions are, in various embodiments, performed on all the clusters together, each cluster can be individually analyzed by following the results from the sequence of reactions on polymer clusters at positionally defined locations.

Figure 8:
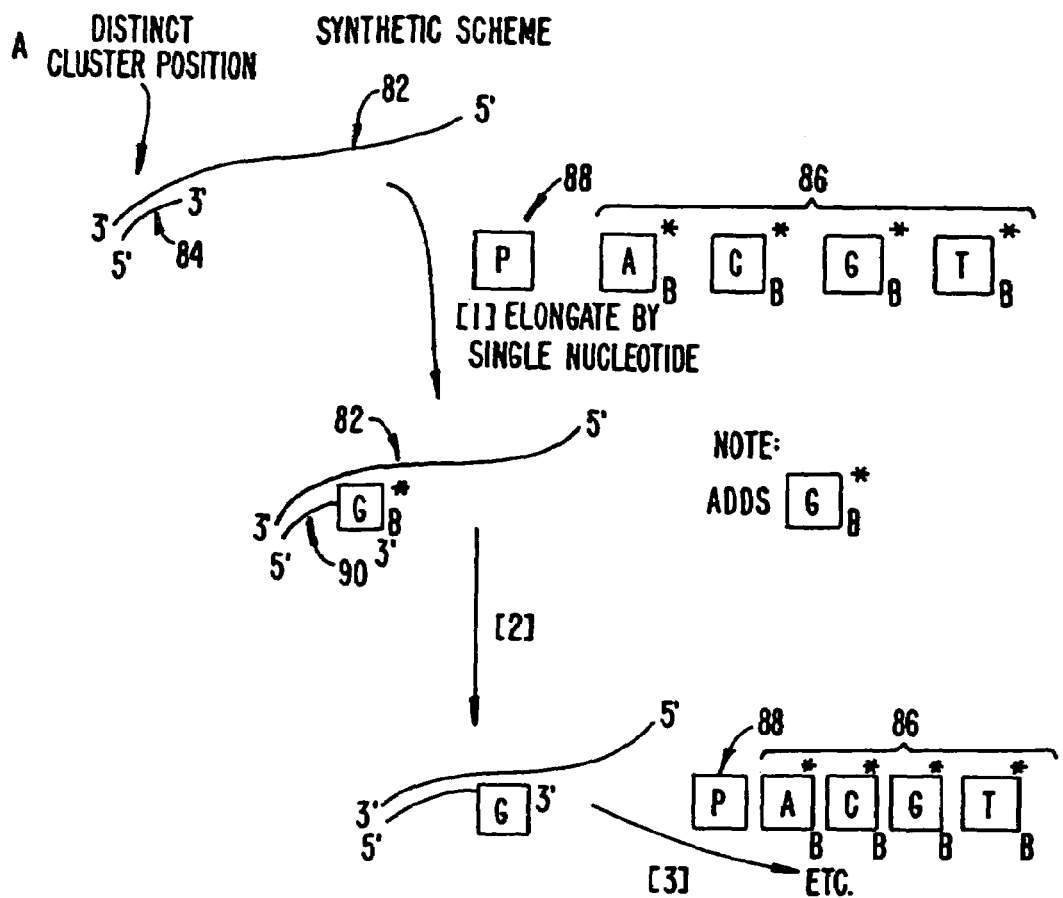
FIG. 8 illustrates the application of the synthetic scheme for sequencing as applied to a nucleic acid cluster localized to a discrete identified position.
Figure 8:
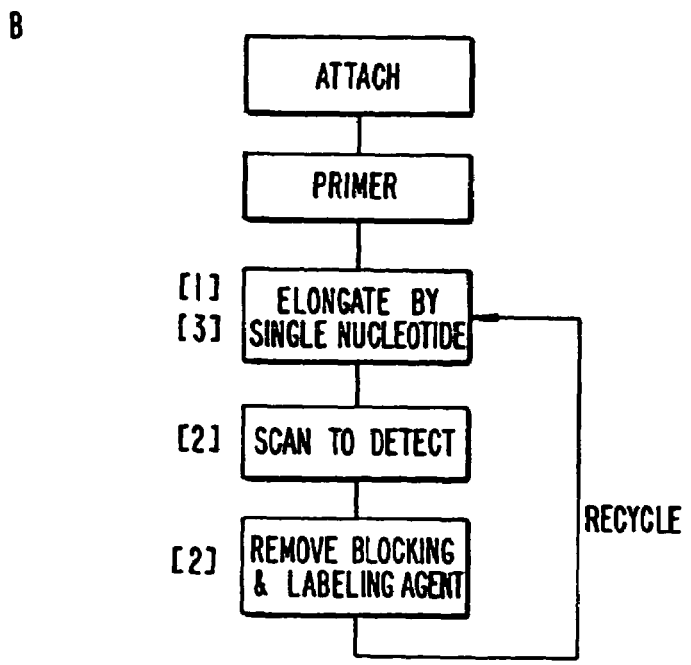

The synthetic mode, as illustrated in FIG. 1 is easily applied to the sequencing of nucleic acids, since one target strand may serve as the template to synthesize the complementary strand. The nucleic acid can be DNA, RNA or mixed polymers. For the purposes of illustration, and not by limitation, the sequencing steps for DNA are described in detail. The synthetic mode, an example of which is depicted in FIG. 8 for nucleotides, may also be useful in circumstances where synthesis occurs in response to a known polymer sequence.

The synthetic scheme depends, in part, on the stepwise elongation by small and identifiable units. A polymerase is used to extend a primer complementary to a target template. The primer is elongated one nucleotide at a time by use of a particular modified nucleotide analog to which a blocking agent is added and which prevents further elongation. This blocking agent is analogous to the dideoxy nucleotides used in the Sanger and Coulson sequencing procedure, but in certain embodiments here, the blockage is reversible. This analog is also labeled with a removable moiety, e.g., a fluorescent label, so that the scanning system can detect the particular nucleotide incorporated after its addition to the polymerization primer.

Panel 4A illustrates the cycle of sequence reactions in one embodiment. The template polymer 82 located at a particular site has already been linked to substrate. The template 82 and complementary primer 84 are hybridized. Often, the primer 84 is common to all of the target template sequences, selected by its common occurrence on a selected cloning vector. The primer 84 is also often covalently crosslinked to the target template 82 using psoralen and U.V. light.

Labeled and blocked monomers 86 are shown, the label depicted by the asterisk and the polymerization blocking groups indicated by B. A compatible polymerase 88 which can elongate the primer with the labeled blocked monomers 86 is used in reaction 1. In the preferred embodiment, the separate labeled monomers can be distinguished from one another by the wavelength of fluorescent emission.

In the example illustrated, a labeled blocked guanosine monomer has been incorporated into the elongated primer 90.

Step 2 is a scan, where the signal at the position corresponding to template 82 indicates that the guanosine analog was incorporated. Reaction 2 is performed, which removes both the label and blocking group. It will be recognized that the blocking group prevents elongation by any more than a single nucleotide in each reaction cycle. Reaction 3 is equivalent to reaction 1, though the substrate primer has been elongated by one monomer.

Panel B illustrates the scheme in a logic flow chart. The template 82 is attached to the substrate, either directly or through the primer. Reaction 1 elongates the primer by a single labeled blocked nucleotide. A scan step is performed and the blocking and labeling agents are removed. The elongation reaction is performed and the cycle repeated.

For a nucleic acid, a unit for addition would typically be a single nucleotide. Under certain circumstances, dimers or trimers or larger segments may be utilized, but a larger number of different possible nucleotide elements requires high distinguishability in other steps. For example, there are only four different nucleotide monomer possibilities, but there are sixteen different dimer possibilities. The distinction among four possibilities is more precise and simple than among sixteen dimer possibilities. To prevent elongation by a unit length greater than one monomer, the nucleotide should be blocked at the position of 3' elongation. Usually, the nucleotide will be blocked at the 3' hydroxyl group where successive nucleotides would be attached. In contrast to a dideoxy nucleotide, typically the blocking agent will be a reversible blocking agent thereby allowing for deblocking and subsequent elongation.

Variations may be easily incorporated into the procedure. If the labels on the monomers are not distinguishable, successive substrate scans can be performed after each monomer is provided with conditions allowing its incorporation. Alternatively, a small fraction of permanently blocked but reversibly labeled monomers may be incorporated. Those specific molecules which incorporate the blocked monomers are permanently removed from further polymerization, but such is acceptable if the labeling moiety is also removed.

1. Other Monomers

One important functional property of the monomers is that the label be removable. The removal reaction will preferably be achieved using mild conditions. Blocking groups sensitive to mild acidic conditions, mild basic conditions, or light are preferred. The label position may be anywhere on the molecule compatible with appropriate polymerization, i.e., complementary to the template, by the selected polymerase. A single polymerase for all of the modified nucleotide is preferred, but a different polymerase for each of the different monomers can be used.

Nucleotide analogs used as chain-terminating reagents will typically have both a labeling moiety and a blocking agent while remaining compatible with the elongation enzymology. As the blocking agent will usually be on the 3' hydroxyl position of the sugar on a nucleotide, it would be most convenient to incorporate the label and the blocking agent at the same site, providing for a single reaction for simultaneous removal of the label and blocking agent. However, it is also possible to put a label on another portion of the nucleotide analog than the 3' hydroxyl position of the sugar, thereby requiring a two-step reaction cycle for removing the blocking and labeling groups.

Analogs will be found by selecting for suitable combinations of appropriate nucleotides with compatible polymerases. In particular, it is desired that a selected polymerase be capable of incorporating a nucleotide, with selectivity, having both the blocking moiety and the label moiety attached. It has been observed that RNA polymerases are less fastidious with respect to the nucleotide analogues which will be polymerized into a growing chain. See, e.g., Rozovaskaya, T., et al. (1977) *Molekulyarnaya Biologiya*, 11:598-610; Kutateladze, T., et al. (1986) *Molekulyarnya Biologiya*, 20:267-276; and Chidgeavadze, Z., et al. (1985) *FEBS Letters*, 183:275-278. Moreover, those references also indicate that rather significant chemical moieties may be attached at the 2' or 3' positions on a nucleotide, and still be correctly incorporated at the growing chain terminus.

In particular, it is not necessary that the same nucleotide have both the reversible blocking moiety and the removable labeling moiety, as a combination of two separate nucleotide analogues could be utilized, e.g., N1, which is reversibly blocked and not labeled, and N2, which is irreversibly blocked but removably labeled. Note that the removal of label may be affected by destruction of the label, e.g., fluorescence destruction, or preferably by removal. Both of these nucleotides might be, for instance, A analogues. With the mixture, at an appropriate sequence position of a target sequence, N1 and N2 nucleotides can be incorporated at an appropriate ratio, and these can be polymerized by either two separate polymerases, or preferably a single polymerase.

For example, two separate polymerases might be necessary, P1 which incorporates N1, and P2 which incorporates N2. At the given location in the sequence, some of the growing polymers will incorporate N1 with P1 polymerase, and others will incorporate N2 with the P2 polymerase. The proportions of N1, N2, P1, and P2 may be titrated to get the desired fractional proportions of the N1 reversibly blocked nucleotides and the N2 labeled but irreversibly blocked nucleotides.

As all of the growing chains have blocked nucleotides, no elongation takes place beyond a single nucleotide. The N2 nucleotides provide a specific label, detected in the scanning step. After determination of the incorporated label, the label may be removed or destroyed, and those irreversibly terminated growing chains become permanently removed from further participation in the sequencing process. Photodestruction may be achieved by a high intensity laser beam of the correct wavelength. See, e.g., March (1977) *Advanced Organic Chemistry: Reactions, Mechanisms and Structure* (2d Ed) McGraw; and Carey and Sundberg (1980) *Advanced Organic Chemistry: part A Structure and Mechanisms*, Plenum.

Next, the reversible blocking moiety is removed, providing a new set of slightly longer polymers ready for the next step. Of course, the amount of label necessary to be incorporated must be detectable, preferably with a clear, unambiguous positive signal. The amount of label incorporated will depend, in part, upon the conditions in the polymerizing step and the relative incorporation of the N1 and N2 nucleotides. The proportions of the nucleotides, polymerases, and other reagents may be adjusted to appropriately incorporate the desired proportions of the nucleotides.

In an embodiment where a single polymerase will incorporate both N1 and N2, the relative proportions and conditions to get the correct incorporation levels of the two nucleotides can be titrated. In an alternative preferred embodiment, a single nucleotide will have both the removable label and the reversible blocking moiety.

A similar approach may be necessary where only some fraction of the nucleotide analogues is labeled. Separate polymerases might also be useful for such situations, and each polymerase may have special conditions necessary for activity.

Procedures for selecting suitable nucleotide and polymerase combinations will be readily adapted from Ruth et al. (1981) *Molecular Pharmacology* 20:415-422; Kutateladze, T., et al. (1984) *Nuc. Acids Res.*, 12:1671-1686; Kutateladze, T., et al. (1986) *Molekulyarnaya Biologiya* 20:267-276; Chidgeavadze, Z., et al. (1985) *FEBS Letters*, 183:275-278; and Rozovskaya, T., et al. (1977) *Molekulyarnaya Biologiya* 11:598-610.

The determination of termination activity is done in two steps. First, nucleotide analogues are screened for the ability of the compound to inhibit polymerase activity. Then the nucleotide analogue is tested for base-specific termination as manifested by generating a correct DNA sequencing ladder on a template of known sequence. The appropriate reaction conditions are those used for conventional sequencing reactions with the respective polymerases. The conditions are then modified in the usual ways to obtain the optimal conditions for the particular terminator compound (e.g. concentration of terminator, ratio of terminator to dNTP, $Mg^{++}$, and other reagents critical to proper polymerase function.

By way of example, an approach employing the polymerase known as reverse transcriptase (AMV) will be described. The initial conditions are essentially as described by Prober, et al. (1987) *Science* 238: 336-341.

A nucleotide analogue is first selected from the group available from a commercial source such as Amersham, New England Nuclear, or Sigma Chemical Company. In particular, nucleotides which are reversibly blocked from further elongation, especially at the 5' or 3'-OH will be used.

General properties which are desired have been described. Each of these analogs can be tested for compatibility with a particular polymerase by testing whether such polymerase is capable of incorporating the labeled analog. Various polymerases may be screened, either natural forms of the mentioned types, or variants thereof. Polymerases useful in connection with the invention include *E. Coli* DNA polymerase (Klenow fragment); and Klenow and Henningsen (1970) *Proc. Nat'l Acad Sci. USA* 65:168-175; and Jacobsen et al. (1974) *Eur. J. Biochem.* 45:623-627; modified and cloned versions of T7 DNA polymerase (Sequenase™ and Sequenase 2.0™); see Tabor and Richardson (1987) *Proc. Nat'l Acad. Sci. USA* 84:4767-4771; and Tabor and Richardson (1987) *J. Biol. Chem.* 262:15330-15333; Taq DNA polymerase from thermostable Thermus aquaticus; see Chien et al. (1976) *J. Bacterol.* 127:1550-1557; and its cloned version Amplitaq; Saiki and Gelfand (1989) *Amplifications* 1:4 6; T4 DNA polymerase; see Nossal (1974) *J. Biol. Chem.* 249: 5668-5676, and various reverse transcriptases, both RNA- and DNA-dependent DNA polymerases, e.g., avian retroviruses; see Houts (1970) *J. Virology* 29:517-522; and murine retroviruses; see Kotewicz et al. (1985) *Gene* 85:249-258; Gerard et al. (1986) *DNA* 5:271-279; and Bst polymerase; see Ye, S. and Hong (1987) *Scientia Sinica* 30:503-506.

In order to ensure that only a single nucleotide is added at a time, a blocking agent is usually incorporated onto the 3' hydroxyl group of the nucleotide. Optimally, the blocking agent should be removable under mild conditions (e.g., photosensitive, weak acid labile, or weak base labile groups), thereby allowing for further elongation of the primer strand with a next synthetic cycle. If the blocking agent also contains the fluorescent label, the dual blocking and labeling functions will be achieved without the need for separate reactions for the separate moieties.

The blocking group should have the functional properties of blocking further elongation of the polymer. Additional desired properties are reversibility and inertness to the sequencing reactions. Preferably, where an enzymatic elongation step is used, the monomers should be compatible with the selected polymerase. Specific examples for blocking groups for the nucleic acids include acid or base labile groups at the 3'OH position. See, e.g., Gait (1984) *Oligonucleotide Synthesis: A Practical Approach*, IRL Press, Oxford.

A DNA-dependent DNA polymerase is the polymerase of choice. Polymerases used for conventional DNA sequencing, for example, Klenow fragment of *E. coli* DNA Pol, Sequenase (modified T7 DNA polymerase), Taq (Thermus aquaticus) DNA polymerase, Bst (*Bacillus stearothermophilus*), DNA polymerase, reverse transcriptase (from AMV, MMLV, RSV, etc.) or other DNA polymerases will be the polymerases of choice. However, there is a functional constraint that the polymerase be compatible with the monomer analogues selected. Screening will be performed to determine appropriate polymerase and monomer analog combinations.

Removal of the blocking groups may also be unnecessary if the labels are removable. In this approach, the chains incorporating the blocked monomers are permanently terminated and will no longer participate in the elongation processes. So long as these blocked monomers are also removed from the labeling process, a small percentage of permanent loss in each cycle can also be tolerated.

The fluorescent label may be selected from any of a number of different moieties. The preferred moiety will be a fluorescent group for which detection is quite sensitive. Various different fluorescence-labeling techniques are described, for example, in Kambara et al. (1988) "Optimization of Parameters in a DNA Sequenator Using Fluorescence Detection," *Bio/Technol.* 6:816-821; Smith et al. (1985) *Nucl. Acids Res.* 13:2399 2412; and Smith et al. (1986) *Nature* 321:674 679, each of which is hereby incorporated herein by reference. Fluorescent labels exhibiting particularly high coefficients of destruction may also be useful in destroying nonspecific background signals.

Appropriate blocking agents include, among others, light sensitive groups such as 6-nitoveratryl-oxycarbonyl (NVOC), 2-nitobenzyloxycarbonyl (NBOC), α,α-dimethyldimethoxybenzyloxycarbonyl (DDZ), 5-bromo-7-nitroindolinyl, o-hydroxy-2-methyl cinnamoyl, 2-oxymethylene anthraquinone, and t-butyl oxycarbonyl (TBOC). Other blocking reagents are discussed, e.g., in Ser. No. 07/492,462; Patchomik (1970) *J. Amer. Chem. Soc.* 92:6333; and Amit et al. (1974) *J. Org. Chem.* 39:192, all of which are hereby incorporated herein by reference. Additional blocking agents attached to particular positions may be selected according to the functional directives provided herein.

Figure 9:
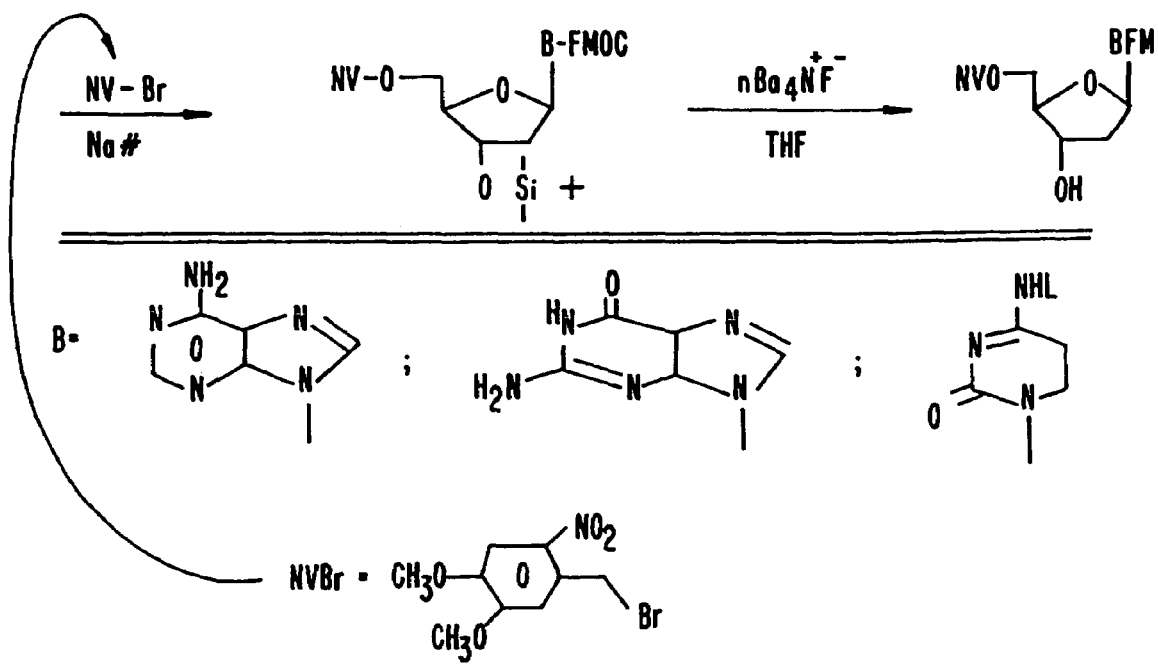
FIG. 9 illustrates the synthesis of a representative nucleotide analog useful in the synthetic scheme. Note that the FMOC may be attached to adenine, cystosine, or guanine.

FIG. 9 schematically illustrates the synthesis of a generic protected nucleotide. A suitable nucleotide is labeled with the FMOC fluorescently detectable label by reaction under the conditions described, e.g., in U.S. Ser. No. 624,114 (sequencing by hybridization), FMOC—Cl, and $H_2O$. A protection moiety will be added using conditions also described there.

Various nucleotides possessing features useful in the described method can be readily synthesized. Labeling moieties are attached at appropriate sites on the nucleotide using chemistry and conditions as described, e.g., in Gait (1984) Oligonucleotide Synthesis. Blocking groups will also be added using conditions as described, e.g., in U.S. Ser. No. 07/624,114 (sequencing by hybridization). FIG. 9 also outlines various reactions which lead to useful nucleotides.

Additionally, the selected polymerases used in elongation reactions should be compatible with nucleotide analogs intended for polymerization to the primer. Simple screening procedures for nucleotide and polymerase combinations may be devised to verify that a particular combination is functional. A test using primer with template which directs the addition of the nucleotide analog to be incorporated will determine whether the combination is workable. Natural polymerases or variants thereof may be used under particular defined conditions.

Figure 10:
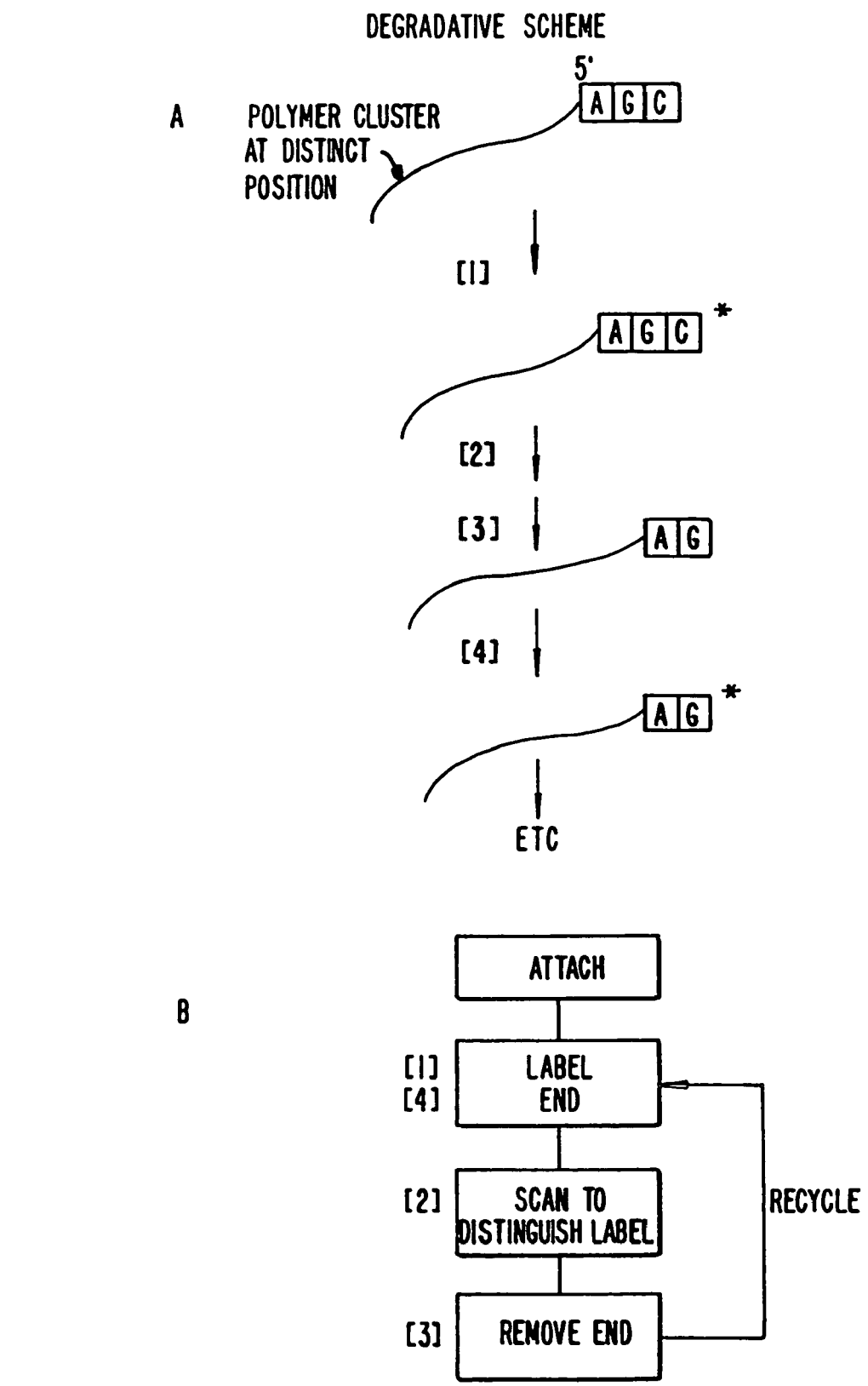
FIG. 10 illustrates the application of the degradative scheme for sequencing as applied to a nucleic acid cluster localized to a discrete identified position.

The degradative scheme is generally illustrated in FIG. 1, an example more generally applicable to biological macromolecular polymers is depicted in FIG. 10. This method is useful for a wider variety of polymers without the limitations imposed by the need to replicate the polymer. The degradative sequencing technique depends, in part, upon the ability to specifically label or distinguish between various different terminal monomers at particular matrix positions. Reactions for specific removal of a defined monomer unit are important.

This monomer distinguishability can arise from an ability to differentiate between label on the various possible monomers in the polymer. As a second means, distinguishability can come from specific reagents which react with particularity on different monomers. Thus, for instance, labels may be used which generally attach to the terminal nucleotide, but whose fluorescent signal differs depending upon the nucleotide. As a third means, a reagent which specifically affects the label on only one monomer may be used, as described below.

In the first example, every polymer cluster will be labeled at a particular end, e.g., the 5' end, without specificity for the monomer located there. The scan step will be able to distinguish the terminal monomers, after which each labeled terminal monomer is specifically removed. The general label step is repeated in the cycle as described.

In the second means for distinguishability, reagents are used which produce a signal which is dependent upon the terminal nucleotide. For example, a labeling molecule which binds only to one specific terminal monomer will provide a monomer specific label. This will provide a cycle much like the first means for distinguishability where the properties of the label is different depending upon the terminal nucleotide to which each specific labeling reagent binds.

In the third means for distinguishability, an individual reagent labels or affects only a specific terminal monomer. Polymers susceptible to each reagent by virtue of terminating with the corresponding monomer will have their labels specifically affected. A scan of the matrix after each step and comparison with the earlier scans will determine which positions correspond to polymers ending with a susceptible monomer. Performing a removal step with a second monomer-specific reagent followed by a scan will identify those positional locations having polymer clusters ending with that second monomer. A similar reagent for the other possible monomers will further define all of the possibilities. Finally, when all of the possible monomers have been removed, the labeling reaction may be repeated and the succession of specific reagent and scanning steps will also be repeated. This procedure allows for a succession of automated steps to determine the sequence of the polymer clusters localized to distinct positions.

Finally, a combination of both specificity of reagent and ability to distinguish label on different monomers can be utilized. Neither alone need be relied upon exclusively. Thus, in the case of nucleotides, an ability to distinguish into two separate classes of nucleotides, e.g., A and C from G and T, combined with specific reagents for distinguishing between the indistinguishable label pairs, e.g., in the example provided, A from C, or G from T, can also provide sufficient information for sequencing.

Instead of performing four specific reactions on the same substrate matrix, each of the four individual reactions can be performed on separate parallel matrices. Four separate substrate matrices may be made by a replica plating or successive transfers, each matrix having the same spatial distribution of polymer clusters. Thus, each separate substrate can be subjected to only a single specific reagent in a highly optimized reaction. On each cycle, one out of the four parallel substrates should show a signal indicating the monomer at the terminal for the cluster at a given matrix position.

Likewise, two parallel substrates can be provided, and each of the parallel substrates is used to determine two of the four possible nucleotides at each position. Instead of treating a single matrix with four separate reactions, this approach allows treating each of two substrates with only two separate reactions. By minimizing the number of reactions to which each chip is exposed, the side reactions will be minimized, the chemistry will be optimized, and the number of cycles through which a matrix will survive will be optimized. This provides an advantage in the number of cycles to which a matrix can be subjected before the signal to noise becomes indistinguishable.

E. Label

The label is important in providing a detectable signal. The signal may be distinguishable among the various monomers by the nature of the signal, e.g., wavelength or other characteristic, as described in Prober et al. (1987) *Science* 238:336-341. A monomer-specific reagent can allow determination of whether each position has a particular terminal monomer by the presence or loss of label.

The label on the monomer may be attached by a noncovalent attachment, but will be preferably attached by a direct covalent attachment. The label will typically be one which is capable of high positional resolution and does not interfere with the nucleotide-specific chemistry or enzymology. Although many different labels may be devised including enzyme linked immunosorbent assays (ELISA), spectrophotometric labels, light producing or other labels, a fluorescent moiety is the preferred form. For example, an avidin/biotin type affinity binding may be useful for attaching a particular label. Alternatively, an antibody may be used which is specific for binding to a particular terminal monomer. A wide variety of other specific reagents can be used to provide a labeling function. See, for example, U.S. Ser. No. 07/624,114 (sequencing by hybridization), which is hereby incorporated herein by reference.

The means of detection utilized will be selected in combination with various other considerations. In some circumstances, a spectroscopic label may be most compatible with a particular monomer. Enzyme linked assays with a spectrophotometric detection system are a workable system. Phosphorescent or light producing assays provide high sensitivity using charged couple devices. Fluorescent systems provide the same advantages, especially where the incident light beam is a laser. The fluorescent label also may provide the added advantage of fluorescing at different wavelengths for the different monomers, providing a convenient means to distinguish between different monomers. Other forms of label may be desired for various reasons, for example, magnetic labels, radioactive labels, heavy metal atoms, optically detectable labels, spectroscopically detectable labels, fluorescent labels, and magnetic labels.

For sequencing nucleic acids by this method, the labeled monomers are simpler than those monomers used for the synthetic method. The blocking group is unnecessary, but terminal specific reagents are more difficult to produce.

The preferred attachment sites will be at the same location as the blocking site, so a combined label and blocking moiety is more preferred. The label will be attached as described, e.g., in U.S. Ser. No. 07/624,114 (sequencing by hybridization).

Two types of degradation cycles can be used, either non-specific removal of the terminal labeled nucleotide, or a base-specific removal. With the non-specific removal means, each of the end monomers, when labeled, should be distinguishable from the other three monomer possibilities. This allows for determination of the terminal nucleotide for the cluster localized at a given matrix position. Then the terminal, labeled nucleotides are non-specifically removed and the newly exposed terminal nucleotides will be again distinguishably labeled.

By this scheme, a specific label for each of the different nucleotides may be provided. For example, fluorescent reagents specific for each of the nucleotides may provide a signal with a different wavelength. This will more usually occur when the fluorescent probe is located near the base moiety of the nucleotide. In the scanning step, the regions terminating with each of the four different nucleotides may be determined. Then, a reaction is performed removing the labeled terminal nucleotides from all of the polymers. This removal may be either enzymatic, using a phosphatase, an exonuclease or other similar enzyme, or chemical, using acid, base, or some other, preferably mild, reagent. Again, the reactions are performed which label each of the terminal nucleotides and a scan step repeated in the same manner.

In the base-specific removal scheme, nucleotide-specific removal can be performed. For example, an enzyme which will function to remove only a single modified nucleotide, e.g., a 5'-fluorescein-dAMP-specific exonuclease, is constructed. This may be achieved by proper construction of a catalytic antibody. Other similar reagents may be generated for each of the other labeled nucleotide monomers.

Catalytic or derivatized antibodies to catalyze the removal of the 3'-end or 5'-most fluorescent base in a base-specific manner may be constructed as follows. A recombinant antibody library or a series of monoclonal antibodies is screened with fluorescent donor-quencher substrates. These substrates consist of a fluorescent labeled base (A, C, G, or T) on the 5' or 3' end joined by a 5' to 3' phosphodiester linkage to a second base. A collection of all four possible second bases for each of the four end bases gives the best selection target for the required non-specificity with respect to the second base. The second base is then tethered to an acceptor group in sufficient proximity to quench the fluorescence of the end group. In the presence of a catalytic antibody with cleaving activity, a fluorescent signal occurs from the separation of the quenching group from the terminal fluorescent label. To assure both base and end specificity, the positive monoclonal antibody clones are rescreened against the other substrates.

Upon selection of an antibody exhibiting the desired specificity (or lack thereof), the reactive group for cleavage may be attached. This cleavage reagent may be chemical or enzymatic and will be attached by an appropriate length linker to the antibody binding site in an orientation which is consistent with the steric requirements of both binding and specific cleavage.

Particularly useful specific reagents may be produced by making antibodies specific for each of the four different modified terminal nucleotide bases. These antibodies would then specifically bind only to polymers terminating in the appropriate base analog. By combining a cleavage reagent to the specific antibody, a terminal nucleotide specific cleavage reagent is generated.

In one example of the degradative embodiment, all of the polymers may be uniformly labeled at a particular end. Thereafter, a specific removal reaction which removes only a particular nucleotide may be performed, leaving the three other nucleotides labeled. Thereafter, a scanning step is performed through which all regions which had incorporated that particular nucleotide will have lost the label through specific removal. Then, the second specific reagent will be applied which specifically removes the second labeled nucleotide, and the scanning step following that reaction will allow determination of all regions which lose the second particular nucleotide. This process is repeated with reagents specific for each of the last two remaining labeled nucleotides interspersed with scanning steps, thereby providing information on regions with each of the nucleotides located there. Then, the entire process may be repeated by labeling the next terminal nucleotides uniformly. As mentioned below, replication techniques may allow for making four separate but identical matrix substrates. Each substrate may be subjected to single nucleotide-specific reactions, and the scan results correlated with each of the other parallel substrates.

In the degradation scheme, the polynucleotide linkage to the matrix must be more carefully selected such that the free end of the oligonucleotide segments used for attachment will not interfere with the determinations of the target sequence terminus.

F. Utility

The present sequencing method is useful to monitor and check the accuracy and reliability of the synthetic processes described in U.S. Ser. No. 07/362,901 (VLSIPS parent) and U.S. Ser. No. 07/492,462, now U.S. Pat. No. 5,143,854 (VLSIPS CIP). The present method can be used to check the final products synthesized therein, or to label each monomer as they are added stepwise to monitor the efficiency and accuracy of those synthetic methods.

The present invention can also be used to monitor or sequence matrix bound clusters of positionally distinct polymers. This sequencing process provides the capability of simultaneously sequencing a large plurality of distinct polymers which are positionally segregated.

The method will be used to sequence extremely large stretches of polymer, e.g., nucleic acids. A large number of shorter segments of a large sequence can be sequenced with alignment of overlaps either randomly generated, or in an ordered fashion, or particular sequenceable segments of a large segment can be generated. In one approach, a large segment is subcloned into smaller segments and a sufficient number of the randomly generated subclones are sequenced as described herein to provide sequence overlap and ordering of fragments.

In an alternative approach, a large segment can be successively digested to generate a succession of smaller sized subclones with ends separated by defined numbers of monomers. The subclones can be size sorted by a standard separation procedure and the individual samples from a separation device manually or automatically linked to a matrix in a defined positional map. Fractions resulting from size separation can be spatially attached at defined positions, often at adjacent positions. Then polymer sequences at adjacent positions on the matrix will also be known to have ends which differ by, e.g., approximately 25 or 50 or more monomers, thereby providing significantly greater confidence in overlapping sequence data.

II. Specific Embodiments

A specific series of reactions for sequencing a matrix of polynucleotides is described.

A. Synthetic Method

This method involves annealing a primer (common to all the attached sequences by virtue of the cloning construction) near to the 3' end of the unknown target sequences. DNA polymerase, or a similar polymerase, is used to extend the chains by one base by incubation in the presence of dNTP analogs which function as both chain terminators and fluorescent labels. This is done in a one-step process where each of the four dNTP analogs is identified by a distinct dye, such as described in Prober et al., *Science* 238:336-341, or in four steps, each time adding one of the four bases, interspersed with a scanning identification step. When each cluster incorporates the proper one of the four bases and the fluorescence scanning is complete, the matrix is stripped of the label and the chain terminators are deblocked for a next round of base addition. Because the base addition is directed by the template strand, the complementary sequence of the fragments at each address of the matrix is deduced.

1. Attachment to a Surface

Both degradative and synthetic sequencing methods begin by obtaining and immobilizing the target fragments of unknown sequence to be determined at specific locations on the surface.

There are several strategies for photo-directed attachment of the DNA strands to the surface in an orientation appropriate for sequencing. A caged biotin technique, see, e.g., U.S. Ser. No. 07/435,316 (caged biotin parent), and U.S. Ser. No. 07/612,671 (caged biotin CIP), is available. Another technique that is especially applicable for the enzymatic synthesis method is to chemically attach a synthetic oligomer by the 5' end to the entire surface (see FIG. 6), to activate it for photocrosslinking (with psoralen, for example) and to anneal the complementary strands and photocrosslink the target strand of unknown sequence (complementary to this oligonucleotide at the 3' end) at the specific location addressed by light. In this case, the oligonucleotide serves as both the attachment linker and as the synthetic primer. A third method is to physically transfer individual nucleic acid samples to selected positions on the matrix, either manually or automatically.

Many sequences in each step are attached by cloning the library into a series of vectors identical except for the sequences flanking the insert. These primers can be added at the point of amplification of the cloned DNA with chimeric primers.

Alternatively, sequences are attached to a matrix substrate by colony or phage immobilization. This directly transfers the positional distribution on a petri plate to a usable substrate. Colonies representing a shotgun collection of sequences (enough to assure nearly complete coverage by overlap) are spread over (or in) a nutrient surface at a density to give about 100 or more colonies or plaques in several square centimeters, and the colonies are allowed to grow to about 0.1 mm in diameter (the maximum possible density of clusters at this size is ~10,000 colonies/cm$^2$). As described above, replica platings or successive transfers may allow for preparation of multiple matrices with identical positional distributions of polymers. Each separate matrix may then be dedicated to the reactions applicable to a single monomer.

For example, in the use of a phage library, on a petri dish, the transfer substrate surface is treated to release DNA from the phage. This is done, e.g., with $CHCl_3$ vapor, SDS-NaOH, or by heating. Prior to release of DNA, the phage particles are often adsorbed to the surface by way of an antibody to the coat protein that has been immobilized on the surface. This strategy prevents diffusion of the phage from the colonies. The matrix surface is prepared by coating with an oligonucleotide, immobilized to the surface by one end that has homology with the phage vector DNA adjacent to the cloning site.

The matrix surface is juxtaposed to the growth surface, and the phage DNA is allowed to anneal to the immobilized oligonucleotide. The growth surface is removed, and the hybrid is stabilized by psoralen or an equivalent crosslinking reagent.

This method provides an efficient one-step method of placing many DNA fragments onto the detection surface in preparation for sequencing. Although the colonies are not placed in predefined locations, the random arrangement of the clusters allows the final sequence to be assembled from correlation of overlap sequence data derived from sequence data derived from each of the defined positions of each target cluster.

Sequences are, in other embodiments, attached by a manual or automated transfer technique. A few cells from each colony in a library are toothpicked into microliter wells. The plate is heated to ~100° C. for a short period to lyse the cells and release the DNA. The plate is cooled and reagents for cycled amplification of the DNA using, e.g., PCR technology, are added, including primers common to all the cloned sequences. See, e.g., Innis et al. (1990) *PCR Protocols: A Guide to Methods and Applications*, Academic Press, which is hereby incorporated herein by reference. The DNA is amplified asymmetrically by unbalanced primer concentration to yield an excess of one strand for sequencing and attached to a substrate by manual or automated means.

An alternative form of automated localization is described above in positioning of a succession of smaller sized polymers which are manually or automatically linked to the substrate in a pattern reflecting sequence overlaps.

2. Enzymatic Polymerization Method

The nucleic acid template is, in some embodiments, attached to the surface by either the 5' or the 3' end, usually by a method as described above. A preferred method of attachment is to anneal the template to an oligonucleotide attached to the surface and to crosslink the template to the oligonucleotide. Oligonucleotide primers are usually synthesized chemically. In this case, the immobilized oligonucleotide may also serve as a primer for polymerization. Because polymerization proceeds 5' to 3' on the primer, the template will be attached by its 3' end, or a site 3' proximal to the region to be sequenced, for the purposes of the description to follow.

Step 1: A DNA-dependent, DNA polymerase such as those used for conventional DNA sequencing, for example, Klenow fragment of *E. coli* DNA Pol, Sequenase™ (modified T7 DNA polymerase), Taq (Thermus aquaticus) DNA polymerase, Bst (*Bacillus stearothermophilus*), DNA polymerase, reverse transcriptase (from AMV, MMLV, RSV, etc.) or other DNA polymerases, and the reaction components appropriate to the particular DNA polymerase selected, are placed in the incubation chamber in direct contact with the surface.

Step 2: Fluorescent chain terminators (analogs of dATP, dCTP, dGTP, and TP, each labeled with fluorophore preferably emitting at a distinguishable wavelength) are added to the reaction at a sufficient concentration and under suitable reaction conditions (time, temperature, pH, ionic species, etc., see Sambrook et al. (1989) *Molecular Cloning*, vols. 1-3, and Prober et al.) to cause essentially all of the chains on the surface to be extended by one base and thereby terminated. Detection of the specific label thereby incorporated into each chain identifies the last base added at each positional address in the matrix.

Step 3: The chain termination should be reversible by some means, such as treatment with light, heat, pH, certain other chemical or biological (enzymatic) reagents, or some combination of these. Typically the chain termination results from a blocking moiety which is labile to mild treatment. By one of these means, the blocked 3'OH of the terminating base must be made available for chain extension in the next round of polymerization.

Step 4: There are several suitable labeled, terminator structures as follows:

(a) The fluorophore itself functions as the chain terminator by placement on the 3' hydroxyl through a linkage that is easily and efficiently cleaved (removing the label and leaving the free 3'OH) by light, heat, pH shift, etc. The surface is scanned with a scanning system, e.g., the fluorescence detection system described in U.S. Ser. No. 07/492,462, now U.S. Pat. No. 5,143,854 (VLSIPS CIP); and U.S. Ser. No. 07/624,120 (automated VLSIPS). Then, preferably in a single step, the fluorophore is removed and the chain is activated for the next round of base addition.

(b) The fluorophore is placed in a position other than the 3'OH of the nucleoside, and a different group is placed on the 3'OH of the dNTPs to function as a chain terminator. The fluorophore and the 3' blocking group are removed by the same treatment in a single step (preferably), or they may be removed in separate steps.

(c) An alternative polymer stepwise synthetic strategy can be employed. In this embodiment, the fluorophores need not be removable and may be attached to irreversible chain terminators. Examples of such compounds for use in sequencing DNA include, but are not limited to, dideoxynucleotide triphosphate analogs as described by Prober et al. (1987) *Science* 238:336-341. A second, unlabeled and reversible, set of terminators is also required. Examples of these compounds are deoxynucleotide triphosphates with small blocking groups such as acetyl, tBOC, NBOC and NVOC on the 3'OH. These groups are easily and efficiently removed under conditions of high or low pH, exposure to light or heat, etc. After each round of base addition and detection, the fluorophores are deactivated by exposure to light under suitable conditions (these chains have their labeling moiety destroyed and remain terminated, taking part in no further reactions). The unlabeled, reversible terminators are unblocked at the 3'OH by the appropriate treatment to allow chain extension in subsequent rounds of elongation. The proportion of chains labeled in each round can be controlled by the concentration ratio of fluorescent to non-fluorescent terminators, and the reaction can be driven to completion with high concentrations of the unlabeled terminators.

(d) A single dye strategy is used where all the base analog terminators carry the same fluorophore and each is added one at a time: A, C, G, T. The addition of each base is followed by scanning detection. After all four fluorophores are added, reversal of the termination is performed, allowing for the addition of the next base analog. Then, each scanning step determines whether the immediately preceding labeled nucleotide had been incorporated at each distinct position.

The structures of the fluorescently labeled and reversible terminator base analogs are selected to be compatible with efficient incorporation into the growing chains by the particular DNA polymerase(s) chosen to catalyze extension. For example, where two different chain terminators are used, they may be utilized by two different polymerases that are both present during the chain extension step.

Step 5: An optional step is the permanent capping of chain extension failures with high concentrations of dideoxynucleotide triphosphates. This step serves to reduce the background of fluorescence caused by addition of an incorrect base because of inefficient chain extension (termination) at an earlier step.

Step 6: After scanning to determine fluorescence, the fluorophore is removed or deactivated. Deactivation of the fluorophore can be achieved by a photodestruction event. The chain elongation block is reversed (usually by removing a blocking group to expose the 3'OH) by suitable methods that depend on the particular base analogs chosen; and the substrate is washed in preparation for the next round of polymerization.

Step 7: Repeat the cycle.

B. Chain Degradation Method

This method involves labeling the last base of the chain (distal to the surface attachment) with a fluorescent tag followed by base-specific removal. All the polynucleotide clusters on the matrix are labeled using a standard labeling moiety. Base-specific removal of the last base of each chain, interspersed with fluorescence scanning of the array, will reveal the disappearance of fluorescence and hence the identity of the last base of each chain. When all four labeled end bases have been removed, the polymers attached to the matrix are relabeled and the process is repeated, working successively on the DNA chains.

Alternatively, if the label allows distinguishing between different monomers, simpler degradation processes may be employed. A single scan step can distinguish between all four possible terminal nucleotides. The four separate removal steps are then combined into a single nonspecific terminal nucleotide removal step.

The DNA will usually be attached to the substrate by the 3' or 5' terminus depending on the scheme of labeling and cleavage. Because there are well-known 5' labeling methods, see, e.g., Gait (1984) *Oligonucleotide Synthesis: A Practical Approach*, IRL Press, Oxford, this discussion will assume the 3' end is attached to the substrate with the 5' end free.

Step 1: All the 5'-end bases are labeled with 5' specific chemistry, e.g., 5' amino linkage to FITC, Nelson et al. (1989) *Nucl. Acids Res.* 17:7179-7186, which is hereby incorporated herein by reference.

Step 2: Scan the matrix to obtain the background level.

Step 3: Optional: Cap all of the labeling failures, e.g., polymers whose ends were not labeled.

Step 4: The terminal A's are removed with end-base, A-specific reagents (such a reagent may be chemical or biological). One example is a 5' fluorescein-dAMP-specific exonuclease made as a catalytic antibody (see the description above for a scheme of producing this reagent).

Step 5: Scan the matrix to detect those chains that had terminated in A (these will be reduced in fluorescence compared to the fluorescently labeled background).

Step 6: Repeat steps 4 and 5 for each of other three possible bases using the appropriate fluorescein-base-specific cleavage reagent and scan after removal of each of the C's, the G's, and the T's. This succession of steps will allow the determination of the terminal nucleotide of each positionally defined cluster.

Step 7: Relabel the 5' terminal nucleotide of all the new end bases that have been exposed by the earlier rounds of cleavage, and repeat the stepwise removal and scanning processes.

This approach can be extended to protein sequencing using 20 catalytic antibodies (or other amino acid-specific cleavage reagents), each recognizing a terminal amino acid and removing that terminal residue.

The process for sequencing may be summarized as follows for enzymatic polymerization:

1) Target DNA templates (to be sequenced) are attached at positionally defined locations on the matrix substrate.

2) Fluorescent chain terminators are added to a primer under conditions where all polymer chains are terminated after addition of the next base complementary to the template.

3) The matrix is scanned to determine which base was added to each location. This step correlates the added base with a position on the matrix.

4) Chains failing to extend (and therefore to terminate) are capped.

5) The fluorophores are removed or deactivated.

6) The terminators are activated for further chain extension, usually by removal of a blocking group.

7) Steps 2 through 6 are repeated to obtain the base-by-base sequence of many different positionally separated DNA fragments simultaneously.

C. Screening for New Nucleotide Analog/Polymerase Combination.

The use of a functional combination of blocked nucleotide with a polymerase is important in the synthetic embodiment of the present invention. It is important to ensure that only a single nucleotide is incorporated at the appropriate step. The following protocol describes how to screen for a functional combination.

Test 1 (Test for Polymerase Inhibition)
In a reaction volume of 20 µl, mix
1 µg M13mp19 single stranded DNA template
2.5 ng standard M13 primer (17-mer: 5'-GTTTTC-CCAGTCACGAC-3')
60 mM tris-Cl pH 8.5
7.5 mM $MgCl_2$
75 mM NaCl
Template and primer are annealed by heating to 95° C., then cooling to ~25° C.

Extension components are added:
50 µM (each) dATP, dCTP, dGTP, TTP;
10 µCi P32 dATP;
0.01 µM to 1 mM of the putative terminator compound, further titrations may be desired;
20 units AMV reverse transcriptase;
water to 20 µl final volume;
The reaction is run at 42° C. for about 30 minutes.

Aliquots are taken at 10, 20, 30 minutes, and samples are TCA precipitated after the addition of 10 µg tRNA carrier.

The filters are counted for acid-precipitable radioactivity and the mass of dATP incorporated is calculated as a function of reaction time.

Control reactions are run in parallel consisting of
A) no added terminator
B) 10µM and 100 µM The termination activity of the experimental samples relative to that of ddNTPs is estimated, and a nucleotide is appropriate for further testing if it substantially decreases the number of acid precipitable counts at any time or relative concentration.

Test 2 (Test for Base Specific Termination Activity)
Reactions are run essentially as described by Prober et al. except:
1. Unlabelled primer is used
2. 1 µCi $^{32}$P dATP is included
3. No dideoxyNTPs are added to the experimental samples (control reactions containing ddNTP at the usual concentrations, and no test terminators are run in parallel)
4. The test compound is added at a concentration estimated to give 1% and 10% inhibition of incorporation as determined by test # 1.

The reactions are run for 10 min at 42° C. 100 µM dNTPs are added and the reaction run for an additional 10 min. A portion of the reaction is prepared and run on a sequencing gel in the usual fashion. The ladders obtained with the test compound are compared with those obtained in the ddNTP reactions and the fidelity of the termination activity of the test compound is thereby assessed.

III. Apparatus

Figure 11:
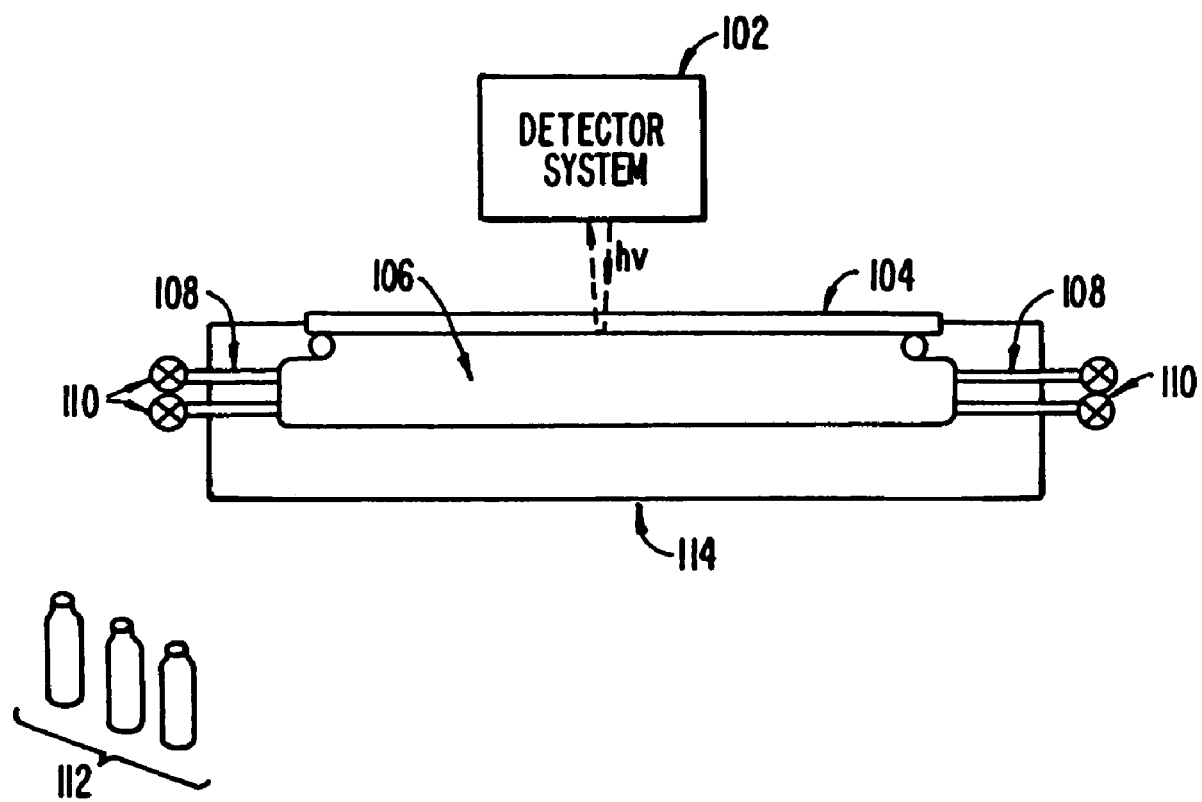
FIG. 11 illustrates a functionalized apparatus for performing the scanning steps and sequencing reaction steps.

The present invention provides a new use for an apparatus comprising a reaction chamber and a scanning apparatus which can scan a substrate material exposed to the chamber. FIG. 11 illustrates a system and a schematized reaction chamber to which is attached a silicon or glass substrate. The system has a detection system 102 as illustrated, in one embodiment, in FIG. 7. A silicon substrate 104, is attached against and forming a seal to make a reaction chamber 106. Leading into and out of the chamber are tubes 108, with valves 110 which control the entry and exit of reagents 112 which are involved in the stepwise reactions. The chamber is held at a constant temperature by a temperature block 114.

All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the claims.

What is claimed is:

1. A method for analyzing a target nucleic acid comprising:
 (a) providing a nucleic acid array, said array comprising at least two different target template nucleic acids attached to a support in positionally distinct regions at a density of at least 1000 regions per $cm^2$;
 (b) contacting said nucleic acid array with at least one nucleotide comprising a removable label;
 (c) detecting the label to determine the addition of the nucleotide to an oligonucleotide hybridized to one of the template nucleic acids;
 (d) removing the label; and
 (e) repeating steps (b) and (c).

2. The method of claim 1, wherein the at least two different target template nucleic acids are attached to different beads.

3. The method of claim 1, wherein the nucleotide further comprises a removable blocking group that blocks addition of other nucleotides and the method further comprises removing the blocking group following determination of addition of the nucleotide.

4. The method of claim 3, wherein the removal of the label and the blocking group comprises a reaction that removes both the label and the blocking group.

5. The method of claim 1, wherein the array is contacted with four differentially labeled nucleotides and the determining step determines which nucleotide is added based on the type of label.

6. A method for analyzing a target nucleic acid comprising:
 (a) providing a nucleic acid array, said array comprising at least two different target template nucleic acids attached to a support in positionally distinct regions at a density of at least 1000 regions per $cm^2$;
 (b) contacting said nucleic acid array with at least one nucleic acid segment of a defined length; and
 (c) determining the addition of the nucleic acid segment to an oligonucleotide hybridized to one of the target template nucleic acids.

7. The method of claim 6, wherein the at least two different target template nucleic acids are attached to different beads.

8. The method of claim 6, wherein the nucleic acid segment comprises a label and determining the addition of the nucleic acid segment comprises detection of the label.

9. The method of claim 8, wherein the label is removable.

10. The method of claim 9, further comprising removing the label following determination of the addition of the nucleic acid segment.

11. The method of claim 8, wherein the nucleic acid segment further comprises a blocking group that blocks addition of nucleotides.

12. The method of claim 11, wherein each of the labels and the blocking groups are removable.

13. The method of claim 12, further comprising removing the label and the blocking group following determination of addition of the nucleic acid segment.

14. The method of claim 13, wherein the removal of the label and the blocking group comprises a reaction that removes both the label and the blocking group.

15. The method of claim 13, further comprising repeating steps (b) and (c) following the removal of the label and the blocking group.

16. The method of claim 8, wherein the array is contacted with differentially labeled nucleotides and the determining step determines which nucleic acid segment is added based on the type of label.

* * * * *